US010667522B2

(12) United States Patent
Curtis et al.

(10) Patent No.: US 10,667,522 B2
(45) Date of Patent: Jun. 2, 2020

(54) **COMPOSITIONS COMPRISING RECOMBINANT *BACILLUS* CELLS AND ANOTHER BIOLOGICAL CONTROL AGENT**

(71) Applicant: BASF CORPORATION, Ludwigshafen am Rhein (DE)

(72) Inventors: Damian Curtis, Davis, CA (US); Brian Thompson, Creve Coeur, MO (US)

(73) Assignee: BASF SE, Florham Park, NJ (US)

( * ) Notice: Subject to any disclaimer, the term of this patent is extended or adjusted under 35 U.S.C. 154(b) by 0 days.

(21) Appl. No.: 15/511,822

(22) PCT Filed: Sep. 17, 2015

(86) PCT No.: PCT/US2015/050592
§ 371 (c)(1),
(2) Date: Mar. 16, 2017

(87) PCT Pub. No.: WO2016/044529
PCT Pub. Date: Mar. 24, 2016

(65) Prior Publication Data

US 2017/0318808 A1 Nov. 9, 2017

Related U.S. Application Data

(60) Provisional application No. 62/051,911, filed on Sep. 17, 2014.

(51) Int. Cl.

| | |
|---|---|
| ***A61K 39/002*** | (2006.01) |
| ***A01N 63/00*** | (2020.01) |
| ***C07K 14/32*** | (2006.01) |
| ***A01N 37/46*** | (2006.01) |
| ***A01N 63/10*** | (2020.01) |
| *A01N 37/00* | (2006.01) |
| *C07K 14/00* | (2006.01) |

(52) U.S. Cl.
CPC ............ *A01N 63/00* (2013.01); *A01N 37/46* (2013.01); *A01N 63/10* (2020.01); *C07K 14/32* (2013.01); *A01N 37/00* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 6,060,051 | A | 5/2000 | Heins et al. |
| 6,184,440 | B1 | 2/2001 | Shoseyov et al. |
| 6,333,302 | B1 | 12/2001 | Beer et al. |
| 7,615,681 | B2 | 11/2009 | Georges et al. |
| 8,461,419 | B2 | 6/2013 | He et al. |
| 9,132,175 | B2 | 9/2015 | Stewart et al. |
| 9,133,251 | B2 | 9/2015 | Stewart et al. |
| 9,573,980 | B2 | 2/2017 | Thompson et al. |
| 2003/0228679 | A1 | 12/2003 | Smith et al. |
| 2011/0281316 | A1 | 11/2011 | Stewart et al. |
| 2013/0216653 | A1 | 8/2013 | Perkins et al. |
| 2014/0274707 | A1 | 9/2014 | Thompson et al. |
| 2016/0031948 | A1 | 2/2016 | Thompson et al. |
| 2016/0051656 | A1 | 2/2016 | Stewart et al. |
| 2016/0053222 | A1 | 2/2016 | Stewart et al. |
| 2016/0108096 | A1 | 4/2016 | Thompson et al. |

FOREIGN PATENT DOCUMENTS

| | | | |
|---|---|---|---|
| WO | 02/00232 | A2 | 1/2002 |
| WO | 2003/066846 | A1 | 8/2003 |
| WO | 2005/028654 | A1 | 3/2005 |
| WO | 2005118552 | A2 | 12/2005 |
| WO | 2006/012366 | A1 | 2/2006 |
| WO | 2007/078127 | A1 | 7/2007 |
| WO | 2008/017483 | A2 | 2/2008 |
| WO | 2010/128003 | A2 | 11/2010 |
| WO | 2013110591 | A1 | 8/2013 |
| WO | 2016/044529 | A1 | 3/2016 |
| WO | 2016/044533 | A1 | 3/2016 |
| WO | 2016/044542 | A1 | 3/2016 |
| WO | 2016/044548 | A1 | 3/2016 |
| WO | 2016/044563 | A1 | 3/2016 |
| WO | 2016/044575 | A1 | 3/2016 |

OTHER PUBLICATIONS

Mikayama et al. (Nov. 1993. Proc.Natl.Acad.Sci. USA, vol. 90 : 10056-10060).*

Rudinger et al. (Jun. 1976. Peptide Hormones. Biol.Council. pp. 5-7).*

Berlemont, R., et al., "Phylogenetic Distribution of Potential Cellulases in Bacteria," Mar. 2013, Applied and Environmental Microbiology, vol. 79, No. 5, pp. 1545-1554.

Chapman K. D., "Phospholipase Activity During Plant Growth and Development and in Response to Environmental Stress," Trends in Plant Sciences, 1998, vol. 3, pp. 419-426.

(Continued)

*Primary Examiner* — Jennifer E Graser
(74) *Attorney, Agent, or Firm* — McBee Moore & Vanik, IP LLC

(57) ABSTRACT

The present invention relates to a composition comprising a) recombinant exosporium-producing *Bacillus* cells that express a fusion protein comprising: (i) at least one plant growth stimulating protein or peptide and (ii) a targeting sequence that localizes the fusion protein to the exosporium of the *Bacillus* cells; and b) at least one further biological control agent selected from particular microorganisms disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount. Furthermore, the present invention relates to the use of this composition as well as a method for enhancing plant growth, promoting plant health, and/or reducing overall damage of plants and plant parts.

18 Claims, 1 Drawing Sheet

Specification includes a Sequence Listing.

(56) References Cited

OTHER PUBLICATIONS

Choudhary, D.K., "Interactions of *Bacillus* spp. and Plants—With Special Reference to Induced Systemic Resistance (ISR)," Microbiological Research, 2009, vol. 164, pp. 493-513.
Curtis, et al., U.S. Appl. No. 14/857,176, filed Sep. 17, 2015, titled "Compositions Comprising Recombinant Bacillus Cells and Another Biological Control Agent."
Curtis, et al., U.S. Appl. No. 15/511,835, filed Mar. 16, 2017, titled "Compositions Comprising Recombinant Bacillus Cells and a Fungicide."
Curtis, et al., U.S. Appl. No. 15/511,844, filed Mar. 16, 2017, titled "Compositions Comprising Recombinant Bacillus Cells and an Insecticide."
Curtis, et al., U.S. Appl. No. 15/511,839, filed Mar. 16, 2017, titled "Compositions Comprising Recombinant Bacillus Cells and Another Biological Control Agent."
Curtis, et al., U.S. Appl. No. 15/511,854, filed Mar. 16, 2017, titled "Compositions Comprising Recombinant Bacillus Cells and a Fungicide."
Curtis, et al., U.S. Appl. No. 15/511,864, filed Mar. 16, 2017, titled "Compositions Comprising Recombinant Bacillus Cells and an Insecticide."
Dowd, P.E., et al., "The Emerging Roles of Phospholipase C in Plant Growth and Development," T. Munnik (ed.), Lipid Signaling in Plants, Plant Cell Monographs 16, 2010, pp. 23-37.
Gnanaraj, M., et al., "Isolation and Gene Expression Analysis of Phospholipase C in Response to Abiotic Stresses from *Vigna radiata* (L.) Wilczek," Jun. 2015, Indian Journal of Experimental Biology, vol. 53, pp. 335-341.
Gujar, P.D., et al., "Effect of Phytase from Aspergillus niger on Plant Growth and Mineral Assimilation in Wheat (*Triticum aestivum* Linn.) and Its Potential for Use as a Soil Amendment," 2013, J. Sci. Food Agric., vol. 93, pp. 2242-2247.
Hafeez, F.Y., et al., "PGPR: Versatile Tool to Combat Soil Borne Pathogens and Improve Plant Health," 2011, Aspects of Applied Biology, vol. 106, pp. 241-245.
Han, W., et al., "The Application of Exogenous Cellulose to Improve Soil Fertility and Plant Growth Due to Acceleration of Straw Decomposition," Bioresource Technol, 2010, vol. 101, pp. 3724-3731.
Hartati, et al., "Overexpression of Poplar Cellulase Accelerates Growth and Disturbs the Closing Movements of Leaves in Sengon," Plant Physiology, 2008, vol. 147, pp. 552-561.
Hong, Y., et al., "Phospholipases in Plant Response to Nitrogen and Phosphorus Availability," Springer, Phospholipases in Plant Signaling and Communication in Plants, 2013, vol. 20, pp. 159-180.
Hontzeas, N., et al., "Changes in Gene Expression in Canola Roots Induced by ACC-Deaminase-Containing Plant-Growth-Promoting Bacteria," 2004, MPMI, vol. 17, No. 8, pp. 865-871.
International Search Report and Written Opinion of the International Searching Authority, PCT International Patent Application No. PCT/US2015/050592, dated Nov. 11, 2015, 12 pages.
International Search Report and Written Opinion of the International Searching Authority, PCT International Patent Application No. PCT/US2015/050621, dated Nov. 3, 2015, 12 pages.
Idriss, et al., "Extraccellular Phytase Activity of Bacillus amyloliquefaciens FZB45 Contributes to its Plant-growth-promoting Effect," Microbiology, 2002, vol. 148, pp. 2097-2109.
Jackson, W.T., "Effect of Pectinase and Cellulase Preparations on the Growth and Development of Root Hairs," Physiologia Plantarum, 2006 (first published in 1959), vol. 12, pp. 502-510.
Kong, Z., et al., "Effects of 1-Aminocyclopropane-1-carboxylate (ACC) Deaminase-Overproducing Sinorhizobium meliloti on Plant Growth and Copper Tolerance of Medicago lupulina," Jun. 2015, Plant and Soil, vol. 391, issue 1, pp. 383-398.
Li, J. et al., "An ACC Deaminase Minus Mutant of Enterobacter cloacae UW4 No Longer Promotes Root Elongation," 2000, Current Microbiology, vol. 41, pp. 101-105.
Li, W., et al., "Cloning of the Thermostable Cellulase Gene From Newly Isolated Bacillus subtilis and its Expression in *Escherichia coli*," Molecular Biotechnology, 2008, vol. 40, No. 2, pp. 195-201.
Medie, F. M., "Genome Analyses Highlight the Different Biological Roles of Cellulases," Nature Reviews Microbiology, Mar. 2012, vol. 10, pp. 227-234.
Phitsuwan, P., et al., "Present and Potential Applications of Cellulases in Agriculture, Biotechnology, and Bioenergy," 2013, Folia Microbiol, vol. 58, pp. 163-176.
Pilar-Izquierdo, et al.,"Barley seed coating with free and immobilized alkaline phosphatase to improve P uptake and plant growth," Journal of Agricultural Science, 2012, vol. 150, pp. 691-701.
Ping, R., et al., Abstract, 2005, Journal of Northwest Forestry College, vol. 20, No. 1: 78-79.
Raddadi, N., et al., "Screening of Plant Growth Promoting Traits of Bacillus thuringiensis," 2008, Annals of Microbiology, vol. 58, No. 1, pp. 47-52.
Reetha, S., et al., "Screening of Cellulase and Pectinase by Using Pseudomonas fluorescence and Bacillus subtilis," 2014, International Letters of Natural Science, vol. 8, No. 2, pp. 75-80.
Sales, J., et al.,"Coffee (*Coffea arabica* L) Seeds Germination After Treatment with Different Concentrations and Embebding Times in Celluslase", Cienc. Agrotec. [online]. 2003, vol. 27, No. 3, pp. 557-564 ISSN 1413-7054. http://dx.doi.org/10.1590/S1413-70542003000300009, Abstract, 1 page.
Shani, et al., "Expression of Endo-1,4-beta-glucanase (cel1) in *Arabidopsis thaliana* is Associated with Plant Growth, Kylem Development and Cell Wall Thickening," Plant Cell Rep., 2006, vol. 10, pp. 1067-1074.
Shen, et al.,"Effect of Plant Growth-promoting Rhizobacteria (PGPRs) on Plant Growth, Yield, and Quality of Tomato (*Lycopersicon esculentum* Mill.) under Simulated Seawater Irrigation," J Gen Appl Microbial. 2012, vol. 58, pp. 253-262.
Singh, B. et al. "Microbial Phytases in Phosphorus Acquisition and Plant Growth Promotion," Apr.-Jun. 2011, Physiol. Mol. Biol. Plants, vol. 17, No. 2, pp. 93-103.
Stewart, G.C., et al., U.S. Appl. No. 14/849,123, filed Sep. 9, 2015, titled "Bacillus Based Delivery System and Methods of Use".
Stewart, G.C., et al., U.S. Appl. No. 14/849,295, filed Sep. 9, 2015, titled "Bacillus Based Delivery System and Methods of Use".
Tan,, L., et al., "Sequence Motifs and Proteolytic Cleavage of the Collagen-Like Glycoprotein BclA Required for Its Attachment to the Exosporium of Bacillus anthracis," Mar. 2010, Journal of Bacteriology, vol. 192, No. 5, pp. 1259-1268.
Thompson, B., et al., U.S. Appl. No. 14/213,525, filed Mar. 14, 2014, titled "Fusion Proteins and Methods for Stimulating Plant Growth, Protecting Plants from Pathogens, and Immobilizing Bacillus Spores on Plant Roots".
Thompson, B., et al., U.S. Appl. No. 14/775,892, filed Sep. 14, 2015, titled "Fusion Proteins and Methods for Stimulating Plant Growth, Protecting Plants, and Immobilizing Bacillus Spores on Plants".
Thompson, B., et al., U.S. Appl. No. 14/857,606, filed Sep. 17, 2015, titled "Fusion Proteins, Recombinant Bacteria, and Methods for Using Recombinant Bacteria".
Thompson, et al., U.S. Appl. No. 15/414,050, filed Jan. 24, 2017, titled "Fusion Proteins and Methods for Stimulating Plant Growth, Protecting Plants from Pathogens, and Immobilizing Bacillus Spores on Plant Roots."
U.S. Appl. No. 15/461,188.
Wang, et al.,"PLD: Phospholipase Ds in Plant Signaling," Springer, Phospholipases in Plant Signaling, Signaling and Communication in Plants, 2013, vol. 20, pp. 3-26.
U.S. Appl. No. 14/857,176, U.S. Appl. No. 62/051,911.
U.S. Appl. No. 15/511,835, PCT/US2015/050597, U.S. Appl. No. 62/051,915.
U.S. Appl. No. 15/511,844, PCT/US2015/050612, U.S. Appl. No. 62/051,919.
U.S. Appl. No. 15/511,839, PCT/US2015/050621, U.S. Appl. No. 62/051,932.
U.S. Appl. No. 15/511,854, PCT/US2015/050637, U.S. Appl. No. 62/051,933.

(56) References Cited

OTHER PUBLICATIONS

U.S. Appl. No. 15/511,864, PCT/US2015/050658, U.S. Appl. No. 62/051,935.
Pakula A. A. et al., "Genetic analysis of protein stability and function," Annual Review of Genetics, 1989, vol. 23, pp. 289-310.
Frankel A. E. et al., "Characterization of diphtheria fusion proteins targeted to the human interleukin-3 receptor," Protein Engineering, 2000, vol. 13, No. 8, pp. 575-581.

* cited by examiner

| | SEQ ID NO. | 20-35 % Identity | 25-35 % Identity |
|---|---|---|---|
| MSNNNYSNGLNPDESLSASA**AFDPNLVGPTLPPIPP**FTLPTG | 1 | 100% | 100% |
| MSEKYIILHGT**ALEPNLIGPTLPPIPP**FTFPNG | 3 | 81.3% | 90.9% |
| MVKVVEGNGGKSKIKSPLNSNF**KILSDLVGPTFPPVPT**GMTGIT | 5 | 50.0% | 72.7% |
| MKQNDKLWLDKG**IIGPENIGPTFPVLPP**IHIPTG | 7 | 43.8% | 54.5% |
| MDEFLSSA**ALNPGSVGPTLPPMQP**FQFRTG | 9 | 62.5% | 72.7% |
| MFDKNEIQKINGILQAN**ALNPNLIGPTLPPIPP**FTLPTG | 11 | 81.3% | 90.9% |
| MFDKNEMKKTNEVLQAN**ALDPNIIGPTLPPIPP**FTLPTG | 13 | 81.3% | 81.8% |
| MSRKDKFNRSRMSRKDRFNSPKIKSEI**SISPDLVGPTFPPIPS**FTLPTG | 15 | 62.5% | 81.8% |
| MNEEYSILHGP**ALEPNLIGPTLPSIPP**FTFPTG | 17 | 75.0% | 81.8% |
| MKNRDNNRKQNSLSSNF**RIPPELIGPTFPPVPT**GFTGIG | 19 | 50.0% | 63.6% |
| MSDKHQMKKISEVLQAH**ALDPNLIGPPLPPITP**FTFPTG | 21 | 75.0% | 72.7% |
| MDEFLSFA**ALNPGSIGPTLPPVPP**FQFPTG | 23 | 62.5% | 72.7% |
| MDEFLSST**ALNPCSIGPTLPPMQP**FQFPTG | 25 | 56.2% | 63.6% |
| MKERDRQNSLNSNF**RISPNLIGPTFPPVPT**GFTGIG | 27 | 56.2% | 63.6% |
| VFDKNEIQKINGILQAN**ALNPNLIGPTLPPIPP**FTLPTG | 29 | 81.3% | 90.9% |
| MDEFLYFA**ALNPGSIGPTLPPVQP**FQFPTG | 31 | 56.2% | 63.6% |
| **MDSKNIGPTFPPLPS**INFPTG | 33 | 43.8% | 54.5% |
| **MIGPENIGPTFPILPP**IYIPTG | 35 | 43.8% | 54.5% |
| MSNNNIPSPFFFN**NFNPELIGPTFPPIPP**LTLPTG | 43 | 68.8% | 81.8% |
| MFSEKKRKDLIPDNFLSAP**ALDPNLIGPTFPPIPS**FTLPTG | 45 | 75.0% | 72.7% |
| MTRKDKFNRSRISRRDRFNSPKIKSEI**LISPDLVGPTFPPIPS**FTLPTG | 47 | 62.5% | 81.8% |
| MSRKDRFNSPKIKSEI**SISPDLVGPTFPPIPS**FTLPTG | 49 | 62.5% | 81.8% |
| MKERDNKGKQHSLNSNF**RIPPELIGPTFPPVPT**GFTGIG | 51 | 50.0% | 63.6% |
| MRERDNKRQQHSLNPNF**RISPELIGPTFPPVPT**GFTGIG | 53 | 50.0% | 63.6% |
| MKNRDNKGKQQSNF**RIPPELIGPTFPPVPT**GFTGIG | 55 | 50.0% | 63.6% |
| MKFSKKSTVDSSIVGKRVVSKVNILRFYDARSCQDKDVDGFVDVGELFTIFRKLNMEGSVQFKAHNSI GKTYYITINEVYVFVTVLLQYSTLIGGSYVFDKNEIQKINGILQAN**ALNPNLIGPTLPPIPP**FTLPTG | 57 | 81.3% | 90.9% |

COMPOSITIONS COMPRISING RECOMBINANT *BACILLUS* CELLS AND ANOTHER BIOLOGICAL CONTROL AGENT

CROSS-REFERENCE TO RELATED APPLICATION(S)

The present application is a 35 U.S.C. § 371 national phase entry of PCT/US2015/050592, filed on Sep. 17, 2015, which claims priority to U.S. Provisional Patent Application No. 62/051,911, filed on Sep. 17, 2014, both of which are hereby incorporated by reference in their entirety.

REFERENCE TO SEQUENCE LISTING SUBMITTED ELECTRONICALLY

The official copy of the sequence listing is submitted electronically via EFS-Web as an ASCII-formatted sequence listing with a file named "BCS149057WO_ST25.txt" created on Sep. 14, 2015, and having a size of 152 kilobytes, and is filed concurrently with the specification. The sequence listing contained in this ASCII-formatted document is part of the specification and is herein incorporated by reference in its entirety.

BACKGROUND

Field of the Invention

The present invention relates to a composition comprising (i) recombinant exosporium-producing *Bacillus* cells that express a fusion protein comprising: (x) at least one plant growth stimulating protein or peptide; and (y) a targeting sequence that localizes the fusion protein to the exosporium of the *Bacillus* cells; and (ii) at least one further biological control agent selected from particular microorganisms disclosed herein and/or a mutant of a specific strain of a microorganism disclosed herein having all identifying characteristics of the respective strain, and/or at least one metabolite produced by the respective strain that exhibits the ability to improve plant growth and/or health and/or activity against insects, mites, nematodes and/or phytopathogens in a synergistically effective amounts. Furthermore, the present invention relates to the use of this composition as well as a method for enhancing plant growth, promoting plant health, and/or reducing overall damage of plants and plant parts.

Background of the Invention

In crop protection, there is a continuous need for applications that improve the health and/or the growth of plants. Healthier plants generally result in higher yields and/or better quality of a plant or its products.

In order to promote plant health, fertilizers are employed worldwide, based on both inorganic and organic substances. A fertilizer may be a single substance or a composition, and is used to provide nutrients to plants. A major breakthrough in the application of fertilizers was the development of nitrogen-based fertilizer by Justus von Liebig around 1840. Fertilizers, however, can lead to soil acidification and destabilization of nutrient balance in soil, including depletion of minerals and enrichment of salt and heavy metals. In addition, excessive fertilizer use can lead to alteration of soil fauna as well as contaminate surface water and ground water. Further, unhealthful substances such as nitrate may become enriched in plants and fruits.

In addition, insecticides and fungicide are employed worldwide to control pests. Synthetic insecticides or fungicides often are non-specific and therefore can act on organisms other than the target organisms, including other naturally occurring beneficial organisms. Because of their chemical nature, they may also be toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i.e., synthetic) pesticides. Thus, there is a need to manage food chain requirements while still allowing effective pest control.

A further problem arising with the use of synthetic insecticides or fungicides is that the repeated and exclusive application of an insecticide or fungicides often leads to selection of resistant animal pests or microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The use of biological control agents (BCAs) is an alternative to fertilizers and synthetic pesticides. In some cases, the effectiveness of BCAs is not at the same level as for fertilizers or for conventional insecticides and fungicides, especially in case of severe infection pressure. Consequently, in some circumstances, biological control agents, their mutants and metabolites produced by them are, in particular in low application rates, not entirely satisfactory. Thus, there is a constant need for developing new, alternative plant health-enhancing and/or plant protection agents which in some areas at least help to fulfill the above-mentioned requirements.

SUMMARY

In view of this, it was in particular an object of the present invention to provide compositions which have an enhanced ability to improve plant growth and/or to enhance plant health or which exhibit enhanced activity against insects, mites, nematodes and/or phytopathogens.

Accordingly, it was found that these objectives are achieved with the compositions according to the invention as defined in the following. By applying a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen or a pest; and (ii) a targeting sequence that localizes the fusion protein to the exosporium of the *Bacillus* cells; and b) at least one particular strain disclosed herein other than said recombinant *Bacillus* cells according to the invention, the ability to enhance preferably in a superadditive manner (i) plant growth, plant yield and/or plant health and/or (ii) the activity against insects, mites, nematodes and/or phytopathogens.

References herein to targeting sequences, exosporium proteins, exosporium protein fragments, fusion proteins, and recombinant exosporium producing *Bacillus* cells that express such fusion proteins should not be considered to be stand-alone embodiments. Instead, throughout the present application, references to the targeting sequences, exosporium proteins, exosporium protein fragments, fusion proteins, and recombinant exosporium producing *Bacillus* cells that express such fusion proteins should be considered to be disclosed and claimed only in combination (and preferably in a synergistic combination) with one or more of the particular biological control agents described herein. Furthermore, references to “the particular microorganisms disclosed herein” or “to the particular biological control agents described, or disclosed, herein” are intended to encompass the biological control agents and the microorganisms, including the strains, mutants and metabolites thereof, as described below under the heading “Synthetic Nodulation Factors and Plant Growth Stimulations”.

The present invention is directed to a composition comprising a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or a protein or peptide that protects a plant from a pathogen; and (ii) a targeting sequence that localizes the fusion protein to the exosporium of the *Bacillus* cells; and b) at least one further and different particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in synergistically effective amounts.

In some embodiments, the targeting sequence comprises an amino acid sequence having at least about 43% identity with amino acids 20-35 of SEQ ID NO: 1, wherein the identity with amino acids 25-35 is at least about 54%; a targeting sequence comprising amino acids 1-35 of SEQ ID NO: 1; a targeting sequence comprising amino acids 20-35 of SEQ ID NO: 1; a targeting sequence comprising amino acids 22-31 of SEQ ID NO: 1; a targeting sequence comprising amino acids 22-33 of SEQ ID NO: 1; a targeting sequence comprising amino acids 20-31 of SEQ ID NO: 1; a targeting sequence comprising SEQ ID NO: 1; or an exosporium protein comprising an amino acid sequence having at least 85% identity with SEQ ID NO: 2.

In other embodiments, the recombinant *Bacillus* cells are cells of a *Bacillus cereus* family member such as *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis* and combinations thereof. In a further embodiment, the recombinant *Bacillus* cells are cells of *Bacillus thuringiensis* BT013A.

In certain aspects, the fusion protein comprises an enzyme involved in the production or activation of a plant growth stimulating compound selected from the group consisting of an acetoin reductase, an indole-3-acetamide hydrolase, a tryptophan monooxygenase, an acetolactate synthetase, an $\alpha$-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a $\beta$-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a $\beta$-1,3-glucanase, a $\beta$-1,4-glucanase, a $\beta$-1,6-glucanase, an aminocyclopropane-1-carboxylic acid deaminase, and an enzyme involved in producing a nod factor.

In other aspects, the fusion protein comprises an enzyme that degrades or modifies a bacterial, fungal, or plant nutrient source selected from the group consisting of a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, and a siderophore.

In some embodiments, the fusion protein is expressed under the control of a sporulation promoter native to the targeting sequence, exosporium protein, or exosporium protein fragment of the fusion protein. The fusion protein may be expressed under the control of a high-expression sporulation promoter. In certain aspects, the high-expression sporulation promoter comprises a sigma-K sporulation-specific polymerase promoter sequence. In other aspects, the sporulation promoter comprises a nucleic acid sequence having at least 80% identity, at least 85% identity, at least 90% identity, at least 95% identity, at least 96% identity, at least 97% identity, at least 98% identity, or at least 99% identity with a nucleic acid sequence of any one of SEQ ID NOS: 85-103. In some embodiments, the sporulation promoter comprises a nucleic acid sequence having 100% identity with a nucleic acid sequence of any one of SEQ ID NOS: 85-103.

In other embodiments, the at least one biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., “*Bacillus* Lipopeptides: Versatile Weapons for Plant Disease Biocontrol,” Trends in Microbiology, Vol 16, No. 3, March 2008, pp. 115-125. *Bacillus* strains capable of producing lipopeptides include *Bacillus subtilis* QST713, *Bacillus amyloliquefaciens* strain D747 (available as BACSTAR® from Etec Crop Solutions, NZ and also available as DOUBLE NICKEL™ from Certis, US); *Bacillus subtilis* MBI600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 is available from Novozymes Biologicals Inc. (Salem, Va.) or Syngenta Crop Protection, LLC (Greensboro, N.C.) as the fungicide TAEGRO® or TAEGRO® ECO (EPA Registration No. 70127-5).

In still other embodiments, the at least one biological control agent is selected from the group consisting of *Bacillus pumilus* strain QST2808, *Bacillus subtilis* strain QST713, *Bacillus subtilis* strain QST30002, *Bacillus subtilis* strain QST30004, *Streptomyces microflavus* strain NRRL B-50550, *Streptomyces microflavus* strain M, *Bacillus firmus* strain I-1582, mutants thereof having all the identifying characteristics of the respective strains, and at least one metabolite produced by the respective strains that exhibits activity against insects, mites, nematodes and/or phytopathogens.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source; or a protein or peptide that protects a plant from a pathogen; and (ii) a targeting sequence that localizes the fusion protein to the exosporium of the *Bacillus* cells; and b) *Bacillus firmus* strain I-1582 in a synergistically effective amount.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or at least one protein or peptide that protects a plant from a pathogen; and (ii) a targeting sequence that localizes the fusion protein to the exosporium of the *Bacillus* cells; and b) *Bacillus subtilis* strain QST713 in a synergistically effective amount.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or at least one protein or peptide that protects a plant from a pathogen; and (ii) a targeting sequence that localizes the fusion protein to the exosporium of the *Bacillus* cells; and b) *Bacillus pumilus* strain QST2808 in a synergistically effective amount.

In yet other embodiments, the composition further comprises c) at least one fungicide and/or d) at least one insecticide. The at least one fungicide and/or the at least one insecticide may be synthetic. In one aspect of such embodiment, the biological control agent and additional insecticide of such composition comprise *Bacillus firmus* strain I-1582 and clothianidin, respectively.

In a particular aspect of the above embodiments (i) the biological control agent is *Bacillus subtilis* QST713 or mutants having all the identifying characteristics of the *Bacillus subtilis* QST713 and/or at least 95% or at least 98% sequence identity to *Bacillus subtilis* QST713; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% sequence identity to SEQ ID NO: 107, 108 and 109, respectively; and (iv) the recombinant *Bacillus cereus* family member cells comprise cells of *Bacillus thuringiensis* or *Bacillus mycoides*. In yet another particular embodiment, the recombinant *Bacillus cereus* family member cells are cells of *Bacillus thuringiensis* BT013A.

In a particular aspect of the above embodiments (i) the biological control agent is *Bacillus firmus* I-1582 or mutants having all the identifying characteristics of *Bacillus firmus* I-1582 and/or at least 95% or at least 98% sequence identity to *Bacillus firmus* I-1582; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% or at least 98% sequence identity to SEQ ID NO: 107, 108 and 109, respectively; and (iv) the recombinant *Bacillus cereus* family member cells comprise cells of *Bacillus thuringiensis* or *Bacillus mycoides*. In yet another particular embodiment, the recombinant *Bacillus cereus* family member cells are cells of *Bacillus thuringiensis* BT013A. In yet another aspect of this embodiment the composition further comprises clothianidin.

In a particular aspect of the above embodiments (i) the biological control agent is *Bacillus pumilus* QST2808 or mutants having all the identifying characteristics of *Bacillus pumilus* QST2808 and/or at least 95% or at least 98% sequence identity to *Bacillus pumilus* QST2808; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% or at least 98% sequence identity to SEQ ID NO: 107, 108 and 109, respectively; and (iv) the recombinant *Bacillus cereus* family member cells comprise the cells of *Bacillus thuringiensis* or *Bacillus mycoides*. In yet another particular embodiment, the recombinant *Bacillus cereus* family member cells are cells of *Bacillus thuringiensis* BT013A.

In some aspects, the composition further comprises at least one auxiliary selected from the group consisting of extenders, solvents, spontaneity promoters, carriers, emulsifiers, dispersants, frost protectants, thickeners and adjuvants.

In other aspects, the invention is directed to a seed treated with any of the compositions disclosed herein.

Furthermore, the present invention relates to use of the disclosed compositions as a fungicide and/or insecticide. In certain aspects, the disclosed compositions are used for reducing overall damage of plants and plant parts as well as losses in harvested fruits or vegetables caused by insects, mites, nematodes and/or phytopathogens. In other aspects, the disclosed compositions are used for enhancing plant growth and/or promoting plant health.

Additionally, the present invention is directed to a method of treating a plant, a plant part, such as a seed, root, rhizome, corm, bulb, or tuber, and/or a locus on which or near which the plant or the plant parts grow, such as soil, to enhance plant growth and/or promote plant health comprising the step of simultaneously or sequentially applying to a plant, a plant part and/or a plant loci: a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus* cells; and b) at least one biological control agent disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount.

In another embodiment, the present invention is a method for reducing overall damage of plants and plant parts as well as losses in harvested fruits or vegetables caused by insects, mites, nematodes and/or phytopathogens comprising the step of simultaneously or sequentially applying to a plant, a plant part, such as a seed, root, rhizome, corm, bulb, or tuber, and/or a locus on which or near which the plant or the plant parts grow, such as soil: a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus* cells; and b) at least one biological control agent disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount.

In the above paragraphs, the term "comprise" or any derivative thereof (e.g., comprising, comprises) may be replaced with "consist of" or the applicable corresponding derivative thereof.

BRIEF DESCRIPTION OF THE DRAWINGS

FIG. 1 shows an alignment of the amino acid sequence of the amino-terminal portion of *Bacillus anthracis* Sterne strain Bc1A and with the corresponding region from various exosporium proteins from *Bacillus cereus* family members.

DETAILED DESCRIPTION

In general "pesticidal" means the ability of a substance to increase mortality or inhibit the growth rate of plant pests. The term is used herein, to describe the property of a substance to exhibit activity against insects, mites, nematodes and/or phytopathogens. In the sense of the present invention the term "pests" include insects, mites, nematodes and/or phytopathogens.

As used herein, "biological control" is defined as control of a pathogen and/or insect and/or an acarid and/or a nematode by the use of a second organism. Known mechanisms of biological control include bacteria that control root rot by out-competing fungi for space or nutrients on the surface of the root. Bacterial toxins, such as antibiotics, have been used to control pathogens. The toxin can be isolated and applied directly to the plant or the bacterial species may be administered so it produces the toxin in situ. Other means of exerting biological control include the application of certain fungi producing ingredients active against a target phytopathogen, insect, mite or nematode, or attacking the target pest/pathogen. "Biological control" as used in connection with the present invention may also encompass microorganisms having a beneficial effect on plant health, growth, vigor, stress response or yield. Application routes include spray application, soil application and seed treatment.

The term "metabolite" refers to any compound, substance or byproduct of a fermentation of a said microorganism that has pesticidal, fungicidal or nematicidal activity or ability to enhance plant health or increase plant yield. The term "mutant" refers to a variant of the parental strain as well as methods for obtaining a mutant or variant in which the pesticidal activity is greater than that expressed by the parental strain. The "parent strain" is defined herein as the original strain before mutagenesis or the deposited strain. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art.

A "variant" is a strain having all the identifying characteristics of the NRRL or ATCC Accession Numbers as indicated in this text and can be identified as having a genome that hybridizes under conditions of high stringency to the genome of the NRRL or ATCC Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated NRRL or ATCC Accession Number may also be defined as a strain having a genomic sequence that is greater than 85%, more preferably greater than 90% or more preferably greater than 95% sequence identity to the genome of the indicated NRRL or ATCC Accession Number. A polynucleotide or polynucleotide region (or a polypeptide or polypeptide region) has a certain percentage (for example, 80%, 85%, 90%, 95%, 96%, 97%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987) Supplement 30, Section 7. 7. 18, Table 7. 7. 1.

NRRL is the abbreviation for the Agricultural Research Service Culture Collection, having the address National Center for Agricultural Utilization Research, Agricultural Research Service, U.S. Department of Agriculture, 1815 North University Street, Peoria, Ill. 61604, U.S.A.

ATCC is the abbreviation for the American Type Culture Collection, having the address ATCC Patent Depository, 10801 University Boulevard, Manassas, Va. 10110, U.S.A.

CNCM is the abbreviation for the Collection Nationale de Cultures de Microorganismes, Institute Pasteur, France, having the address of Institut Pasteur, 25 Rue du Docteur Roux, F-75724 Paris Cedex 15, France.

All strains described herein and having an accession number in which the prefix is NRRL, ATCC or CNCM have been deposited with the above-described respective depositary institution in accordance with the Budapest Treaty on the International Recognition of the Deposit of Microorganisms for the Purposes of Patent Procedure.

An "enzyme involved in the production or activation of a plant growth stimulating compound" includes any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure to an active or more active form of the compound. Such compounds include, for example, but are not limited to, small molecule plant hormones such as auxins and cytokinins, bioactive peptides, and small plant growth stimulating molecules synthesized by bacteria or fungi in the rhizosphere (e.g., 2,3-butanediol).

A "plant immune system enhancer protein or peptide" as used herein includes any protein or peptide that has a beneficial effect on the immune system of a plant.

The term "plant growth stimulating protein or peptide" as used herein includes any protein or peptide that increases plant growth in a plant exposed to the protein or peptide.

The terms "promoting plant growth" and "stimulating plant growth" are used interchangeably herein, and refer to the ability to enhance or increase at least one of the plant's height, weight, leaf size, root size, or stem size, to increase protein yield from the plant or to increase grain yield of the plant.

A "protein or peptide that protects a plant from a pathogen" as used herein includes any protein or peptide that makes a plant exposed to the protein or peptide less susceptible to infection with a pathogen.

A "protein or peptide that enhances stress resistance in a plant" as used herein includes any protein or peptide that makes a plant exposed to the protein or peptide more resistant to stress.

The term "plant binding protein or peptide" refers to any peptide or protein capable of specifically or non-specifically binding to any part of a plant (e.g., roots or aerial portions of a plant such as leaves foliage, stems, flowers, or fruits) or to plant matter.

The term "targeting sequence" as used herein refers to a polypeptide sequence that results in the localization of a longer polypeptide or the protein to the exosporium of a *Bacillus cereus* family member.

Recombinant Exosporium-Producing *Bacillus* Cells Expressing Fusion Proteins

The fusion proteins contain a targeting sequence, an exosporium protein, or an exosporium protein fragment that targets the fusion protein to the exosporium of a *Bacillus cereus* family member and: (a) a plant growth stimulating protein or peptide; (b) a protein or peptide that protects a plant from a pathogen; (c) a protein or peptide that enhances stress resistance of a plant; (d) a plant binding protein or peptide; or (e) a plant immune system enhancer protein or peptide. When expressed in *Bacillus cereus* family member bacteria, these fusion proteins are targeted to the exosporium layer of the spore and are physically oriented such that the protein or peptide is displayed on the outside of the spore.

This *Bacillus* exosporium display (BEMD) system can be used to deliver peptides, enzymes, and other proteins to plants (e.g., to plant foliage, fruits, flowers, stems, or roots) or to a plant growth medium such as soil. Peptides, enzymes, and proteins delivered to the soil or another plant growth medium in this manner persist and exhibit activity in the soil for extended periods of time. Introduction of recombinant exosporium-producing *Bacillus* cells expressing the fusion proteins described herein into soil or the rhizosphere of a plant leads to a beneficial enhancement of plant growth in many different soil conditions. The use of the BEMD to create these enzymes allows them to continue to exert their beneficial results to the plant and the rhizosphere over the first months of a plants life.

Targeting Sequences, Exosporium Proteins, and Exosporium Protein Fragments

For ease of reference, the SEQ ID NOS. for the peptide and protein sequences referred to herein are listed in Table 1 below.

TABLE 1

Peptide and Protein Sequences

| Protein, Protein Fragment, or Targeting Sequence | Sequence Identification Number |
|---|---|
| AA 1-41 of BclA (*B. anthracis* Sterne) | SEQ ID NO: 1* |
| Full length BclA | SEQ ID NO: 2* |
| AA 1-33 of BetA/BAS3290 (*B. anthracis* Sterne) | SEQ ID NO: 3 |
| Full length BetA/BAS3290 | SEQ ID NO: 4 |
| Met + AA 2-43 of BAS4623 (*B. anthracis* Sterne) | SEQ ID NO: 5 |
| Full length BAS4623 | SEQ ID NO: 6 |
| AA 1-34 of BclB (*B. anthracis* Sterne) | SEQ ID NO: 7 |
| Full length BclB | SEQ ID NO: 8 |
| AA 1-30 of BAS1882 (*B. anthracis* Sterne) | SEQ ID NO: 9 |
| Full length BAS1882 | SEQ ID NO: 10 |
| AA 1-39 of gene 2280 (*B. weihenstephensis* KBAB4) | SEQ ID NO: 11 |
| Full length KBAB4 gene 2280 | SEQ ID NO: 12 |
| AA 1-39 of gene 3572 (*B. weihenstephensis* KBAB4) | SEQ ID NO: 13 |
| Full Length KBAB4 gene 3572 | SEQ ID NO: 14 |
| AA 1-49 of Exosporium Leader Peptide (*B. cereus* VD200) | SEQ ID NO: 15 |
| Full Length Exosporium Leader Peptide | SEQ ID NO: 16 |
| AA 1-33 of Exosporium Leader Peptide (*B. cereus* VD166) | SEQ ID NO: 17 |
| Full Length Exosporium Leader Peptide | SEQ ID NO: 18 |
| AA 1-39 of hypothetical protein IKG_04663 (*B. cereus* VD200) | SEQ ID NO: 19 |
| Full Length hypothetical protein IKG_04663, partial | SEQ ID NO: 20 |
| AA 1-39 of YVTN β-propeller protein (*B. weihenstephensis* KBAB4) | SEQ ID NO: 21 |
| Full length YVTN β-propeller protein KBAB4 | SEQ ID NO: 22 |
| AA 1-30 of hypothetical protein bcerkbab4_2363 (*B. weihenstephensis* KBAB4) | SEQ ID NO: 23 |
| Full length hypothetical protein bcerkbab4_2363 KBAB4 | SEQ ID NO: 24 |
| AA 1-30 of hypothetical protein bcerkbab4_2131 (*B. weihenstephensis* KBAB4) | SEQ ID NO: 25 |
| Full length hypothetical protein bcerkbab4_2131 | SEQ ID NO: 26 |
| AA 1-36 of triple helix repeat containing collagen (*B. weihenstephensis* KBAB4) | SEQ ID NO: 27 |
| Full length triple helix repeat-containing collagen KBAB4 | SEQ ID NO: 28 |
| AA 1-39 of hypothetical protein bmyco0001_21660 (*B. mycoides* 2048) | SEQ ID NO: 29 |
| Full length hypothetical protein bmyco0001_21660 | SEQ ID NO: 30 |
| AA 1-30 of hypothetical protein bmyc0001_22540 (*B. mycoides* 2048) | SEQ ID NO: 31 |
| Full length hypothetical protein bmyc0001_22540 | SEQ ID NO: 32 |
| AA 1-21 of hypothetical protein bmyc0001_21510 (*B. mycoides* 2048) | SEQ ID NO: 33 |
| Full length hypothetical protein bmyc0001_21510 | SEQ ID NO: 34 |
| AA 1-22 of collagen triple helix repeat protein (*B. thuringiensis* 35646) | SEQ ID NO: 35 |
| Full length collagen triple helix repeat protein | SEQ ID NO: 36 |
| AA 1-35 of hypothetical protein WP_69652 (*B. cereus*) | SEQ ID NO: 43 |
| Full length hypothetical protein WP_69652 | SEQ ID NO: 44 |
| AA 1-41 of exosporium leader WP016117717 (*B. cereus*) | SEQ ID NO: 45 |

TABLE 1-continued

| Peptide and Protein Sequences | |
|---|---|
| Protein, Protein Fragment, or Targeting Sequence | Sequence Identification Number |
| Full length exosporium leader WP016117717 | SEQ ID NO: 46 |
| AA 1-49 of exosporium peptide WP002105192 (*B. cereus*) | SEQ ID NO: 47 |
| Full length exosporium peptide WP002105192 | SEQ ID NO: 48 |
| AA 1-38 of hypothetical protein WP87353 (*B. cereus*) | SEQ ID NO: 49 |
| Full length hypothetical protein WP87353 | SEQ ID NO: 50 |
| AA 1-39 of exosporium peptide 02112369 (*B. cereus*) | SEQ ID NO: 51 |
| Full length exosporium peptide 02112369 | SEQ ID NO: 52 |
| AA 1-39 of exosporium protein WP016099770 (*B. cereus*) | SEQ ID NO: 53 |
| Full length exosporium protein WP016099770 | SEQ ID NO: 54 |
| AA 1-36 of hypothetical protein YP006612525 (*B. thuringiensis*) | SEQ ID NO: 55 |
| Full length hypothetical protein YP006612525 | SEQ ID NO: 56 |
| AA 1-136 of hypothetical protein TIGR03720 (*B. mycoides*) | SEQ ID NO: 57** |
| Full length hypothetical protein TIGR03720 | SEQ ID NO: 58** |
| AA 1-196 of BclA (*B. anthracis* Sterne) | SEQ ID NO: 59* |
| Met + AA 20-35 of BclA (*B. anthracis* Sterne) | SEQ ID NO: 60 |
| Met + AA 12-27 of BetA/BAS3290 (*B. anthracis* Sterne) | SEQ ID NO: 61 |
| Met + AA 18-33 of gene 2280 (*B. weihenstephensis* KBAB4) | SEQ ID NO: 62 |
| Met + AA 18-33 of gene 3572 (*B. weihenstephensis* KBAB4) | SEQ ID NO: 63 |
| Met + AA 12-27 of Exosporium Leader Peptide (*B. cereus* VD166) | SEQ ID NO: 64 |
| Met + AA 18-33 of YVTN β-propeller protein (*B. weihenstephensis* KBAB4) | SEQ ID NO: 65 |
| Met + AA 9-24 of hypothetical protein bcerkbab4_2363 (*B. weihenstephensis* KBAB4) | SEQ ID NO: 66 |
| Met + AA 9-24 of hypothetical protein bcerkbab4_2131 (*B. weihenstephensis* KBAB4) | SEQ ID NO: 67 |
| Met + AA 9-24 of hypothetical protein bmyc0001_22540 (*B. mycoides* 2048) | SEQ ID NO: 68 |
| Met + AA 9-24 of BAS1882 (*B. anthracis* Sterne) | SEQ ID NO: 69 |
| Met + AA 20-35 of exosporium leader WP016117717 (*B. cereus*) | SEQ ID NO: 70 |
| Full length InhA (*B. mycoides*) | SEQ ID NO: 71 |
| Full length BAS1141 (ExsY) (*B. anthracis* Sterne) | SEQ ID NO: 72 |
| Full length BAS1144 (BxpB/ExsFA) (*B. anthracis* Sterne) | SEQ ID NO: 73 |
| Full length BAS1145 (CotY) (*B. anthracis* Sterne) | SEQ ID NO: 74 |
| Full length BAS1140 (*B. anthracis* Sterne) | SEQ ID NO: 75 |
| Full length ExsFB (*B. anthracis* H9401) | SEQ ID NO: 76 |
| Full length InhA1 (*B. thuringiensis* HD74) | SEQ ID NO: 77 |
| Full length ExsJ (*B. cereus* ATCC 10876) | SEQ ID NO: 78 |
| Full length ExsH (*B. cereus*) | SEQ ID NO: 79 |
| Full length YjcA (*B. anthracis* Ames) | SEQ ID NO: 80 |
| Full length YjcB (*B. anthracis*) | SEQ ID NO: 81 |
| Full length BclC (*B. anthracis* Sterne) | SEQ ID NO: 82 |
| Full length acid phosphatase (*Bacillus thuringiensis* serovar konkukian str. 97-27) | SEQ ID NO: 83 |
| Full length InhA2 (*B. thuringiensis* HD74) | SEQ ID NO: 84 |

AA = amino acids

**B. anthracis* Sterne strain BclA has 100% sequence identity with *B. thuringiensis* BclA. Thus, SEQ ID NOS: 1, 2, and 59 also represent amino acids 1-41 of *B. thuringiensis* BclA, full length *B. thuringiensis* BclA, and amino acids 1-196 of *B. thuringiensis* BclA, respectively. Likewise, SEQ ID NO: 60 also represents a methionine residue plus amino acids 20-35 of *B. thuringiensis* BclA.

***B. mycoides* hypothetical protein TIGR03720 has 100% sequence identity with *B. mycoides* hypothetical protein WP003189234. Thus, SEQ ID NOs: 57 and 58 also represent amino acids 1-136 of *B. mycoides* hypothetical protein WP003189234 and full length *B. mycoides* hypothetical protein WP003189234, respectively.

*Bacillus* is a genus of rod-shaped bacteria. The *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus toyoiensis* and *Bacillus weihenstephensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein Bc1A, while the basal layer is comprised of a number of different proteins. Another collagen-related protein, Bc1B, is also present in the exosporium and exposed on endospores of *Bacillus cereus* family members.

Bc1A, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of Bc1A and Bc1B could be used to target a peptide or protein to the exosporium of a *Bacillus cereus* endospore (see U.S. Patent Publication Nos. 2010/0233124 and 2011/0281316, and Thompson, et al., "Targeting of the Bc1A and Bc1B Proteins to the *Bacillus anthracis* Spore Surface," Molecular Microbiology, 70(2):421-34 (2008), the entirety of each of which is hereby incorporated by reference). It was also found that the BetA/BAS3290 protein of *Bacillus anthracis* localized to the exosporium.

In particular, amino acids 20-35 of Bc1A from *Bacillus anthracis* Sterne strain have been found to be sufficient for targeting to the exosporium. A sequence alignment of amino acids 1-41 of Bc1A (SEQ ID NO: 1) with the corresponding N-terminal regions of several other *Bacillus cereus* family exosporium proteins and *Bacillus cereus* family proteins having related sequences is shown in FIG. 1. As can be seen from FIG. 1, there is a region of high-homology among all of the proteins in the region corresponding to amino acids 20-41 of Bc1A. However, in these sequences, the amino acids corresponding to amino acids 36-41 of Bc1A contain secondary structure and are not necessary for fusion protein localization to the exosporium. The conserved targeting sequence region of Bc1A (amino acids 20-35 of SEQ ID NO: 1) is shown in bold in FIG. 1 and corresponds to the minimal targeting sequence needed for localization to the exosporium. A more highly conserved region spanning amino acids 25-35 of Bc1A within the targeting sequence is underlined in the sequences in FIG. 1, and is the recognition sequence for ExsFA/BxpB/ExsFB and homologs, which direct and assemble the described proteins on the surface of the exosporium The amino acid sequences of SEQ ID NOS: 3, 5, and 7 in FIG. 1 are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIG. 1, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of *Bacillus cereus* exosporium peptide 02112369, SEQ ID NO: 53 is amino acids 1-39 of *Bacillus cereus* exosporium protein WP016099770, SEQ ID NO: 55 is amino acids 1-36 of *Bacillus thuringiensis* hypothetical protein YP006612525, and SEQ ID NO: 57 is amino acids 1-136 of *Bacillus mycoides* hypothetical protein TIGR03720. As shown in FIG. 1, each of the N-terminal regions of these proteins contains a region that is conserved with amino acids 20-35 of BclA (SEQ ID NO: 1), and a more highly conserved region corresponding to amino acids 25-35 of BclA.

Any portion of BclA which includes amino acids 20-35 can be used as the targeting sequence. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2) or a midsized fragment of BclA that lacks the carboxy-terminus such as SEQ ID NO: 59 (amino acids 1-196 of BclA) can be used to target the fusion proteins to the exosporium. Midsized fragments such as the fragment of SEQ ID NO: 59 have less secondary structure than full length BclA and have been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 60 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663, *B. weihenstephensis* KBAB4 YVTN β-propeller protein, *B. weihenstephensis* KBAB4 hypothetical protein bcerkbab4_2363, *B. weihenstephensis* KBAB4 hypothetical protein bcerkbab4_2131, *B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, *B. thuringiensis* 35646 collagen triple helix repeat protein, *B. cereus* hypothetical protein WP_69652, *B. cereus* exosporium leader WP016117717, *B. cereus* exosporium peptide WP002105192, *B. cereus* hypothetical protein WP87353, *B. cereus* exosporium peptide 02112369, *B. cereus* exosporium protein WP016099770, *B. thuringiensis* hypothetical protein YP006612525, or *B. mycoides* hypothetical protein TIGR03720, which includes the amino acids corresponding to amino acids 20-35 of BclA can serve as the targeting sequence. As can be seen from FIG. 1, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, amino acids 1-16 of *B. thuringiensis* 35646 collagen triple helix repeat protein, amino acids 14-29 of *B. cereus* hypothetical protein WP_69652, amino acids 20-35 of *B. cereus* exosporium leader WP016117717, amino acids 28-43 of *B. cereus* exosporium peptide WP002105192, amino acids 17-32 of *B. cereus* hypothetical protein WP87353, amino acids 18-33 of *B. cereus* exosporium peptide 02112369, amino acids 18-33 of *B. cereus* exosporium protein WP016099770, amino acids 15-30 of *B. thuringiensis* hypothetical protein YP006612525, and amino acids 115-130 of *B. mycoides* hypothetical protein TIGR03720 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids can serve as the targeting sequence.

Thus, the targeting sequence can comprise amino acids 1-35 of SEQ ID NO: 1, amino acids 20-35 of SEQ ID NO: 1, SEQ ID NO: 1, SEQ ID NO: 60, amino acids 22-31 of SEQ ID NO: 1, amino acids 22-33 of SEQ ID NO: 1, or amino acids 20-31 of SEQ ID NO: 1. Alternatively, the targeting sequence consists of amino acids 1-35 of SEQ ID NO: 1, amino acids 20-35 of SEQ ID NO: 1, SEQ ID NO: 1, or SEQ ID NO: 60. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 59 (amino acids 1-196 of BclA). Alternatively, the exosporium protein fragment can consist of SEQ ID NO: 59.

The targeting sequence can also comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 61. The targeting sequence can also comprise amino acids 14-23 of SEQ ID NO: 3, amino acids 14-25 of SEQ ID NO: 3, or amino acids 12-23 of SEQ ID NO: 3.

The targeting sequence can also comprise amino acids 1-38 of SEQ ID NO: 5, amino acids 23-38 of SEQ ID NO: 5, or SEQ ID NO: 5, or the exosporium protein can comprise full length BAS4623 (SEQ ID NO: 6).

Alternatively, the targeting sequence can comprise amino acids 1-28 of SEQ ID NO: 7, amino acids 13-28 of SEQ ID NO: 7, or SEQ ID NO: 7, or the exosporium protein can comprise full length BclB (SEQ ID NO: 8).

The targeting sequence can also comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can also be used as a targeting sequence. Thus, the targeting sequence can comprise SEQ ID NO: 69.

The targeting sequence can also comprise amino acids 1-33 of SEQ ID NO:11, amino acids 18-33 of SEQ ID NO: 11, or SEQ ID NO: 11, or the exosporium protein can comprise the full length *B. weihenstephensis* KBAB4 2280 gene product (SEQ ID NO: 12). A methionine residue linked to amino acids 18-33 of the *B. weihenstephensis* KBAB4 2280 gene product can also be used as a targeting sequence. Thus, the targeting sequence can comprise SEQ ID NO: 62.

The targeting sequence can also comprise amino acids 1-33 of SEQ ID NO: 13, amino acids 18-33 of SEQ ID NO: 13, or SEQ ID NO:13, or the exosporium protein can comprise the full length *B. weihenstephensis* KBAB4 3572 gene product (SEQ ID NO:14). A methionine residue linked to amino acids 18-33 of the *B. weihenstephensis* KBAB4 3572 gene product can also be used as a targeting sequence. Thus, the targeting sequence can comprise SEQ ID NO: 63.

Alternatively, the targeting sequence can comprise amino acids 1-43 of SEQ ID NO: 15, amino acids 28-43 of SEQ ID NO: 15, or SEQ ID NO: 15, or the exosporium protein can comprise full length *B. cereus* VD200 exosporium leader peptide (SEQ ID NO: 16).

The targeting sequence can also comprise amino acids 1-27 of SEQ ID NO: 17, amino acids 12-27 of SEQ ID NO: 17, or SEQ ID NO: 17, or the exosporium protein can comprise full-length *B. cereus* VD166 exosporium leader peptide (SEQ ID NO: 18). A methionine residue linked to amino acids 12-27 of the *B. cereus* VD166 exosporium leader peptide can also be used as a targeting sequence. Thus, the targeting sequence can comprise SEQ ID NO: 64.

The targeting sequence can also comprise amino acids 1-33 of SEQ ID NO: 19, amino acids 18-33 of SEQ ID NO: 19, or SEQ ID NO: 19, or the exosporium protein can comprise full length *B. cereus* VD200 hypothetical protein IKG_04663 (SEQ ID NO: 20).

Alternatively, the targeting sequence comprises amino acids 1-33 of SEQ ID NO: 21, amino acids 18-33 of SEQ ID NO: 21, or SEQ ID NO: 21, or the exosporium protein can comprise full length *B. weihenstephensis* KBAB4 YVTN β-propeller protein (SEQ ID NO: 22). A methionine residue linked to amino acids 18-33 of the *B. weihenstephensis* KBAB4 YVTN β-propeller protein can also be used as a targeting sequence. Thus, the targeting sequence can comprise SEQ ID NO: 65.

The targeting sequence can also comprise amino acids 1-24 of SEQ ID NO: 23, amino acids 9-24 of SEQ ID NO: 23, or SEQ ID NO: 23, or the exosporium protein can comprise full length *B. weihenstephensis* KBAB4 hypothetical protein bcerkbab4_2363 (SEQ ID NO: 24). A methionine residue linked to amino acids 9-24 of *B. weihenstephensis* KBAB4 hypothetical protein bcerkbab4_2363 can also be used as a targeting sequence. Thus, the targeting sequence can comprise SEQ ID NO: 66.

The targeting sequence comprise amino acids 1-24 of SEQ ID NO: 25, amino acids 9-24 of SEQ ID NO: 25, or SEQ ID NO: 25, or the exosporium protein can comprise full length *B. weihenstephensis* KBAB4 hypothetical protein bcerkbab4_2131 (SEQ ID NO: 26). A methionine residue linked to amino acids 9-24 of *B. weihenstephensis* KBAB4 hypothetical protein bcerkbab4_2131 can also be used as a targeting sequence. Thus, the targeting sequence can comprise SEQ ID NO: 67.

Alternatively, the targeting sequence comprises amino acids 1-30 of SEQ ID NO: 27, amino acids 15-30 of SEQ ID NO: 27, or SEQ ID NO: 27, or the exosporium protein can comprise full length *B. weihenstephensis* KBAB4 triple helix repeat containing collagen (SEQ ID NO: 28).

The targeting sequence can also comprise amino acids 1-33 of SEQ ID NO: 29, amino acids 18-33 of SEQ ID NO: 29, or SEQ ID NO: 29, or the exosporium protein can comprise full length *B. mycoides* 2048 hypothetical protein bmyco0001_21660 (SEQ ID NO:30).

The targeting sequence can also comprise amino acids 1-24 of SEQ ID NO: 31, amino acids 9-24 of SEQ ID NO: 31, or SEQ ID NO:31, or the exosporium protein can comprise full length *B. mycoides* 2048 hypothetical protein bmyc0001_22540 (SEQ ID NO:32). A methionine residue linked to amino acids 9-24 of *B. mycoides* 2048 hypothetical protein bmyc0001_22540 can also be used as a targeting sequence. Thus, the targeting sequence can comprise SEQ ID NO: 68.

Alternatively, the targeting sequence comprises amino acids 1-15 of SEQ ID NO: 33, SEQ ID NO: 33, or the exosporium protein comprises full length *B. mycoides* 2048 hypothetical protein bmyc0001_21510 (SEQ ID NO: 34).

The targeting sequence can also comprise amino acids 1-16 of SEQ ID NO: 35, SEQ ID NO: 35, or the exosporium protein can comprise full length *B. thuringiensis* 35646 collagen triple helix repeat protein (SEQ ID NO:36).

The targeting sequence can comprise amino acids 1-29 of SEQ ID NO: 43, amino acids 14-29 of SEQ ID NO: 43, or SEQ ID NO: 43, or the exosporium protein can comprise full length *B. cereus* hypothetical protein WP_69652 (SEQ ID NO: 44).

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can also be used as a targeting sequence. Thus, the targeting sequence can comprise SEQ ID NO: 70.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can also comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGR03720 (SEQ ID NO: 58).

In addition, it can readily be seen from the sequence alignment in FIG. 1 that while amino acids 20-35 of Bc1A are conserved, and amino acids 25-35 are more conserved, some degree of variation can occur in this region without affecting the ability of the targeting sequence to target a protein to the exosporium. FIG. 1 lists the percent identity of each of corresponding amino acids of each sequence to amino acids 20-35 of Bc1A ("20-35% Identity") and to amino acids 25-35 of Bc1A ("25-35% Identity"). Thus, for example, as compared to amino acids 20-35 of Bc1A, the corresponding amino acids of BetA/BAS3290 are about 81.3% identical, the corresponding amino acids of BAS4623 are about 50.0% identical, the corresponding amino acids of Bc1B are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIG. 1.

With respect to amino acids 25-35 of Bc1A, the corresponding amino acids of BetA/BAS3290 are about 90.9% identical, the corresponding amino acids of BAS4623 are about 72.7% identical, the corresponding amino acids of Bc1B are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIG. 1.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence consisting of 16 amino acids and having at least about 62% identity with amino acids 20-35 of SEQ ID NO: 1, wherein the identity with amino acids 25-35 of SEQ ID NO:1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprise an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 81%.

The targeting sequence can also comprise an amino acid sequence having at least about 81% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of Bc1A, the corresponding amino acids of BetA/BAS3290, BAS4263, Bc1B, BAS1882, the KBAB4 2280 gene product, or the KBAB 3572 gene product, or a sequence comprising any of the above noted sequence identities to amino acids 20-35 and 25-35 of Bc1A is present.

It has further been discovered that certain *Bacillus cereus* family exosporium proteins which lack regions having homology to amino acids 25-35 of Bc1A can also be used to target a peptide or protein to the exosporium of a *Bacillus cereus* family member. In particular, the fusion proteins can comprise an exosporium protein comprising SEQ ID NO: 71 (*B. mycoides* InhA), an exosporium protein comprising SEQ ID NO: 72 (*B. anthracis* Sterne BAS1141 (ExsY)), an exosporium protein comprising SEQ ID NO: 73 (*B. anthracis* Sterne BAS1144 (BxpB/ExsFA)), an exosporium protein comprising SEQ ID NO: 74 (*B. anthracis* Sterne BAS1145 (CotY)), an exosporium protein comprising SEQ ID NO: 75 (*B. anthracis* Sterne BAS1140), an exosporium protein comprising SEQ ID NO: 76 (*B. anthracis* H9401 ExsFB), an exosporium protein comprising SEQ ID NO: 77 (*B. thuringiensis* HD74 InhA1), an exosporium protein comprising SEQ ID NO: 78 (*B. cereus* ATCC 10876 ExsJ), an exosporium protein comprising SEQ ID NO: 79 (*B. cereus* ExsH), an exosporium protein comprising SEQ ID NO: 80 (*B. anthracis* Ames YjcA), an exosporium protein comprising SEQ ID NO: 81 (*B. anthracis* YjcB), an exosporium protein comprising SEQ ID NO: 82 (*B. anthracis* Sterne Bc1C), an exosporium protein comprising SEQ ID NO: 83 (*Bacillus thuringiensis* serovar konkukian str. 97-27 acid phosphatase), or an exosporium protein comprising SEQ ID NO: 84 (*B. thuringiensis* HD74 InhA2). Inclusion of an exosporium protein comprising SEQ ID NO: 71, 72, 73, 74, 75, 76, 77, 78, 79, 80, 81, 82, 83, or 84 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein comprising an amino acid sequence having at least 85% identity with any one of SEQ ID NOS: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84. Alternatively, the fusion protein can comprise an exosporium protein having at least 90%, at least 95%, at least 98%, at least 99%, or 100% identity with any one of SEQ ID NOS: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84.

Alternatively, the fusion protein can comprise an exosporium protein fragment consisting of an amino acid sequence having at least 85% identity with SEQ ID NO: 59. Alternatively, the fusion protein can comprise an exosporium protein fragment consisting of an amino acid sequence having at least 90%, at least 95%, at least 98%, at least 99%, or 100% identity with SEQ ID NO: 59.

In any of the targeting sequences, exosporium proteins, or exosporium protein fragments described herein, the targeting sequence, exosporium protein, or exosporium protein fragment can comprise the amino acid sequence GXT at its carboxy terminus, wherein X is any amino acid.

In any of the targeting sequences, exosporium proteins, and exosporium protein fragments described herein, the targeting sequence, exosporium protein, or exosporium protein fragment, can comprise an alanine residue at the position of the targeting sequence that corresponds to amino acid 20 of SEQ ID NO: 1.

Fusion Proteins

The fusion proteins can comprise a targeting sequence, an exosporium protein, or an exosporium protein fragment, and at least one plant growth stimulating protein or peptide. The plant growth stimulating protein or peptide can comprise a peptide hormone, a non-hormone peptide, an enzyme involved in the production or activation of a plant growth stimulating compound or an enzyme that degrades or modifies a bacterial, fungal, or plant nutrient source. The targeting sequence, exosporium protein, or exosporium protein fragment can be any of the targeting sequences, exosporium proteins, or exosporium protein fragments described above.

The fusion proteins can comprise a targeting sequence, an exosporium protein, or an exosporium protein fragment, and at least one protein or peptide that protects a plant from a pathogen. The targeting sequence, exosporium protein, or exosporium protein fragment can be any of the targeting sequences, exosporium proteins, or exosporium protein fragments described above.

The fusion protein can be made using standard cloning and molecular biology methods known in the art. For example, a gene encoding a protein or peptide (e.g., a gene encoding a plant growth stimulating protein or peptide) can be amplified by polymerase chain reaction (PCR) and ligated to DNA coding for any of the above-described targeting sequences to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. The DNA encoding the fusion protein is suitably under the control of a sporulation promoter which will cause expression of the fusion protein on the exosporium of a *B. cereus* family member endospore (e.g., a native bc1A promoter from a *B. cereus* family member). Alternatively, DNA coding for the fusion protein can be integrated into the chromosomal DNA of the *B. cereus* family member host.

The fusion protein can also comprise additional polypeptide sequences that are not part of the targeting sequence, exosporium protein, exosporium protein fragment, or the plant growth stimulating protein or peptide, the protein or peptide that protects a plant from a pathogen, the protein or peptide that enhances stress resistance in a plant, or the plant binding protein or peptide. For example, the fusion protein can include tags or markers to facilitate purification or visualization of the fusion protein (e.g., a polyhistidine tag or a fluorescent protein such as GFP or YFP) or visualization of recombinant exosporium-producing *Bacillus* cells spores expressing the fusion protein.

Expression of fusion proteins on the exosporium using the targeting sequences, exosporium proteins, and exosporium protein fragments described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, and the fusion partner protein.

Thus, any of the fusion proteins described herein can comprise an amino acid linker between the targeting sequence, the exosporium protein, or the exosporium protein fragment and the plant growth stimulating protein or peptide, the protein or peptide that protects a plant from a pathogen, the protein or peptide that enhances stress resistance in a plant, or the plant binding protein or peptide.

The linker can comprise a polyalanine linker or a polyglycine linker. A linker comprising a mixture of both alanine and glycine residues can also be used. For example, where the targeting sequence comprises SEQ ID NO: 1, a fusion protein can have one of the following structures:

No linker: SEQ ID NO: 1—Fusion Partner Protein

Alanine Linker: SEQ ID NO: 1—An—Fusion Partner Protein

Glycine Linker: SEQ ID NO: 1—Gn—Fusion Partner Protein

Mixed Alanine and Glycine Linker: SEQ ID NO: 1—(A/G)n—Fusion Partner Protein where An, Gn, and (A/G)n are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "Fusion Partner Protein" represents the plant growth stimulating protein or peptide, the protein or peptide that protects a plant from a pathogen, the protein or peptide that enhances stress resistance in a plant, or the plant binding protein or peptide.

Alternatively or in addition, the linker can comprise a protease recognition site. Inclusion of a protease recognition site allows for targeted removal, upon exposure to a protease that recognizes the protease recognition site, of the plant growth stimulating protein or peptide, the protein or peptide that protects a plant from a pathogen, the protein or peptide that enhances stress resistance in a plant, or the plant binding protein or peptide.

Plant Growth Stimulating Proteins and Peptides

As noted above, the fusion proteins can comprise a targeting sequence, exosporium protein, or exosporium protein fragment and at least one plant growth stimulating protein or peptide. For example, the plant growth stimulating protein or peptide can comprise a peptide hormone, a non-hormone peptide, an enzyme involved in the production or activation of a plant growth stimulating compound, or an enzyme that degrades or modifies a bacterial, fungal, or plant nutrient source.

For example, where the plant growth stimulating protein or peptide comprises a peptide hormone, the peptide hormone can comprise a phytosulfokine (e.g., phytosulfokine-α), clavata 3 (CLV3), systemin, Zm1GF, or a SCR/SP11.

Where the plant growth stimulating protein or peptide comprises a non-hormone peptide, the non-hormone peptide can comprise a RKN 16D10, Hg-Syv46, an eNOD40 peptide, melittin, mastoparan, Mas7, RHPP, POLARIS, or kunitz trypsin inhibitor (KTI).

The plant growth stimulating protein or peptide can comprise an enzyme involved in the production or activation of a plant growth stimulating compound. The enzyme involved in the production or activation of a plant growth stimulating compound can be any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure into an active or more active form of the compound.

The plant growth stimulating compound can comprise a compound produced by bacteria or fungi in the rhizosphere, e.g., 2,3-butanediol.

Alternatively, the plant growth stimulating compound can comprise a plant growth hormone, e.g., a cytokinin or a cytokinin derivative, ethylene, an auxin or an auxin derivative, a gibberellic acid or a gibberellic acid derivative, abscisic acid or an abscisic acid derivative, or a jasmonic acid or a jasmonic acid derivative.

Where the plant growth stimulating compound comprises a cytokinin or a cytokinin derivative, the cytokinin or the cytokinin derivative can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin, trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof.

Where the plant growth stimulating compound comprises an auxin or an auxin derivative, the auxin or the auxin derivative can comprise an active auxin, an inactive auxin, a conjugated auxin, a naturally occurring auxin, or a synthetic auxin, or a combination thereof. For example, the auxin or auxin derivative can comprise indole-3-acetic acid, indole-3-pyruvic acid, indole-3-acetaldoxime, indole-3-acetamide, indole-3-acetonitrile, indole-3-ethanol, indole-3-pyruvate, indole-3-acetaldoxime, indole-3-butyric acid, a phenylacetic acid, 4-chloroindole-3-acetic acid, a glucose-conjugated auxin, or a combination thereof.

The enzyme involved in the production or activation of a plant growth stimulating compound can comprise an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase (e.g., tryptophan aminotransferase), a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosinase, a chitinase, a β-1,3-glucanase, a β-1,4-glucanase, a β-1,6-glucanase, an aminocyclopropane-1-carboxylic acid deaminase, or an enzyme involved in producing a nod factor (e.g., nodA, nodB, or nodI).

Where the enzyme comprises a protease or peptidase, the protease or peptidase can be a protease or peptidase that cleaves proteins, peptides, proproteins, or preproproteins to create a bioactive peptide. The bioactive peptide can be any peptide that exerts a biological activity.

Examples of bioactive peptides include RKN 16D10 and RHPP.

The protease or peptidase that cleaves proteins, peptides, proproteins, or preproproteins to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The protease or peptidase can cleave proteins in a protein-rich meal (e.g., soybean meal or yeast extract).

The plant growth stimulating protein can also comprise an enzyme that degrades or modifies a bacterial, fungal, or plant nutrient source. Such enzymes include cellulases, lipases, lignin oxidases, proteases, glycoside hydrolases, phosphatases, nitrogenases, nucleases, amidases, nitrate reductases, nitrite reductases, amylases, ammonia oxidases, ligninases, glucosidases, phospholipases, phytases, pectinases, glucanases, sulfatases, ureases, xylanases, and siderophores. When introduced into a plant growth medium or applied to a plant, seed, or an area surrounding a plant or a plant seed, fusion proteins comprising enzymes that degrade or modify a bacterial, fungal, or plant nutrient source can aid in the processing of nutrients in the vicinity of the plant and result in enhanced uptake of nutrients by the plant or by beneficial bacteria or fungi in the vicinity of the plant.

Suitable cellulases include endocellulases (e.g., an endogluconase such as a *Bacillus subtilis* endoglucanase, a *Bacillus thuringiensis* endoglucanase, a *Bacillus cereus* endoglucanase, or a *Bacillus clausii* endoglucanase), exocellulases (e.g., a *Trichoderma reesei* exocellulase), and β-glucosidases (e.g., a *Bacillus subtilis* β-glucosidase, a *Bacillus thuringiensis* β-glucosidase, a *Bacillus cereus* β-glucosidase, or a *Bacillus clausii* β-glucosidase).

The lipase can comprise a *Bacillus subtilis* lipase, a *Bacillus thuringiensis* lipase, a *Bacillus cereus* lipase, or a *Bacillus clausii* lipase.

In one embodiment, the lipase comprises a *Bacillus subtilis* lipase. The *Bacillus subtilis* lipase can be PCR amplified using the following primers: ggatccatggctgaacacaatcc (forward, SEQ ID NO: 37) and ggatccttaattcgtattctggcc (reverse, SEQ ID NO: 38).

In another embodiment, the cellulase is a *Bacillus subtilis* endoglucanase. The *Bacillus subtilis* endoglucanase can be PCR amplified using the following primers: ggatccatgaaacggtcaatc (forward, SEQ ID NO: 39) and ggatccttactaatttggttctgt (reverse, SEQ ID NO: 40).

In yet another embodiment, the fusion protein comprises an *E. coli* protease PtrB. The *E. coli* protease PtrB can be PCR amplified using the following primers: ggatccatgctaccaaaagcc (forward, SEQ ID NO: 41) and ggatccttagtccgcaggcgtagc (reverse, SEQ ID NO: 42).

In certain embodiments, the fusion protein contains an endoglucanase which derives from the nucleotide sequence in SEQ ID NO: 104.

The amino acid sequence for an exemplary endoglucanase that may be fused to the targeting sequence, an exosporium protein, or an exosporium protein fragment and, optionally, a linker sequence, such as a poly-A linker, is the fusion protein provided as SEQ ID NO: 107.

In other embodiments, the fusion protein contains a phospholipase that derives from the nucleotide sequence set forth in SEQ ID NO: 105.

The amino acid sequence for an exemplary phospholipase that may be fused to the targeting sequence, an exosporium protein, or an exosporium protein fragment and, optionally, a linker sequence, such as a poly-A linker, is the fusion protein provided as SEQ ID NO: 108.

In still other embodiments, the fusion protein contains a chitosanase that derives from the nucleotide sequence set forth in SEQ ID NO: 106. The amino acid sequence for an exemplary chitosanase that may be fused to the targeting sequence, an exosporium protein, or an exosporium protein fragment and, optionally, a linker sequence, such as a poly-A linker, in the fusion protein is provided as SEQ ID NO: 109.

To create fusion constructs, genes may be fused to the native bc1A promoter of *Bacillus thuringiensis* DNA encoding the first 35 amino acids of Bc1A (amino acids 1-35 of SEQ ID NO: 1) using the splicing by overlapping extension (SOE) technique. Correct amplicons are cloned into the *E. coli/Bacillus* shuttle vector pIIP13, and correct clones screened by DNA sequencing. Correct clones are electroporated into *Bacillus thuringiensis* (Cry-, plasmid-) and screened for chloramphenicol resistance. Correct transformants are grown in brain heart infusion broth overnight at 30° C., plated onto nutrient agar plates, and incubated at 30° C. for 3 days. Spores expressing the fusion construct (BEMD spores) may be collected off of the plates by washing in phosphate buffered saline (PBS) and purified by centrifugation and additional washes in PBS.

In such fusion proteins, the endoglucanase, phospholipase or chitosinase can comprise a nucleotide sequence encoding an amino acid sequence having at least 85% identity with SEQ ID NO: 107, 108 or 109, respectively.

In such fusion proteins, the endoglucanase, phospholipase or chitosinase can comprise an amino acid sequence having at least 90% identity with SEQ ID NO: 107, 108 or 109, respectively.

In such fusion proteins, the endoglucanase, phospholipase or chitosinase can comprise an amino acid sequence having at least 95% identity with SEQ ID NO: 107, 108 or 109, respectively.

In such fusion proteins, the endoglucanase, phospholipase or chitosinase can comprise an amino acid sequence having at least 98% identity with SEQ ID NO: 107, 108 or 109, respectively.

In such fusion proteins, the endoglucanase, phospholipase or chitosinase can comprise an amino acid sequence having at least 99% identity with SEQ ID NO: 107, 108 or 109, respectively.

Suitable lignin oxidases comprise lignin peroxidases, laccases, glyoxal oxidases, ligninases, and manganese peroxidases.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

The phosphatase can comprise a phosphoric monoester hydrolase, a phosphomonoesterase (e.g., PhoA4), a phosphoric diester hydrolase, a phosphodiesterase, a triphosphoric monoester hydrolase, a phosphoryl anhydride hydrolase, a pyrophosphatase, a phytase (e.g., *Bacillus subtilis* EE148 phytase or *Bacillus thuringiensis* BT013A phytase), a trimetaphosphatase, or a triphosphatase.

The nitrogenase can comprise a Nif family nitrogenase (e.g., *Paenibacillus massiliensis* NifBDEHKNXV).

Proteins and Peptides that Protects Plants from Pathogens

The fusion proteins can comprise a targeting sequence, exosporium protein, or exosporium protein fragment, and at least one protein or peptide that protects a plant from a pathogen.

The protein or peptide can comprise a protein or peptide that stimulates a plant immune response. For example, the protein or peptide that stimulates a plant immune response can comprise a plant immune system enhancer protein or peptide. The plant immune system enhancer protein or peptide can be any protein or peptide that has a beneficial effect on the immune system of a plant. Suitable plant immune system enhancer proteins and peptides include harpins, α-elastins, β-elastins, systemins, phenylalanine ammonia-lyase, elicitins, defensins, cryptogeins, flagellin proteins, and flagellin peptides (e.g., flg22).

Alternatively, the protein or peptide that protects a plant from a pathogen can be a protein or peptide that has antibacterial activity, antifungal activity, or both antibacterial and antifungal activity. Examples of such proteins and peptides include bacteriocins, lysozymes, lysozyme peptides (e.g., LysM), siderophores, non-ribosomal active peptides, conalbumins, albumins, lactoferrins, lactoferrin peptides (e.g., LfcinB), streptavidin and TasA.

The protein or peptide that protects a plant from a pathogen can also be a protein or peptide that has insecticidal activity, helminthicidal activity, suppresses insect or worm predation, or a combination thereof. For example, the protein or peptide that protects a plant from a pathogen can comprise an insecticidal bacterial toxin (e.g., a VIP insecticidal protein), an endotoxin, a Cry toxin (e.g., a Cry toxin from *Bacillus thuringiensis*), a protease inhibitor protein or peptide (e.g., a trypsin inhibitor or an arrowhead protease inhibitor), a cysteine protease, or a chitinase. Where the Cry toxin is a Cry toxin from *Bacillus thuringiensis*, the Cry toxin can be a Cry5B protein or a Cry21A protein. Cry5B and Cry21A have both insecticidal and nematocidal activity.

The protein that protects a plant from a pathogen can comprise an enzyme. Suitable enzymes include proteases and lactonases. The proteases and lactonases can be specific for a bacterial signaling molecule (e.g., a bacterial lactone homoserine signaling molecule).

Where the enzyme is a lactonase, the lactonase can comprise 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

The enzyme can also be an enzyme that is specific for a cellular component of a bacterium or fungus. For example, the enzyme can comprise a β-1,3-glucanase, a β-1,4-glucanase, a β-1,6-glucanase, a chitosinase, a chitinase, a chitosinase-like enzyme, a lyticase, a peptidase, a proteinase, a protease (e.g., an alkaline protease, an acid protease, or a neutral protease), a mutanolysin, a stapholysin, or a lysozyme.

Proteins and Peptides that Enhance Stress Resistance in Plants

The fusion proteins can comprise a targeting sequence, exosporium protein, or exosporium protein fragment and at least one protein or peptide that enhances stress resistance in a plant.

For example, the protein or peptide that enhances stress resistance in a plant comprises an enzyme that degrades a stress-related compound. Stress-related compounds include, but are not limited to, aminocyclopropane-1-carboxylic acid (ACC), reactive oxygen species, nitric oxide, oxylipins, and phenolics. Specific reactive oxygen species include hydroxyl, hydrogen peroxide, oxygen, and superoxide. The enzyme that degrades a stress-related compound can comprise a superoxide dismutase, an oxidase, a catalase, an aminocyclopropane-1-carboxylic acid deaminase, a peroxidase, an antioxidant enzyme, or an antioxidant peptide.

The protein or peptide that enhances stress resistance in a plant can also comprise a protein or peptide that protects a plant from an environmental stress. The environmental stress can comprise, for example, drought, flood, heat, freezing, salt, heavy metals, low pH, high pH, or a combination thereof. For instance, the protein or peptide that protects a plant from an environmental stress can comprises an ice nucleation protein, a prolinase, a phenylalanine ammonia lyase, an isochorismate synthase, an isochorismate pyruvate lyase, or a choline dehydrogenase.

Plant Binding Proteins and Peptides

The fusion proteins can comprise a targeting sequence, exosporium protein, or exosporium protein fragment and at least plant binding protein or peptide. The plant binding protein or peptide can be any protein or peptide that is capable of specifically or non-specifically binding to any part of a plant (e.g., a plant root or an aerial portion of a plant such as a leaf, stem, flower, or fruit) or to plant matter. Thus, for example, the plant binding protein or peptide can be a root binding protein or peptide, or a leaf binding protein or peptide.

Suitable plant binding proteins and peptides include adhesins (e.g., rhicadhesin), flagellins, omptins, lectins, expansins, biofilm structural proteins (e.g., TasA or YuaB) pilus proteins, curlus proteins, intimins, invasins, agglutinins, and afimbrial proteins.

Recombinant *Bacillus* that Express the Fusion Proteins

The fusion proteins described herein can be expressed by recombinant exosporium-producing *Bacillus* cells. The fusion protein can be any of the fusion proteins discussed above.

The recombinant exosporium-producing *Bacillus* cells can coexpress two or more of any of the fusion proteins discussed above. For example, the recombinant exosporium-producing *Bacillus* cells can coexpress at least one fusion protein that comprises a plant binding protein or peptide, together with at least one fusion protein comprising a plant growth stimulating protein or peptide, at least one fusion protein comprising a protein or peptide that protects a plant from a pathogen, or at least one protein or peptide that enhances stress resistance in a plant.

The recombinant exosporium-producing *Bacillus* cells can comprise *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis* or a combination thereof. For example, the recombinant exosporium-producing *Bacillus* cells can comprise *Bacillus cereus, Bacillus thuringiensis, Bacillus pseudomycoides*, or *Bacillus mycoides*. In particular, the recombinant exosporium-producing *Bacillus* cells can comprise *Bacillus thuringiensis* or *Bacillus mycoides*.

To generate a recombinant exosporium-producing *Bacillus* cells expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant exosporium-producing *Bacillus* cells can then exposed to conditions which will induce sporulation. Suitable conditions for inducing sporulation are known in the art. For example, the recombinant exosporium-producing *Bacillus* cells can be plated onto agar plates, and incubated at a temperature of about 30° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Recombinant Exosporium-Producing *Bacillus* Cells Having Plant-Growth Promoting Effects and/or Other Beneficial Attributes Many *Bacillus cereus* family member strains have inherent beneficial attributes. For example, some strains have plant-growth promoting effects. Any of the fusion proteins described herein can be expressed in such strains.

For example, the recombinant exosporium-producing *Bacillus* cells can comprise a plant-growth promoting strain of bacteria.

The plant-growth promoting strain of bacteria can comprise a strain of bacteria that produces an insecticidal toxin (e.g., a Cry toxin), produces a fungicidal compound (e.g., a β-1,3-glucanase, a chitosinase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

For example, where the recombinant exosporium-producing *Bacillus* cells comprises a plant-growth promoting strain of bacteria, the plant growth-promoting strain of bacteria can comprise *Bacillus mycoides* BT155 (NRRL No. B-50921), *Bacillus mycoides* EE118 (NRRL No. 13-50918), *Bacillus mycoides* EE141 (NRRL No. 13-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), or *Bacillus cereus* family member EE349 (NRRL No. B-50928). *Bacillus thuringiensis* BT013A is also known as *Bacillus thuringiensis* 4Q7. Each of these strains was deposited with the United States Department of Agriculture (USDA) Agricultural Research Service (ARS), having the address 1815 North University Street, Peoria, Ill. 61604, U.S.A., on Mar. 10, 2014, and is identified by the NRRL deposit number provided in parentheses. These deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application the Applicants will make available to the public, pursuant to 37 C.F.R. § 1.808, sample(s) of the deposit with the NRRL.

These plant-growth promoting strains were isolated from the rhizospheres of various vigorous plants and were identified by their 16S rRNA sequences, and through biochemical assays. The strains were identified at least to their genus designation by means of conventional biochemistry and morphological indicators. Biochemical assays for confirmed Gram-positive strains such as *Bacillus* included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility.

For example, the recombinant exosporium-producing *Bacillus* cells comprising a plant-growth promoting strain of bacteria can comprise *Bacillus mycoides* BT155, *Bacillus mycoides* EE141, or *Bacillus thuringiensis* BT013A. The recombinant exosporium-producing *Bacillus* cells can express any of the fusion proteins described herein, e.g., a fusion protein comprising the targeting sequence of SEQ ID NO: 60 and a non-hormone peptide (e.g., kunitz trypsin inhibitor (KTI)), an enzyme involved in the production or activation of a plant growth stimulating compound (e.g., a chitosinase), a plant binding protein or peptide (e.g., TasA); a protein or peptide that protects a plant from a pathogen (e.g., TasA), or an enzyme that degrades or modifies a bacterial, fungal, or plant nutrient source (e.g., a phosphatase such as PhoA or phytase, or an endoglucanase).

Promoters

In any of the recombinant exosporium-producing *Bacillus* cells described herein, the fusion protein can be expressed under the control of a promoter that is native to the targeting sequence, the exosporium protein, or the exosporium protein fragment of the fusion protein. For example, where the fusion protein comprises a targeting sequence derived from *B. anthracis* Sterne Bc1A (e.g., amino acids 20-35 of SEQ ID NO: 1, amino acids 1-35 of SEQ ID NO: 1, SEQ ID NO: 1, or SEQ ID NO: 60) or where the fusion protein comprises full length Bc1A (SEQ ID NO: 2) or a fragment of full length Bc1A (e.g., SEQ ID NO: 59), the fusion protein can be expressed under the control of a promoter that is normally associated with the Bc1A gene in the genome of *B. anthracis* Sterne (e.g., the promoter of SEQ ID NO: 85).

Alternatively, the fusion protein can be expressed under the control of a high-expression sporulation promoter. In some cases, the promoter that is native to the targeting sequence, exosporium protein, or exosporium protein fragment will be a high-expression sporulation promoter. In other cases, the promoter that is native to the targeting sequence, exosporium protein, or exosporium protein fragment will not be a high-expression sporulation promoter. In the latter cases, it may be advantageous to replace the native promoter with a high-expression sporulation promoter. Expression of the fusion protein under the control of a high-expression sporulation promoter provides for increased expression of the fusion protein on the exosporium of the *Bacillus cereus* family member.

The high-expression sporulation promoter can comprise one or more sigma-K sporulation-specific polymerase promoter sequences.

Suitable high-expression sporulation promoters for use in expressing the fusion proteins in a *Bacillus cereus* family member include those listed in Table 2 below:

TABLE 2

Promoter Sequences

| Promoter (SEQ ID NO.) | Sequence |
|---|---|
| BclA promoter (*B. anthracis* Sterne) (SEQ ID NO: 85) | TAATCACCCTCTTCCAAATCAAT**CATATGT**<br>**TA**TA**CATATACTA**AACTTTCCATTTTTTTA<br>AATTGTTCAAGTAGTTTAAGATTTCTTTTC<br>AATAATTCAAATGTCCGTGTCATTTTCTTT<br>CGGTTTTG**CATCTACTA**TATAATGAACGCT<br>TTATGGAGGTGAATTTATG |
| BetA promoter (*B. anthracis* Sterne) (SEQ ID NO: 86) | ATTTATTTCATTCAATTTTTCCTATTTAGT<br>ACCTACCGCACTCACAAAAAGCACCTCTCA<br>TTAATTTATATTATAGTCATTGAAATCTAA<br>TTTAATGAAATCAT**CATACTATA**TGTTTTA<br>TAAGAAGTAAAGGTAC**CATACTTAA**TTAAT<br>ACATATCTATACACTTCAATATCACAGCAT<br>GCAGTTGAATTATATCCAACTTTCATTTCA<br>AATTAAATAAGTGCCTCCGCTATTGTGAAT<br>GTCATTTACTCTCCCTACTA**CATTTAATA**A<br>TTATGACAAGCAATCATAGGAGGTTACTAC<br>ATG |
| BAS1882 promoter (*B. anthracis* Sterne) (SEQ ID NO: 87) | AATTACATAACAAGAACTACATTAGGGAGC<br>AAGCAGTCTAGCGAAAGCTAACTGCTTTTT<br>TATTAAATAACTATTTTATTAAATTTCATA<br>TATACAATCGCTTGTCCATTTCATTTGGCT<br>CTACCCACG**CATTTACTA**TTAGTAATATGA<br>ATTTTTCAGAGGTGGATTTTATT |
| Gene 3572 promoter (*B. weihenstephensis* KBAB 4) (SEQ ID NO: 88) | CTATGATTTAAGATACACAATAGCAAAAGA<br>GAAA**CATATTATA**TAACGATAAATGAAACT<br>TATGTATATGTATGGTAACTGTATATATTA<br>CTACAATACAGTATACTCATAGGAGGTAGG<br>TATG |
| YVTN β-propeller protein promoter (*B. weihenstephensis* KBAB 4) (SEQ ID NO: 89) | GGTAGGTAGATTTGAAATATGATGAAGAAA<br>AGGAATAACTAAAAGGAGTCGATATCCGAC<br>TCCTTTTAGTTATAAATAATGTGGAATTAG<br>AGTATAATTTTATATAGGTATATTGTATTA<br>GATGAACGCTTTATCCTTTAATTGTGATTA<br>ATGATGGATTGTAAGAGAAGGGGCTTACAG<br>TCCTTTTTTTATGGTGTTCTATAAGCCTTT<br>TTAAAAGGGGTACCACCCCACACCCAAAAA<br>CAGGGGGGGTTATAACTACATATTGGATGT<br>TTTGTAACGTACAAGAATCGGTATTAATTA<br>CCCTGTAAATAAGTTATGTGTATATAAGGT |

TABLE 2-continued

Promoter Sequences

| Promoter (SEQ ID NO.) | Sequence |
|---|---|
| | AACTT**TATATATTC**TCCTACAATAAAATAA<br>AGGAGGTAATAAAGTG |
| Cry1A promoter (*B. thuringiensis* HD-73) (SEQ ID NO: 90) | AACCCTTAATGCATTGGTTAAACATTGTAA<br>AGTCTAAAGCATGGATAATGGGCGAGAAGT<br>AAGTAGATTGTTAACACCCTGGGTCAAAAA<br>TTGATATTTAGTAAAATTAGTTGCACTTTG<br>TGCATTTTTT**CATAAGATG**AGT**CATATGTT**<br>**T**TAAATTGTAGTAATGAAAAACAGTAT**TAT**<br>**ATCATAATGAA**TTGGTATCTTAATAAAAGA<br>GATGGAGGTAACTTA |
| ExsY promoter (*B. thuringiensis* serovar konkukian str. 97-27) (SEQ ID NO: 91) | TAATTCCACCTTCCCTTATCCTCTTTCGCC<br>TATTTAAAAAAAGGTCTTGAGATTGTGACC<br>AAATCTCCTCAACTCC**AATATCTTA**TTAAT<br>GTAAATACAAACAAGAAGATAAGGAGTGAC<br>ATTAA |
| CotY promoter (*B. thuringiensis* Al Hakam) (SEQ ID NO: 92) | AGGATGTCTTTTTTTATATTGTATTATGTA<br>CATCCCTACTATATAAATTCCCTGCTTTTA<br>TCGTAAGAATTAACGTAATATCAACCATAT<br>CCCGTT**CATATTGTA**GTAGTGTATGTCAGA<br>ACTCACGAGAAGGAGTGAACATAA |
| YjcA promoter (*B. thuringiensis* serovar kurstaki str. HD73) (SEQ ID NO: 93) | TTAATGTCACTCCTTATCTTCTTGTTTGTA<br>TTTACATT**AATAAGATA**TTGGAGTTGAGGA<br>GATTTGGTCACAATCTCAAGACCTTTTTTT<br>TAAATAGGCGAAAGAGGATAAGGGAAGGTG<br>GAATTA |
| YjcB promoter (*B. thuringiensis* serovar kurstaki str. HD73) (SEQ ID NO: 94) | ATATATTTTCATAATACGAGAAAAAGCGGA<br>GTTTAAAAGAATGAGGGAACGGAAATAAAG<br>AGTTGTT**CATATAGTA**AATAGACAGAATTG<br>ACAGTAGAGGAGA |
| BxpB promoter (*B. thuringiensis* Al Hakam) (SEQ ID NO: 95) | AAACTAAATAATGAGCTAAGCATGGATTGG<br>GTGGCAGAATTATCTGCCACCCAATC**CATG**<br>**CTTAA**CGAGTATTATTATGTAAATTTCTTA<br>AAATTGGGAACTTGTCTAGAACATAGAACC<br>TGTCCTTTT**CATTAACTG**AAAGTAGAAACA<br>GATAAAGGAGTGAAAAACA |
| Rhamnose promoter (*B. thuringiensis* Al Hakam) (SEQ ID NO: 96) | ATTCACTACAACGGGGATGAGTTTGATGCG<br>GATA**CATATGAGA**AGTACCGGAAAGTGTTT<br>GTAGAA**CATTACAA**AGATATATTATCTCCA<br>TCATAAAGGAGAGATGCAAAG |
| CotY/CotZ promoter (*B. anthracis* Sterne) (SEQ ID NO: 97) | CGCGCACCACTTCGTCGTACAACAACGCAA<br>GAAGAAGTTGGGGATACAGCAGTATTCTTA<br>TTCAGTGATTTAGCACGCGGCGTAACAGGA<br>GAAAACATTCACGTTGATTCAGGGTAT**CAT**<br>**ATCTTA**GGATAAATATAATATTAATTTTAA<br>AGGACAATCTCTACATGTTGAGATTGTCCT<br>TTTTATTTGTTCTTAGAAAGAACGATTTTT<br>AACGAAAGTTCTTACCACGTTATGAATATA<br>AGTATAATAGTACACGATTTATTCAGCTAC<br>GTA |
| BclC promoter (*B. anthracis* Sterne) (SEQ ID NO: 98) | TGAAGTATCTAGAGCTAATTTACGCAAAGG<br>AATCTCAGGACAACACTTTCGCAACACCTA<br>TATTTTAAATTTAATAAAAAAAGAGACTCC<br>GGAGTCAGAAATTATAAAGCTAGCTGGGTT<br>CAAATCAAAAATTTCACTAAAACGATATTA<br>TCAATACGCAGAAAATGGAAAAAAACGCCTT<br>ATCATAAGGCGTTTTTTCCATTTTTTCTTC<br>AAACAAACGATTTTACTATGACCATTTAAC<br>TAATTTTTG**CATCTACTA**TGATGAGTTTCA<br>TTCACATTCTCATTAGAAAGGAGAGATTTA<br>ATG |

TABLE 2-continued

| Promoter Sequences | |
|---|---|
| Promoter (SEQ ID NO.) | Sequence |
| Sigma K promoter (*B. anthracis* Sterne) (SEQ ID NO: 99) | TATATCATATGTAAAATTAGTTCTTATTCC<br>CA**CATATCATA**TAGAATCGC**CATATTATA**C<br>ATGCAGAAAACTAAGTATGGTATTATTCTT<br>AAATTGTTTAGCACCTTCTAATATTACAGA<br>TAGAATCCGTCATTTTCAACAGTGAACATG<br>GATTTCTTCTGAACACAACTCTTTTTCTTT<br>CCTTATTTCCAAAAAGAAAAGCAGCCCATT<br>TTAAAATACGGCTGCTTGTAATGTACATTA |
| InhA promoter (*B. thuringiensis* Al Hakam) (SEQ ID NO: 100) | TATCACATAACTCTTTATTTTTAATATTTC<br>GA**CATAAAGTG**AAACTTTAATCAGTGGGGG<br>CTTTGTTCATCCCCCCACTGATTATTAATT<br>GAACCAAGGGATAAAAAGATAGAGGGTCTG<br>ACCAGAAAACTGGAGGGCATGATTCTATAA<br>CAAAAAGCTTAATGTTTATAGAATTATGTC<br>TTTTTATATAGGGAGGGTAGTAAACAGAGA<br>TTTGGACAAAAATGCACCGATTTATCTGAA<br>TTTTAAGTTTTATAAAGGGGAGAAATG |
| BclA cluster glycosyl transferase operon 1 (*B. thuringiensis* serovar konkukian str. 97-27) (SEQ ID NO: 101) | ATTTTTTACTTAGCAGTAAAACTGATATCA<br>GTTTTACTGCTTTTTCATTTTTAAATTCAA<br>TCATTAAATCTTCCTTTTCTACATAGT**CAT**<br>**AATGTT**GTATGACATTCCGTAGGAGGCACT<br>TATA |
| BclA cluster glycosyl transferase operon 2 (*B. thuringiensis* serovar kurstaki str. HD73) (SEQ ID NO: 102) | ACATAAATTCACCTCCATAAAGCGTTCATT<br>ATATAGTAGATGCAAAACCGAAAGAAAATG<br>ACACGGACATTTGAATTATTGAAAAGAAAT<br>CTTAAACTACTTGAACAATTTAAAAAAATG<br>GAAAGTTTAGTATATGTATAA**CATATGATT**<br>GATTTGGAAGAGGGTGATTA |
| Glycosyl transferase promoter (*B. thuringiensis* Al Hakam) (SEQ ID NO: 103) | TTCTATTTTCCAA**CATAACATG**CTACGATT<br>AAATGGTTTTTTGCAAATGCCTTCTTGGGA<br>AGAAGGATTAGAGCGTTTTTTTATAGAAAC<br>CAAAAGTCATTAACAATTTTAAGTTAATGA<br>CTTTTTTGTTTGCCTTTAAGAGGTTTTATG<br>TTACTATAATTATAGTATCAGGTACTAATA<br>ACAAGTATAAGTATTTCTGGGAGGATATAT<br>CA |

In the promoter sequences listed in Table 2 above, the locations of the sigma-K sporulation-specific polymerase promoter sequences are indicated by bold and underlined text. The Cry1A promoter (*B. thuringiensis* HD-73; SEQ ID NO: 90) has a total of four sigma-K sequences, two of which overlap with one another, as indicated by the double underlining in Table 2.

Preferred high-expression sporulation promoters for use in expressing the fusion proteins in a *Bacillus cereus* family member include the BetA promoter (*B. anthracis* Sterne; SEQ ID NO: 86), the BclA promoter (*B. anthracis* Sterne; SEQ ID NO: 85), the BclA cluster glycosyl transferase operons 1 and 2 promoters (*B. anthracis* Sterne; SEQ ID NOS: 101 and 102), and the YVTN β-propeller protein promoter (*B. weihenstephensis* KBAB 4; SEQ ID NO: 89).

In any of the recombinant exosporium-producing *Bacillus* cells described herein, the fusion protein can be expressed under the control of a sporulation promoter comprising a nucleic acid sequence having at least 80%, at least 90%, at least 95%, at least 98%, at least 99%, or 100% identity with a nucleic acid sequence of any one of SEQ ID NOS: 85-103.

When the sporulation promoter comprising a nucleic acid sequence having at least 80%, at least 90%, at least 95%, at least 98%, or at least 99% identity with a nucleic acid sequence of any one of SEQ ID NOS: 85-103, the sigma-K sporulation-specific polymerase promoter sequence or sequences preferably have 100% identity with the corresponding nucleotides of SEQ ID NO: 85, 86, 87, 88, 89, 90, 91, 92, 93, 94, 95, 96, 97, 98, 99, 100, 101, 102, or 103. For example, as illustrated in Table 2 above, the BclA promoter of *B. anthracis* Sterne (SEQ ID NO: 85) has sigma-K sporulation-specific polymerase promoter sequences at nucleotides 24-32, 35-43, and 129-137. Thus, if the sporulation promoter comprises a sequence having at least 90% identity with the nucleic acid sequence of SEQ ID NO: 85, it is preferred that the nucleotides of the sporulation promoter corresponding to nucleotides 24-32, 35-43, and 129-137 of SEQ ID NO: 85 have 100% identity with nucleotides 24-32, 35-43, and 129-137 of SEQ ID NO: 85.

In any of the methods described herein for stimulating plant growth, plants grown in the plant growth medium comprising the recombinant exosporium-producing *Bacillus* cells and at least one further biological control agent selected from the particular microorganisms disclosed herein exhibit increased growth as compared to the growth of plants in the identical plant growth medium that does not contain the recombinant exosporium-producing *Bacillus* cells.

In any of the compositions and methods described herein for stimulating plant growth, the recombinant exosporium-producing *Bacillus* cells can comprise any of the recombinant plant-growth promoting strains of bacteria described above.

In any of the compositions or methods for stimulating plant growth disclosed herein, the fusion protein can be expressed under the control of any of the promoters described above.

Synthetic Nodulation Factors and Plant Growth Stimulators

In some embodiments, the compositions comprising recombinant exosporium-producing *Bacillus* cells that express a fusion protein and at least one of the biological control agents described herein further comprise a synthetic nodulation factor and/or plant growth stimulator. A non-limiting example of such a synthetic compound is a compound of general formula (I)

(I)

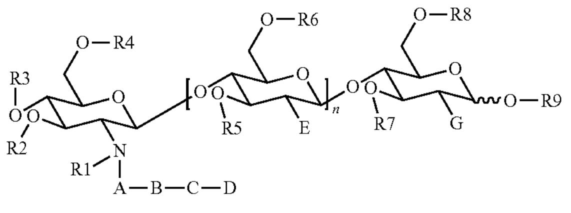

wherein:

n is 2 or 3;

A is —C(O)—;

B is a phenylene;

C is —O—;

D is a linear hydrocarbon-based chain comprising 11 carbons, which is saturated or unsaturated between carbons 4 and 5;

E and G are independently selected from the group consisting of a substituent NHR20;

R1, R2, R3, R4, R5, R6, R7, and R9 are H;

R8 is selected from the group consisting of H, fucosyl, methylfucosyl, $SO_3H$, $SO_3Li$, $SO_3Na$, $SO_3K$, and $SO_3N(C_{1-8}\text{-alkyl})_4$;

R20 is $C(O)C_{1-6}$-alkyl; and any agriculturally acceptable geometrical and/or optical isomer, enantiomer and/or diastereoisomer, tautomer, salt, N-oxide, sulfoxide, or sulfone thereof.

The salt may be selected from the group consisting of lithium, sodium, potassium, and tetraalkylammonium salts.

In certain embodiments, E and G are $NHC(O)CH_3$.

In other embodiments, R8 is selected from the group consisting of H, $SO_3H$, $SO_3Li$, $SO_3Na$, $SO_3K$, $SO_3N(C_{1-8}\text{ alkyl})_4$ and a substituent of formula:

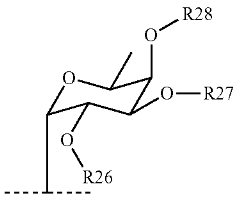

wherein:

R26 is selected from the group consisting of H and $CH_3$; and

R27 and R28 are independently selected from the group consisting of H, $C(O)CH_3$, $SO_3H$, $SO_3Li$, $SO_3Na$, $SO_3K$ and $SO_3N(C_{1-8}alkyl)_4$.

In some aspects, R26, R27, and R28 are all hydrogen.

Additional non-limiting examples of a synthetic nodulation factor and/or plant growth stimulator that can be used in the present invention include compounds of the structural formulae:

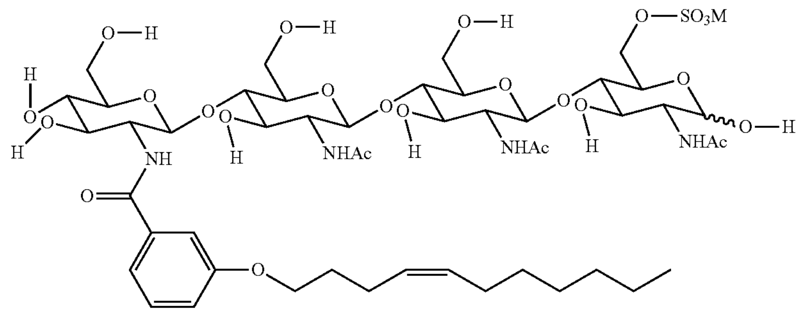

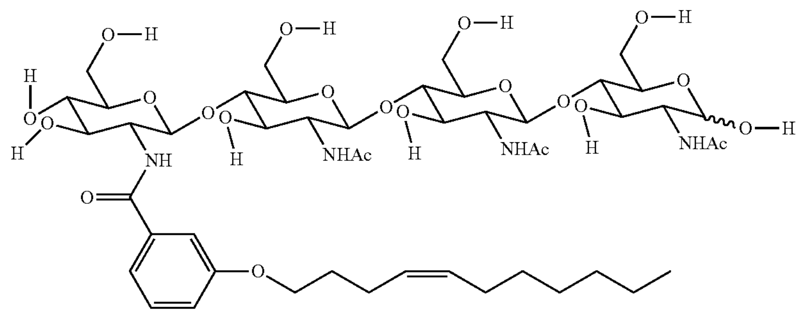

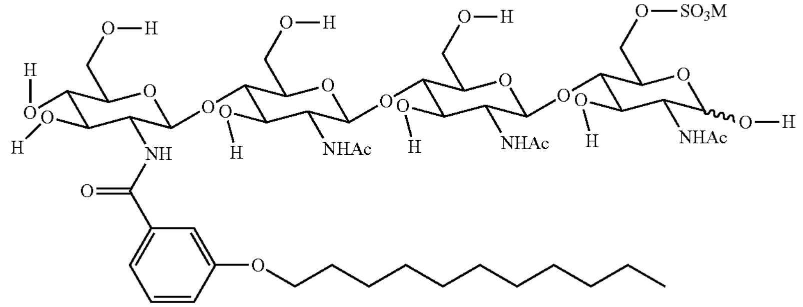

-continued
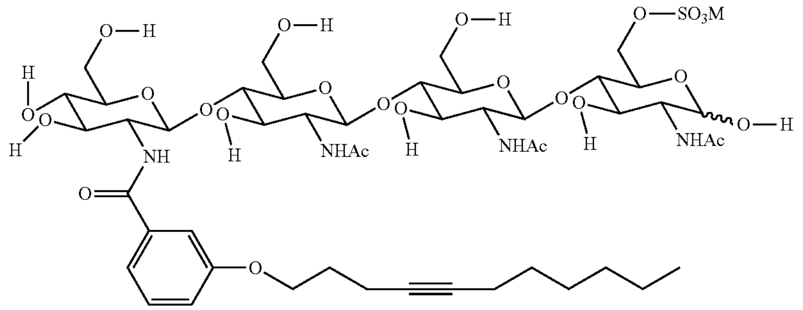
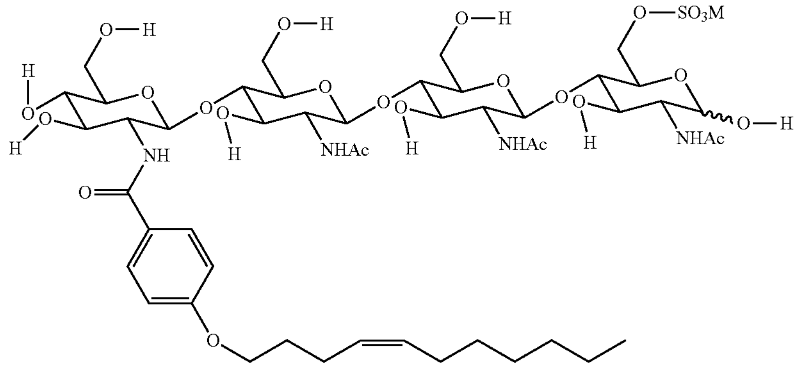
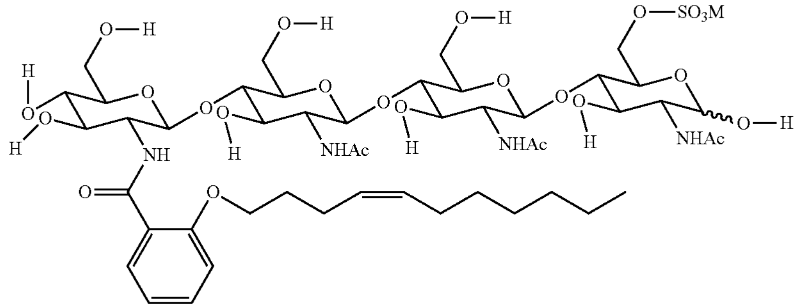
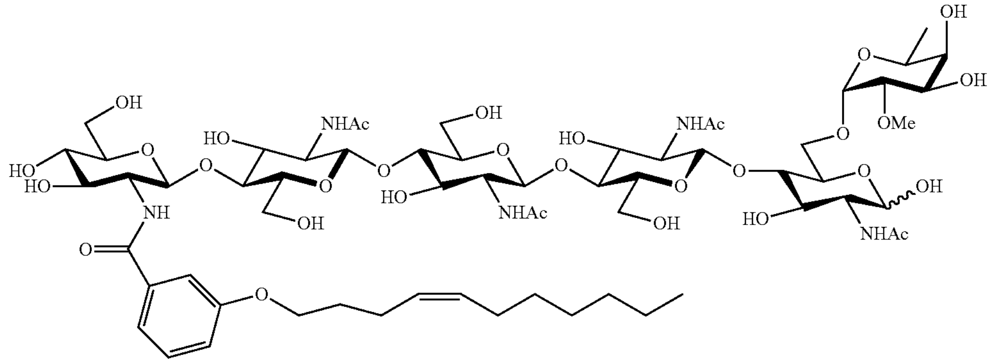
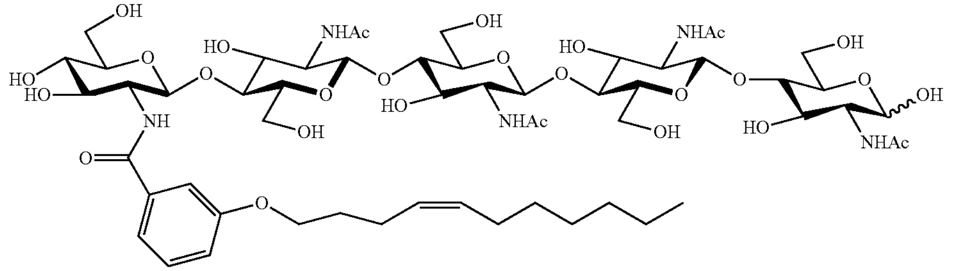

-continued
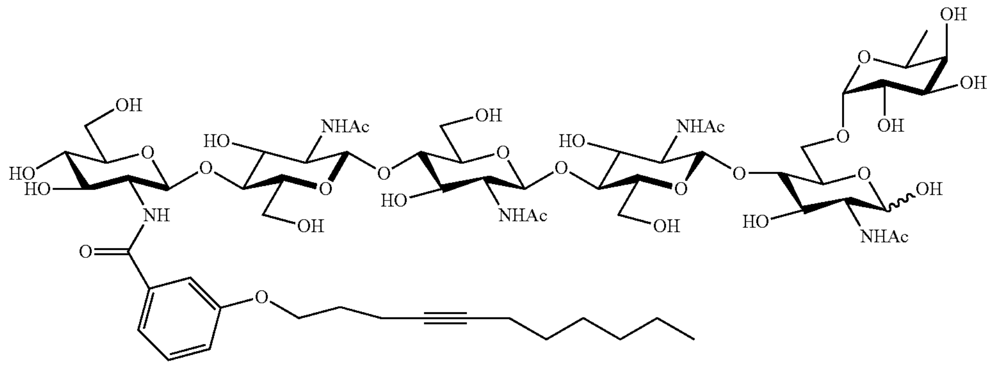
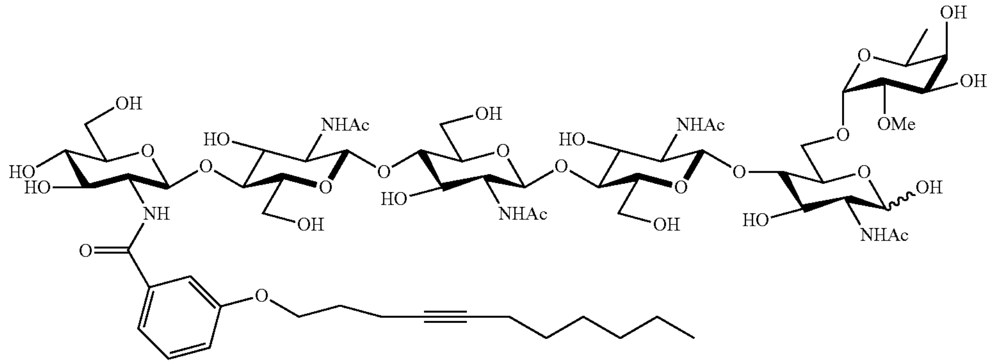
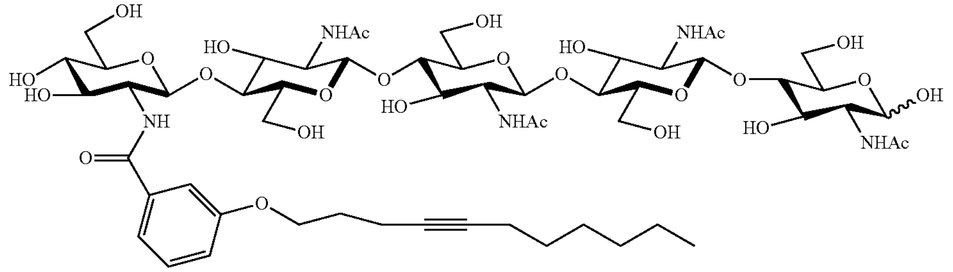
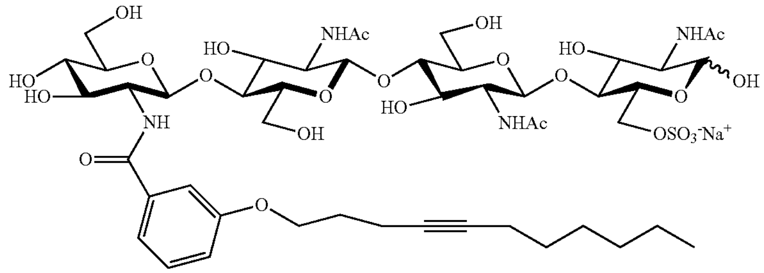
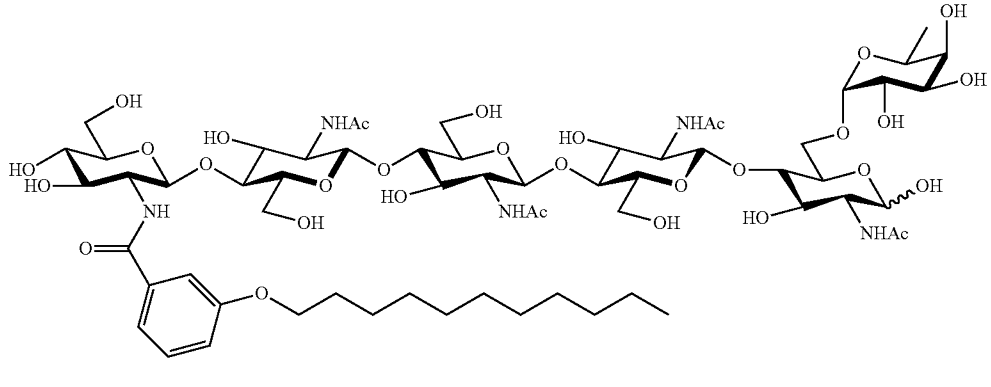

-continued
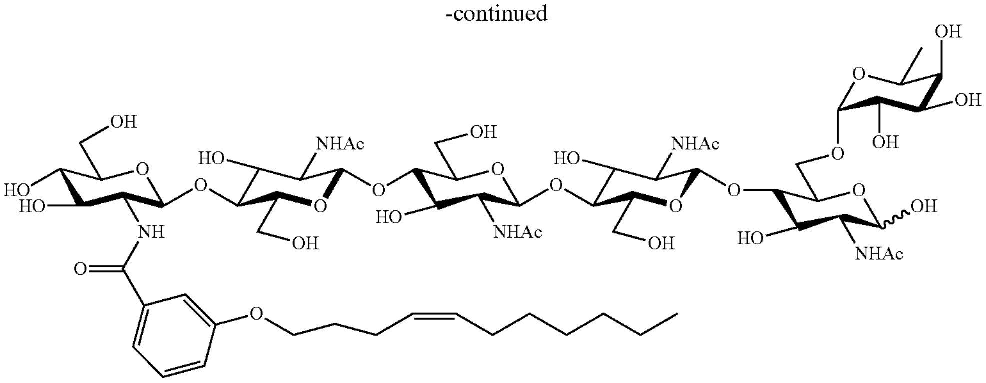
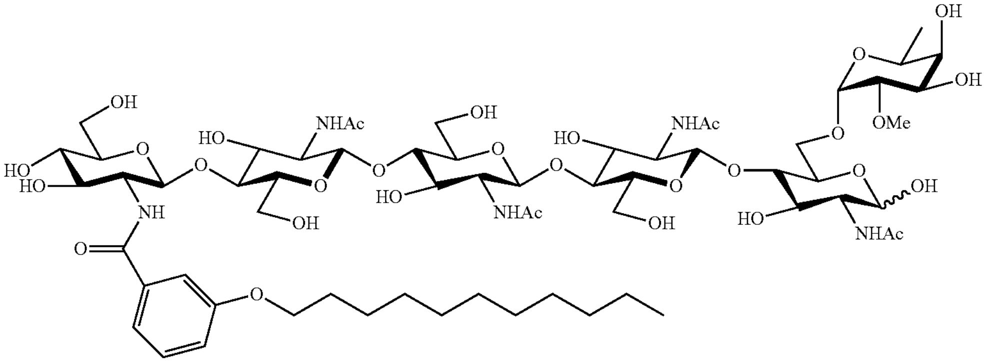
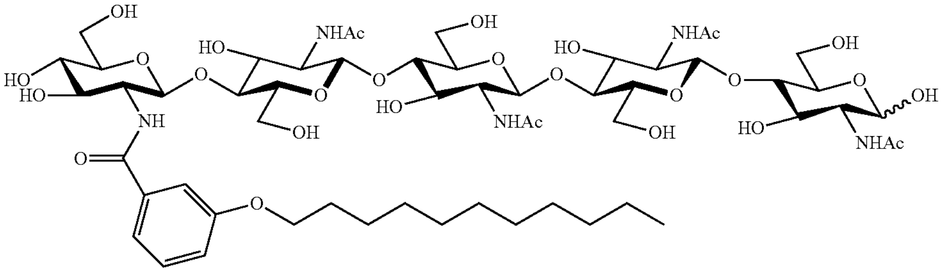
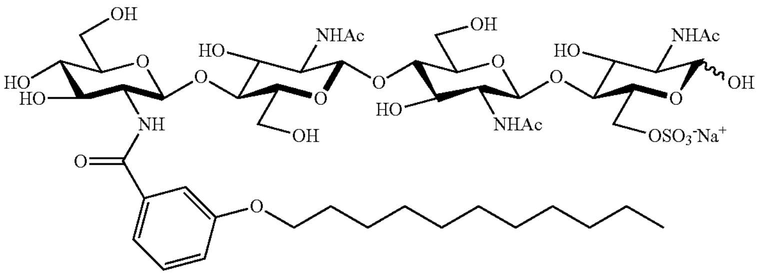
in which, when it is present, M is selected from the group consisting of $H^+$, $Li^+$, $Na^+$, $K^+$ and $(C_{1-8}alkyl)_4N^+$.
In certain aspects, the synthetic nodulation factor and/or plant growth stimulator is a compound selected from the group consisting of:

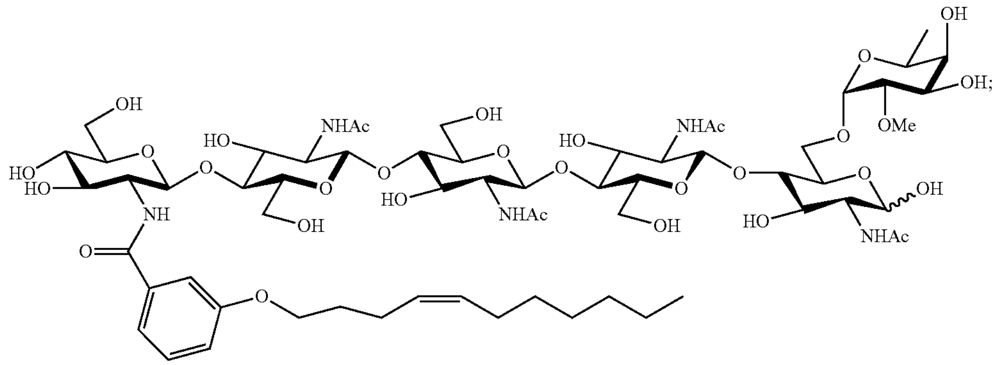

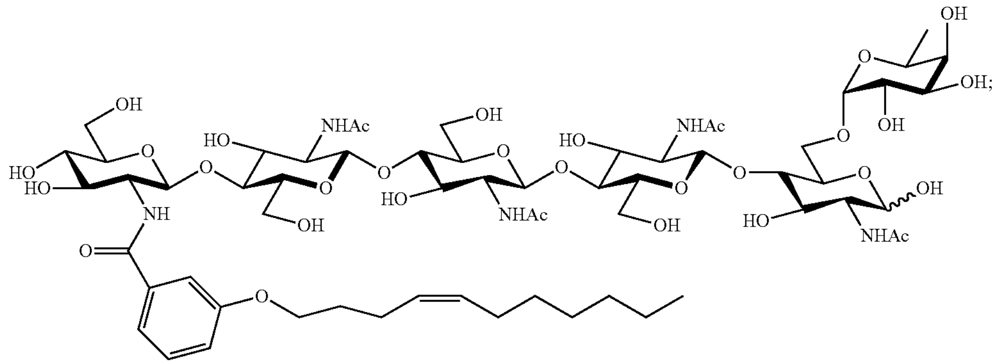

and

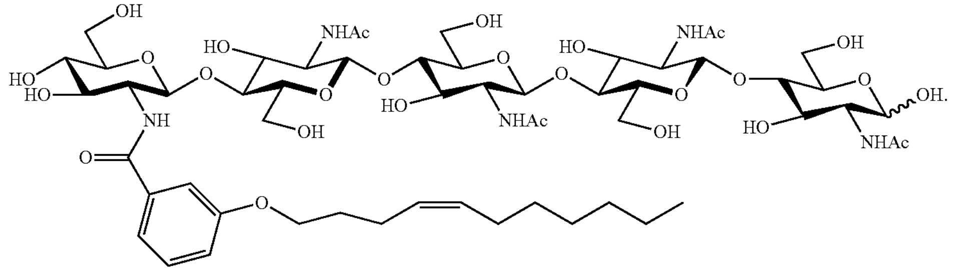

Additional Biological Control Agents

Biological control agents can include, in particular, bacteria, fungi or yeasts, protozoa, viruses, entomopathogenic nematodes, inoculants and botanicals and/or mutants of them having all identifying characteristics of the respective strain, and/or at least one metabolite produced by the respective strain that exhibits activity against insects, mites, nematodes and/or phytopathogens. The present invention relates to the combinations of the above-described recombinant *Bacillus* cells with the particular biological control agents described herein and/or to mutants of specific strains of microorganisms described herein, where the mutants have all the identifying characteristics of the respective strain, and/or at least one metabolite produced by the respective strain that exhibits activity against insects, mites, nematodes and/or phytopathogens or promotes plant growth and/or enhances plant health.

The bacterial cells, spores and metabolites in culture broth resulting from fermentation (the "whole broth" or "fermentation broth") of the particular microorganisms described herein may be used directly or concentrated by conventional industrial methods, such as centrifugation, filtration, and evaporation, or processed into dry powder and granules by spray drying, drum drying and freeze drying, for example.

The terms "whole broth" and "fermentation broth," as used herein, refer to the culture broth resulting from fermentation before any downstream treatment. The whole broth encompasses the microorganism and its component parts, unused raw substrates, and metabolites produced by the microorganism during fermentation. The term "broth concentrate," as used herein, refers to whole broth (fermentation broth) that has been concentrated by conventional industrial methods, as described above, but remains in liquid form. The term "fermentation solid," as used herein, refers to dried fermentation broth. The term "fermentation product," as used herein, refers to whole broth, broth concentrate and/or fermentation solids. Compositions of the present invention include fermentation products. In some embodiments, the concentrated fermentation broth is washed, for example, via a diafiltration process, to remove residual fermentation broth and metabolites.

In another embodiment, the fermentation broth or broth concentrate can be dried with or without the addition of carriers, inerts, or additives using conventional drying processes or methods such as spray drying, freeze drying, tray drying, fluidized-bed drying, drum drying, or evaporation.

According to the invention, biological control agents, which are summarized under the term "bacteria", include spore-forming, root-colonizing bacteria, or bacteria and their metabolites useful as biological insecticides, -nematicides, miticides, or -fungicide or soil amendments improving plant health and growth. Bacteria to be used or employed according to the invention follow.

*B. cereus* strains, including strain CNCM 1-1562 (cf. U.S. Pat. No. 6,406,690), *Bacillus firmus, Bacillus pumilus*, in particular strain GB34 (products known as YIELD SHIELD®), and strain QST2808 (products known as SONATA® QST2808) *Bacillus subtilis*, in particular strain GB03 (products known as KODIAK®), strain QST713 (products known as SERENADE® QST713), strain AQ30002 (aka QST30002; NRRL Accession No. B-50421, known from WO 2012/087980, which is incorporated herein by reference), strain AQ30004 (aka QST30004; NRRL Accession No. B-50455, known from WO 2012/087980, which is incorporated herein by reference), strain AQ743 (NRRL Accession No. B-21665), strain AQ153 (ATCC Accession No. 55614 as described in WO 98/21964), (1.79) *Streptomyces galbus* strain AQ 6047 (Accession Number NRRL 30232), (1.91) *Rhodococcus globerulus* AQ719 (NRRL Accession No. B-21663), (1.92) *Bacillus* sp. AQ175 (ATCC Accession No. 55608), (1.93) *Bacillus* sp. AQ 177 (ATCC Accession No. 55609), (1.94) *Bacillus* sp. AQ178 (ATCC Accession No. 53522), (1.95) *Streptomyces* sp. strain described in WO 02/26041 A2 (NRRL Accession No. B-30145), (1.96) *Streptomyces microflavus* strain NRRL B-50550, (1.97) *Streptomyces microflavus* strain M (Accession No. 091013-02), gougerotin-containing fermentation products of *Streptomyces*, as described in WO2014/059275, and *Streptomyces galbus* QST6047, described in U.S. Pat. No. 6,682,925.

In a particular embodiment the following bacteria are used in combination with the exosporium-producing recombinant *Bacillus* cells described above:

*Bacillus firmus*, in particular strain 1-1582 (products known as Bionem, Votivo, Flocter),

*Bacillus pumilus*, in particular strain GB34 (products known as YIELD SHIELD®), and strain QST2808 (products known as SONATA® QST2808),

*Bacillus subtilis*, in particular strain GB03 (products known as KODIAK®), strain QST713 (products known as SERENADE® QST713); NRRL Accession No. B-50455, known from WO 2012/087980, which is incorporated herein by reference), or *B. subtilis* var. *amyloliquefaciens* strain FZB24 (products known as TAEGRO®), strain AQ743 (NRRL Accession No. B-21665), strain AQ153 (ATCC Accession No. 55614 as described in WO 98/21964), In one embodiment the composition of the present invention comprises a combination of at least one of the particular biological control agents described herein and at least one further biological control agent selected from the group consisting of *Bacillus chitinosporus* AQ746 (NRRL Accession No. B-21618), *Bacillus mycoides* AQ726 (NRRL Accession No. B-21664), *Bacillus pumilus* QST2808 (NRRL Accession No. B-30087), *Bacillus pumilus* AQ717 (NRRL Accession No. B-21662), *Bacillus* sp. AQ175 (ATCC Accession No. 55608), *Bacillus* sp. AQ177 (ATCC Accession No. 55609), *Bacillus* sp. AQ178 (ATCC Accession No. 53522), *Bacillus subtilis* AQ743 (NRRL Accession No. B-21665), *Bacillus subtilis* AQ713 (NRRL Accession No. B-21661), *Bacillus subtilis* AQ153 (ATCC Accession No. 55614), *Muscodor albus* 620 (NRRL Accession No. 30547), *Muscodor roseus* A3-5 (NRRL Accession No. 30548), *Rhodococcus globerulus* AQ719 (NRRL Accession No. B-21663), *Streptomyces galbus* (NRRL Accession No. 30232), *Streptomyces* sp. (NRRL Accession No. B-30145), *Bacillus subtilis* AQ30002 (NRRL Accession No. B-50421), and *Bacillus subtilis* AQ30004 (NRRL Accession No. B-50455) and/or a mutant of these strains having all the identifying characteristics of the respective strain, and/or at least one metabolite produced by the respective strain that exhibits activity against insects, mites, nematodes and/or phytopathogens.

Said further biological control agents are known in the art as follows:

*Bacillus chitinosporus* AQ746 (NRRL Accession No. B-21618) is known from WO 98/21966 A2. It is specifically active against nematodes and insects and produces non-exotoxin, non-proteinaceous, active metabolites in its supernatant. Those metabolites are active against nematodes and cockroaches, but inactive against flies, corn rootworm or beet armyworm.

*Bacillus mycoides* AQ726 (NRRL Accession No. B-21664) and its water-soluble metabolites kill or stunt insects such as corn rootworm larvae and aphids (WO 99/09820 A1).

As described in WO 00/58442 A1 *Bacillus pumilus* QST2808 (NRRL Accession No. B-30087) is able to inhibit a broad range of fungal plant diseases in vivo. Commercially available formulations of this strain are sold under the tradenames SONATA® and BALLAD® PLUS from Bayer CropScience LP (North Carolina, USA).

*Bacillus pumilus* AQ717 (NRRL Accession B-21662) is known from WO 99/10477 A1. It produces a metabolite that exhibits pesticidal activity against corn rootworms, nematodes and beet armyworms.

The bacterial strains *Bacillus* sp. AQ175 (ATCC Accession No. 55608), *Bacillus* sp. AQ177 (ATCC Accession No. 55609) and *Bacillus* sp. AQ178 (ATCC Accession No. 53522) described in WO 98/21967 A1 are effective in treating and protecting plants from aboveground fungal and bacterial infections.

The metabolite-producing strain *Bacillus subtilis* AQ743 (NRRL Accession No. B-21665) kills or stunts corn rootworm larvae, beet armyworm larvae, fly adults and nematodes (cf. WO 99/09819).

*Bacillus subtilis* AQ713 (Accession No. B-21661), also named *Bacillus subtilis* QST713, exhibits broad fungicidal and bactericidal activity and also exhibits corn rootworm activity (WO 98/50422 A1). Commercially available formulation of this strain are available under the tradenames SERENADE® MAX, SERENADE SOIL®, SERENADE® ASO, SERENADE® CPB and RHAPSODY® from Bayer CropScience LP (North Carolina, USA). The SERENADE® product (U.S. EPA Registration No. 69592-12) contains a patented strain of *Bacillus subtilis* (strain QST713) and many different lipopeptides that work synergistically to destroy disease pathogens and provide superior antimicrobial activity. The SERENADE® product is used to protect plants such as vegetables, fruit, nut and vine crops against diseases such as Fire Blight, *Botrytis*, Sour Rot, Rust, Sclerotinia, Powdery Mildew, Bacterial Spot and White Mold. The SERENADE® products are available as either liquid or dry formulations which can be applied as a foliar and/or soil treatment. Copies of U.S. EPA Master Labels for the SERENADE® products, including SERENADE® ASO, SERENADE® MAX, and SERENADE SOIL®, are publicly available through National Pesticide Information Retrieval System's (NPIRSv) USEPA/OPP Pesticide Product Label System (PPLS).

SERENADE® ASO (Aqueous Suspension-Organic) contains 1.34% of dried QST713 as an active ingredient and 98.66% of other ingredients. SERENADE® ASO is formulated to contain a minimum of $1\times10^9$ cfu/g of QST713 while the maximum amount of QST713 has been determined to be $3.3\times10^{10}$ cfu/g. For further information, see the U.S. EPA Master Labels for SERENADE® ASO dated Jan. 4, 2010, which is incorporated by reference herein in its entirety.

SERENADE® MAX contains 14.6% of dried QST713 as an active ingredient and 85.4% of other ingredients. SERENADE® MAX is formulated to contain a minimum of $7.3\times10^9$ cfu/g of QST713 while the maximum amount of QST713 has been determined to be $7.9\times10^{10}$ cfu/g. For further information, see the U.S. EPA Master Label for SERENADE® MAX, which is incorporated by reference herein in its entirety.

*Bacillus subtilis* AQ153 (ATCC Accession No. 55614) as described in WO 98/21964 A1 is effective in inhibiting growth of plant pathogenic bacteria and fungi.

WO 02/02082898 A1 describes endophytic fungi including *Muscodor albus* 620, also known as *Muscodor albus* QST20799 (NRRL Accession No. 30547) and *Muscodor roseus* A3-5 (NRRL Accession No. 30548) that produce a mixture of volatile antibiotics with activity against fungi, bacteria, insects and nematodes.

*Rhodococcus globerulus* AQ719 (NRRL Accession No. B-21663) produces metabolites that exhibits pesticidal activity against corn rootworms (U.S. Pat. No. 6,027,723 A).

WO 01/79480 A2 describes a strain of *Streptomyces galbus* (NRRL Accession No. 30232) which shows insecticidal activity against Lepidoptera.

The *Streptomyces* sp. strain described in WO 02/26041 A2 (NRRL Accession No. B-30145) exhibits antifungal activity on specific plant pathogens such as *Alternaria, Phytophthora, Botrytis, Rhizoctonia* and *Sclerotinia.*

The strains *Bacillus subtilis* AQ30002 (also known as QST30002) (NRRL Accession No. B-50421, deposited on Oct. 5, 2010) and *Bacillus subtilis* AQ30004 (also known as QST30004) (NRRL Accession No. B-50455, deposited on Oct. 5, 2010) are known from WO 2012/087980 A1, which is incorporated herein by reference. As described therein, these BCAs exhibit a broad fungicidal and bactericidal activity. B19 and B20 have a mutation in the swrA gene that results in impaired swarming ability and enhanced plant health promotion compared to a strain containing a wildtype swrA gene. The mutation causes these BCAs to form a more robust biofilm than the wildtype strain, thereby enhancing its fungicidal and bactericidal activity.

In some embodiments, the biological control agent is a *Bacillus subtilis* strain, such as *Bacillus subtilis* QST713, which produces a fengycin-type compound, an iturin-type compound, and/or a surfactin-type compound. In some aspects, the lipopeptide is a fengycin-type compound such as plipastatin A1, plipastatin B1, plipastatin B2, fengycin A, fengycin B, agrastatin 1, or agrastatin 2. In other aspects, the lipopeptide is an iturin-type compound such as iturin A, mycosubtilin, or bacillomycin.

Other lipopeptide-producing strains that are suitable for use in the compositions and methods of the present invention include *Bacillus amyloliquefaciens* strain D747 (available as BACSTAR® from Etec Crop Solutions, NZ and also available as DOUBLE NICKEL™ from Certis, US); *Bacillus subtilis* MBI600 (available as SUBTILEX® from Becker Underwood, U.S. EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 is available from Novozymes Biologicals Inc. (Salem, Va.) or Syngenta Crop Protection, LLC (Greensboro, N.C.) as the fungicide TAEGRO® or TAEGRO® ECO (EPA Registration No. 70127-5).

In some embodiments, the biological control agent in the synergistic combinations of the present invention is:

*Bacillus firmus*, including strain 1-1582 (products known as Bionem, Votivo, Flocter), disclosed in U.S. Pat. No. 6,406,690 (which is herein incorporated by reference) and deposited with the CNCM on May 29, 1995, with Accession No. CNCM I-1582,

*Bacillus pumilus*, including strain GB34 (products known as YIELD SHIELD®) and strain QST2808 (products known as SONATA® QST2808),

*Bacillus subtilis* and *Bacillus amyloliquefaciens*, including those that produce lipopeptides and, in particular, a combination of plipastatins or fengycins, surfactins and/or iturins. Also, as to *Bacillus subtilis*, in particular strain GB03 (products known as KODIAK®, c.f. U.S. EPA, Pesticide Fact Sheet—*Bacillus subtilis* GB03 1992), strain QST713 (products known as SERENADE® QST713), strain AQ30002 (aka QST30002; NRRL Accession No. B-50421, known from WO 2012/087980, which is incorporated herein by reference), and strain AQ30004 (aka QST30004; NRRL Accession No. B-50455, known from WO 2012/087980, which is incorporated herein by reference).

According to the invention biological control agents which may be comprised in the composition of the invention and that are summarized under the term "fungi" or "yeasts" are the following organisms and and/or mutants of them having all identifying characteristics of the respective strain, and/or metabolites produced by the respective strain that exhibit activity against insects, mites, nematodes and/or phytopathogens (the numbering is used in the complete description):

*Muscodor albus*, in particular strain QST20799 (products known as ARABESQUE™ or ANDANTE™), *Coniothyrium minitans*, in particular strain CON/M/91-8 (products known as CONTANS®), *Lagenidium giganteum* (products known as LAGINEX® by AgraQuest, Inc.), *Paecilomyces lilacinus*, in particular spores of *P. lilacinus* strain 251 (products known as BIOACT®, cf. Crop Protection 2008, 27, 352-361).

According to one embodiment of the present invention the biological control agent comprises not only the pure cultures of the respective microorganisms, but also their suspensions in a whole broth culture or a metabolite-containing supernatant or a purified metabolite obtained from whole broth culture of the strain. "Whole broth culture" refers to a liquid culture containing both cells and media. "Supernatant" refers to the liquid broth remaining when cells grown in broth are removed by centrifugation, filtration, sedimentation, or other means well known in the art.

The above-mentioned metabolites produced by the non-pathogenic microorganisms include antibiotics, enzymes, siderophores and growth promoting agents, for example zwittermicin-A, kanosamine, polyoxine, enzymes such as α-amylase, chitinases, and pektinases, phytohormones and precursors thereof, such as auxines, gibberlin-like substances, cytokinin-like compounds, lipopeptides such as iturins, plipastatins or surfactins, e.g., agrastatin A, bacillomycin D, bacilysin, difficidin, macrolactin, fengycin, bacilysin and bacillaene.

According to the invention, the biological control agents described herein may be employed or used in any physiologic state such as active or dormant.

Compositions According to the Present Invention

According to the present invention the composition comprises a) a recombinant exosporium-producing *Bacillus* cells that expresses a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus cereus* family member; and b) at least one further and different particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount.

A "synergistically effective amount" according to the present invention represents a quantity of a combination of a recombinant exosporium-producing *Bacillus* cells that expresses a fusion protein and at least one further particular biological control agent described herein that is more effective against insects, mites, nematodes and/or phytopathogens than the recombinant exosporium-producing *Bacillus* cells that expresses a fusion protein or such further biological control agent alone. A "synergistically effective amount" according to the present invention also represents a quantity of a combination of a recombinant exosporium-producing *Bacillus* cells that expresses a fusion protein and at least one further particular biological control agent described herein that is more effective at enhancing plant growth and/or promoting plant health than the recombinant exosporium-producing *Bacillus* cells that expresses a fusion protein or such further biological control agent alone.

The present invention comprises each and every combination of each of the further particular biological control agents described herein with the recombinant exosporium-producing *Bacillus* cells.

In a preferred embodiment the composition according to the present invention comprises at least one additional fungicide and/or at least one insecticide, with the proviso that the recombinant exosporium-producing *Bacillus* cells, the insecticide and the fungicide are not identical.

The term "active compound" or "active ingredient" is used in the present description to designate the recombinant exosporium-producing *Bacillus* cells, the at least one further biological control agent and/or a mutant of it having all identifying characteristics of the respective strain, and/or at least one metabolite produced by the respective strain that exhibits activity against insects, mites, nematodes and/or phytopathogens, the at least one insecticide and the at least one fungicide.

Further Additives

One aspect of the present invention is to provide a composition as described above additionally comprising at least one auxiliary selected from the group consisting of extenders, solvents, spontaneity promoters, carriers, emulsifiers, dispersants, frost protectants, thickeners and adjuvants. Those compositions are referred to as formulations.

Accordingly, in one aspect of the present invention such formulations, and application forms prepared from them, are provided as crop protection agents and/or pesticidal agents, such as drench, drip and spray liquors, comprising the composition of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on Development and Use of FAO and WHO Specifications for Pesticides, FAO Plant Production and Protection Papers-173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur, et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.0001% and 98% by weight of active compound or, with particular preference, between 0.01% and 95% by weight of active compound, more preferably between 0.5% and 90% by weight of active compound, based on the weight of the formulation. The content of the active compound is defined as the sum of the recombinant exosporium-producing *Bacillus* cells and the further particular biological control agent described herein and/or a mutant of a particular microorganism strain described herein having all identifying characteristics of the respective strain, and/or at least one metabolite produced by the respective strain that exhibits activity against insects, mites, nematodes and/or phytopathogens, and fungicide and/or insecticide, if present.

The active compound content of the application forms (crop protection products) prepared from the formulations may vary within wide ranges. The active compound concentration of the application forms may be situated typically between 0.0001% and 95% by weight of active compound, preferably between 0.0001% and 1% by weight, based on the weight of the application form. Application takes place in a customary manner adapted to the application forms.

Furthermore, in one aspect of the present invention a kit of parts is provided comprising recombinant exosporium-producing *Bacillus* cells and at least one further particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount in a spatially separated arrangement.

In a further embodiment of the present invention the above-mentioned kit of parts further comprises at least one fungicide and/or at least one insecticide, with the proviso that the recombinant exosporium-producing *Bacillus* cells, insecticide and fungicide are not identical. The fungicide and/or the insecticide can be present either in the recombinant exosporium-producing *Bacillus cereus* family member-based biological control agent component of the kit of parts or in the component of the kit of parts comprising the particular biological control agent disclosed herein, being spatially separated or in both of these components. In one embodiment, the fungicide and the insecticide are present in the recombinant exosporium-producing *Bacillus cereus* family member-based biological control agent component.

Moreover, the kit of parts according to the present invention can additionally comprise at least one auxiliary selected from the group consisting of extenders, solvents, spontaneity promoters, carriers, emulsifiers, dispersants, frost protectants, thickeners and adjuvants as mentioned below. This at least one auxiliary can be present either in the recombinant exosporium-producing *Bacillus cereus* family member-based biological control agent component of the kit of parts or in the component of the kit of parts comprising the particular biological control agent disclosed herein, being spatially separated or in both of these components.

In another aspect of the present invention the composition as described above is used for reducing overall damage of plants and plant parts as well as losses in harvested fruits or vegetables caused by insects, mites, nematodes and/or phytopathogens.

Furthermore, in another aspect of the present invention the composition as described above increases the overall plant health.

The term "plant health" generally comprises various sorts of improvements of plants that are not connected to the control of pests. For example, advantageous properties that may be mentioned are improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tittering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

With regard to the use according to the present invention, improved plant health preferably refers to improved plant characteristics including: crop yield, more developed root system (improved root growth), improved root size maintenance, improved root effectiveness, tittering increase, increase in plant height, bigger leaf blade, less dead basal leaves, stronger tillers, greener leaf color, photosynthetic activity, more productive tillers, enhanced plant vigor, and increased plant stand.

With regard to the present invention, improved plant health preferably especially refers to improved plant properties selected from crop yield, more developed root system, improved root growth, improved root size maintenance, improved root effectiveness, tillering increase, and increase in plant height.

The effect of a composition according to the present invention on plant health as defined herein can be determined by comparing plants which are grown under the same environmental conditions, whereby a part of said plants is treated with a composition according to the present invention and another part of said plants is not treated with a composition according to the present invention. Instead, said other part is not treated at all or is treated with a placebo (i.e., an application without a composition according to the invention such as an application without all active ingredients (i.e., without the recombinant exosporium-producing *Bacillus* cells as described herein and without a further particular biological control agent as described herein), or an application without the recombinant exosporium-producing *Bacillus* cells as described herein, or an application without a further particular biological control agent disclosed herein.

The composition according to the present invention may be applied in any desired manner, such as in the form of a seed coating, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow (plant's locus of growth).

Reducing the overall damage of plants and plant parts often results in healthier plants and/or in an increase in plant vigor and yield.

Preferably, the composition according to the present invention is used for treating conventional or transgenic plants or seed thereof.

The present invention also relates to methods for stimulating plant growth using any of the compositions described above comprising recombinant exosporium-producing *Bacillus* cells that express a fusion protein and at least one of the further particular biological control agents described herein. The method for stimulating plant growth comprises applying to a plant, a plant part, to the locus surrounding the plant or in which the plant will be planted (e.g., soil or other growth medium) a composition comprising recombinant exosporium-producing *Bacillus* cells that express a fusion protein comprising: (i) at least one plant growth stimulating protein or peptide; and (ii) a targeting sequence, exosporium protein, or exosporium protein fragment, and at least one further particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount.

In another aspect of the present invention a method for reducing overall damage of plants and plant parts as well as losses in harvested fruits or vegetables caused by insects, mites, nematodes and/or phytopathogens is provided comprising the step of simultaneously or sequentially applying the recombinant exosporium-producing *Bacillus* cells and at least one further particular biological control agent described herein in a synergistically effective amount.

In one embodiment of the present method the composition further comprises at least one fungicide. In one aspect, the at least one fungicide is a synthetic fungicide. In a further aspect of this embodiment, the at least one fungicide is selected from the following group: bitertanol, bixafen, bromuconazole, carbendazim, carpropamid, dichlofluanid, fenamidone, fenhexamid, fentin acetate, fentin hydroxide, fluopicolide, fluopyram, fluoxastrobin, fluquinconazole, fosetyl, iprodione, iprovalicarb, isotianil, metominostrobin, ofurace, pencycuron, penflufen, prochloraz, propamocarb, propineb, prothioconazole, pyrimethanil, spiroxamine, tebuconazole, tolylfluanid, triadimefon, triadimenol, triazoxide, and trifloxystrobin.

In another embodiment, the composition comprises at least one insecticide in addition to the fungicide or in place of the fungicide, provided that the insecticide, the fungicide, the recombinant exosporium-producing *Bacillus* cells and the particular biological control agent disclosed herein are not identical.

In one embodiment, the at least one insecticide is a synthetic insecticide. In a further embodiment, the at least one insecticide is selected from the following group: acetamiprid, aldicarb, amitraz, beta-cyfluthrin, carbaryl, clothianidin, cyfluthrin, cypermethrin, deltamethrin, endosulfan, ethion, ethiprole, ethoprophos, fenamiphos, fenobucarb, fenthion, fipronil, flubendiamide, fluopyram, flupyradifurone, formetanate, heptanophos, imidacloprid, methamidophos, methiocarb, methomyl, niclosamide, oxydemeton-methyl, phosalone, silafluofen, spirodiclofen, spiromesifen, spirotetramat, thiacloprid, thiodicarb, tralomethrin, triazophos, triflumuron, and vamidothion.

The method of the present invention includes the following application methods, namely both of the recombinant exosporium-producing *Bacillus* cells and the at least one further particular biological control agent disclosed herein may be formulated into a single, stable composition with an agriculturally acceptable shelf life (so called "solo-formulation"), or being combined before or at the time of use (so called "combined-formulations").

If not mentioned otherwise, the expression "combination" stands for the various combinations of the recombinant exosporium-producing *Bacillus* cells and the at least one further particular biological control agent disclosed herein, and optionally the at least one fungicide and/or the at least one insecticide, in a solo-formulation, in a single "ready-mix" form, in a combined spray mixture composed from solo-formulations, such as a "tank-mix", and especially in a combined use of the single active ingredients when applied in a sequential manner, i.e., one after the other within a reasonably short period, such as a few hours or days, e.g., 2 hours to 7 days. The order of applying the composition according to the present invention is not essential for working the present invention. Accordingly, the term "combination" also encompasses the presence of the recombinant exosporium-producing *Bacillus* cells and the at least one further particular biological control agent disclosed herein, and optionally the at least one fungicide and/or insecticide on or in a plant to be treated or its surrounding, habitat or storage space, e.g., after simultaneously or consecutively applying the recombinant exosporium-producing *Bacillus* cells and the at least one further particular biological control agent disclosed herein, and optionally the at least one fungicide and/or the at least one insecticide to a plant its surrounding, habitat or storage space.

If the recombinant exosporium-producing *Bacillus* cells and the at least one further particular biological control agent described herein, and optionally the at least one fungicide and/or the at least one insecticide are employed or used in a sequential manner, it is preferred to treat the plants or plant parts (which includes seeds and plants emerging from the seed), harvested fruits and vegetables according to the following method: Firstly applying the at least one fungicide and/or the at least one insecticide on the plant or plant parts, and secondly applying the further particular biological control agent described herein and the recombinant exosporium-producing *Bacillus* cells to the same plant or plant parts. By this application manner the amount of residues of insecticides/fungicides on the plant upon harvesting is as low as possible. The time periods between the first and the second application within a (crop) growing cycle may vary and depend on the effect to be achieved. For example, the first application is done to prevent an infestation of the plant or plant parts with insects, mites, nematodes and/or phytopathogens (this is particularly the case when treating seeds) or to combat the infestation with insects, mites, nematodes and/or phytopathogens (this is particularly the case when treating plants and plant parts) and the second application is done to prevent or control the infestation with insects, mites, nematodes and/or phytopathogens and/or to promote plant growth. Control in this context means that the composition comprising the recombinant exosporium-producing *Bacillus* cells and the particular biological control agent disclosed herein are not able to fully exterminate the pests or phytopathogenic fungi but are able to keep the infestation on an acceptable level.

The present invention also provides methods of enhancing the killing, inhibiting, preventative and/or repelling activity of the compositions of the present invention by multiple applications. In some other embodiments, the compositions of the present invention are applied to a plant and/or plant part for two times, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. Still in some embodiments, the compositions of the present invention are applied to a plant and/or plant part for more than two times, for example, 3 times, 4 times, 5 times, 6 times, 7 times, 8 times, 9 times, 10 times, or more, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. The intervals between each application can vary if it is desired. One skilled in the art will be able to determine the application times and length of interval depending on plant species, plant pest species, and other factors.

By following the before mentioned steps, a very low level of residues of the at least one fungicide and/or at least one insecticide on the treated plant, plant parts, and the harvested fruits and vegetables can be achieved.

If not mentioned otherwise the treatment of plants or plant parts (which includes seeds and plants emerging from the seed), harvested fruits and vegetables with the composition according to the invention is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the recombinant exosporium-producing *Bacillus* cells, the at least one further particular biological control agent described herein, and optionally the at least one fungicide and/or the at least one insecticide as solo-formulation or combined-formulations by the ultra-low volume method, or to inject the composition according to the present invention as a composition or as sole-formulations into the soil (in-furrow).

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

The amount of the recombinant exosporium-producing *Bacillus* cells, which is used or employed in combination with at least one further particular biological control agent described herein, optionally in the presence of at least one fungicide and/or the at least one insecticide, depends on the final formulation as well as size or type of the plant, plant parts, seeds, harvested fruits and vegetables to be treated. Usually, the recombinant exosporium-producing *Bacillus* cells to be employed or used according to the invention is present in about 1% to about 80% (w/w), preferably in about 1% to about 60% (w/w), more preferably about 10% to about 50% (w/w) of its solo-formulation or combined-formulation with the at least one further particular biological control agent described herein, and optionally the fungicide and/or the at least one insecticide.

Also the amount of the at least one further particular biological control agent disclosed herein which is used or employed in combination with the recombinant exosporium-producing *Bacillus* cells, optionally in the presence of at least one fungicide and/or the at least one insecticide, depends on the final formulation as well as size or type of the plant, plant parts, seeds, harvested fruit or vegetable to be treated. Usually, the further particular biological control agent described herein to be employed or used according to the invention is present in about 0.1% to about 80% (w/w), preferably 1% to about 60% (w/w), more preferably about 10% to about 50% (w/w) of its solo-formulation or combined-formulation with the recombinant exosporium-producing *Bacillus* cells, and optionally the at least one fungicide and/or the at least one insecticide.

Application of the recombinant exosporium-producing *Bacillus* cells may be effected as a foliar spray, as a soil treatment, and/or as a seed treatment/dressing. When used as a foliar treatment, in one embodiment, about 1/16 to about 5 gallons of whole broth are applied per acre. When used as a soil treatment, in one embodiment, about 1 to about 5 gallons of whole broth are applied per acre. When used for seed treatment about 1/32 to about 1/4 gallons of whole broth are applied per acre. For seed treatment, the end-use formulation contains at least $1\times10^4$, at least $1\times10^5$, at least $1\times10^6$, $1\times10^7$, at least $1\times10^8$, at least $1\times10^9$, at least $1\times10^{10}$ colony forming units per gram.

The recombinant exosporium-producing *Bacillus* cells and at least one further particular biological control agent disclosed herein, and if present preferably also the fungicide and/or the insecticide are used or employed in a synergistic weight ratio. The skilled person is able to find out the synergistic weight ratios for the present invention by routine methods. The skilled person understands that these ratios refer to the ratio within a combined-formulation as well as to the calculative ratio of the recombinant exosporium-producing *Bacillus* cells described herein and the at least one further particular biological control agent disclosed herein when both components are applied as mono-formulations to a plant to be treated. The skilled person can calculate this ratio by simple mathematics since the volume and the amount of the recombinant exosporium-producing *Bacillus* cells and the at least one further particular biological control agent disclosed herein, respectively, in a mono-formulation is known to the skilled person.

The ratio can be calculated based on the amount of the at least one further particular biological control agent disclosed herein, at the time point of applying said component of a combination according to the invention to a plant or plant part and the amount of the recombinant exosporium-producing *Bacillus* cells shortly prior (e.g., 48 h, 24 h, 12 h, 6 h, 2 h, 1 h) or at the time point of applying said component of a combination according to the invention to a plant or plant part.

The application of the recombinant exosporium-producing *Bacillus* cells and the at least one further particular biological control agent disclosed herein to a plant or a plant part can take place simultaneously or at different times as long as both components are present on or in the plant after the application(s). In cases where the recombinant exosporium-producing *Bacillus* cells and further particular biological control agent disclosed herein are applied at different times and the further particular biological control agent disclosed herein is applied prior to the recombinant exosporium-producing *Bacillus* cells, the skilled person can determine the concentration of further particular biological control agent disclosed herein on/in a plant by chemical analysis known in the art, at the time point or shortly before the time point of applying the recombinant exosporium-producing *Bacillus* cells. Vice versa, when the recombinant exosporium-producing *Bacillus* cells is applied to a plant first, the concentration of the recombinant exosporium-producing *Bacillus* cells can be determined using tests which are also known in the art, at the time point or shortly before the time point of applying the further particular biological control agent disclosed herein.

In particular, in one embodiment the synergistic weight ratio of the recombinant exosporium-producing *Bacillus* cells (i.e., the unformulated spore preparation) and the at least one further particular biological control agent disclosed herein lies in the range of 1:1000 to 1000:1; in the range of 1:500 to 500:1; in the range of 1:300 to 500:1. Additional ratios are between 20:1 and 1:20, such as 10:1, 5:1 or 2:1. In embodiments in which the biological control agent is *Bacillus*-based the weight to weight ratio should be applied to the unformulated *Bacillus* spore preparation. In one aspect of this embodiment, the spore preparations of both the recombinant exosporium-producing *Bacillus* cells and the *Bacillus*-based biological control agent is dried spore preparation containing at least about $1\times10^4$ cfu/g, at least about $1\times10^5$ cfu/g, at least about $1\times10^6$ cfu/g at least about $1\times10^7$ cfu/g, at least about $1\times10^8$ cfu/g, at least about $1\times10^9$ cfu/g, at least about $1\times10^{10}$ cfu/g, and at least about $1\times10^{11}$ cfu/g. In another embodiment the colony forming unit to colony forming unit ratio of recombinant exosporium-producing *Bacillus* cells and the *Bacillus*-based particular biological control agent described herein lies in the range of 1:100,000 to 100,000 to 1, in the range of 1:10,000 to 10,000:1, in the range of 1:1000 to 1000:1, in the range of 1:500 to 500:1, in the range of 1:100 to 100:1, in the range of 1:10 to 10:1, in the range of 1:5 to 5:1, and in the range of 1:1.

In one embodiment of the present invention, the concentration of the recombinant exosporium-producing *Bacillus cereus* family member-based biological control agent after dispersal is at least 50 g/ha, such as 50-7500 g/ha, 50-2500 g/ha, 50-1500 g/ha; at least 250 g/ha (hectare), at least 500 g/ha or at least 800 g/ha.

The application rate of composition to be employed or used according to the present invention may vary. The skilled person is able to find the appropriate application rate by way of routine experiments.

In another aspect of the present invention a seed treated with the composition as described above is provided.

The control of insects, mites, nematodes and/or phytopathogens by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by insects, mites, nematodes and/or phytopathogens, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present invention therefore also relates in particular to a method for protecting seed and germinating plants from attack by pests, by treating the seed with the recombinant exosporium-producing *Bacillus* cells as defined above and at least one further biological control agent selected from particular microorganisms disclosed herein and/or a mutant of a specific strain of microorganism disclosed herein having all identifying characteristics of the respective strain, and/or at least one metabolite produced by the respective strain that exhibits activity against insects, mites, nematodes and/or phytopathogens and optionally at least one fungicide and/or optionally at least one insecticide of the invention. The method of the invention for protecting seed and germinating plants from attack by pests encompasses a method in which the seed is treated simultaneously in one operation with the recombinant exosporium-producing *Bacillus* cells and the at least one further particular biological control agent described herein, and optionally the at least one fungicide and/or the at least one insecticide. It also encompasses a method in which the seed is treated at different times with the recombinant exosporium-producing *Bacillus* cells and the at least one further particular biological control agent disclosed herein, and optionally the at least one fungicide and/or the at least one insecticide.

The invention likewise relates to the use of the composition of the invention for treating seed for the purpose of protecting the seed and the resultant plant against insects, mites, nematodes and/or phytopathogens.

The invention also relates to seed which at the same time has been treated with a the recombinant exosporium-producing *Bacillus* cells and at least one further particular biological control agent described herein, and optionally at least one fungicide and/or the at least one insecticide. The invention further relates to seed which has been treated at different times with the recombinant exosporium-producing *Bacillus* cells and the at least one further particular biological control agent disclosed herein and optionally the at least one fungicide and/or the at least one insecticide. In the case of seed which has been treated at different times with the recombinant exosporium-producing *Bacillus* cells and the at least one further particular biological control agent disclosed herein, and optionally the at least one fungicide and/or the at least one insecticide, the individual active ingredients in the composition of the invention may be present in different layers on the seed.

Furthermore, the invention relates to seed which, following treatment with the composition of the invention, is subjected to a film-coating process in order to prevent dust abrasion of the seed.

One of the advantages of the present invention is that, owing to the particular systemic properties of the compositions of the invention, the treatment of the seed with these compositions provides protection from insects, mites, nematodes and/or phytopathogens not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with composition of the invention, germination and emergence of the treated seed may be promoted.

It is likewise considered to be advantageous composition of the invention may also be used, in particular, on transgenic seed.

It is also stated that the composition of the invention may be used in combination with agents of the signalling technology, as a result of which, for example, colonization with symbionts is improved, such as rhizobia, mycorrhiza and/or endophytic bacteria, for example, is enhanced, and/or nitrogen fixation is optimized.

The compositions of the invention are suitable for protecting seed of any variety of plant which is used in agriculture, in greenhouses, in forestry or in horticulture. More particularly, the seed in question is that of cereals (e.g., wheat, barley, rye, oats and millet), maize, cotton, soybeans, rice, potatoes, sunflower, coffee, tobacco, canola, oilseed rape, beets (e.g., sugar beet and fodder beet), peanuts, vegetables (e.g., tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

As already mentioned above, the treatment of transgenic seed with the composition of the invention is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the composition of the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. Nos. 4,272,417 A; 4,245,432 A; 4,808,430 A; 5,876,739 A; U.S. Patent Publication No. 2003/0176428 A1; WO 2002/080675 A1; WO 2002/028186 A2.

The combinations which can be used in accordance with the invention may be converted into the customary seed-dressing formulations, such as solutions, emulsions, suspensions, powders, foams, slurries or other coating compositions for seed, and also ULV formulations.

These formulations are prepared in a known manner, by mixing composition with customary adjuvants, such as, for example, customary extenders and also solvents or diluents, colorants, wetters, dispersants, emulsifiers, antifoams, preservatives, secondary thickeners, stickers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetters which may be present in the seed-dressing formulations which can be used in accordance with the invention include all of the substances which promote wetting and which are customary in the formulation of active agrochemical ingredients. Use may be made preferably of alkylnaphthalenesulphonates, such as diisopropyl- or diisobutyl-naphthalenesulphonates.

Dispersants and/or emulsifiers which may be present in the seed-dressing formulations which can be used in accordance with the invention include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these. Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magnesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz—and Schädlingsbekämpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the recombinant exosporium-producing *Bacillus* cells and the at least one further particular biological control agent described herein in the formulations, and by the seed. The application rates in the case of the composition are situated generally at between 0.001 and 50 g per kilogram of seed, preferably between 0.01 and 15 g per kilogram of seed.

Furthermore, the composition according to the present invention preferably has potent microbicidal activity and can be used for control of unwanted microorganisms, such as fungi and bacteria, in crop protection and in the protection of materials.

The invention also relates to a method for controlling unwanted microorganisms, characterized in that the inventive composition is applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. *Oomycetes*), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;* diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondite, P. triticina, P. graminis* or *P. striiformis* or *P. hordei; Uromyces* species, for example *Uromyces appendiculatus;* diseases caused by pathogens from the group of the *Oomycetes*, for example *Albugo* species, for example *Algubo candida; Bremia* species, for example *Bremia lactucae; Peronospora* species, for example *Peronospora pisi, P. parasitica* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidia form: *Drechslera*, Syn: *Helminthosporium*), *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans, Leptosphaeria nodorum; Magnaporthe* species, for example *Magnaporthe grisea; Microdochium* species, for example *Microdochium nivale; Mycosphaerella* species, for example *Mycosphaerella graminicola, M. arachidicola* and *M. fijiensis; Phaeosphaeria* species, for example *Phaeosphaeria nodorum; Pyrenophora* species, for example *Pyrenophora teres, Pyrenophora tritici repentis; Ramularia* species, for example *Ramularia collo-cygni, Ramularia areola; Rhynchosporium* species, for example *Rhynchosporium secalis; Septoria* species, for example *Septoria apii, Septoria lycopersii; Typhula* species, for example *Typhula incarnata; Venturia* species, for example *Venturia inaequalis;* root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola;* ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum;* diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici;* fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticilium* species, for example *Verticilium alboatrum;* seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnata; Verticillium* species, caused for example by *Verticillium dahliae;* cancers, galls and witches' broom caused, for example, by *Nectria* species, for example *Nectria galligena;* wilt diseases caused, for example, by *Monilinia* species, for example *Monilinia laxa;* leaf blister or leaf curl diseases caused, for example, by *Exobasidium* species, for example *Exobasidium vexans;*

*Taphrina* species, for example *Taphrina deformans;* decline diseases of wooden plants caused, for example, by Esca disease, caused for example by *Phaemoniella clamydospora, Phaeoacremonium aleophilum* and *Fomitiporia mediterranea; Eutypa* dyeback, caused for example by *Eutypa lata; Ganoderma* diseases caused for example by

*Ganoderma boninense; Rigidoporus* diseases caused for example by *Rigidoporus lignosus;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;*

Club root caused, for example, by *Plasmodiophora* species, for example *Plamodiophora brassicae;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive compositions can be used for curative or protective/preventive control of phytopathogenic fungi. The invention therefore also relates to curative and protective methods for controlling phytopathogenic fungi by the use of the inventive composition, which is applied to the seed, the plant or plant parts, the fruit or the soil in which the plants grow.

The fact that the composition is well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive composition, when it is well tolerated by plants, has favourable homeotherm toxicity and is well tolerated by the environment, is suitable for protecting plants and plant organs, for enhancing harvest yields, for improving the quality of the harvested material. It can preferably be used as crop protection composition. It is active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g., canola, rapeseed), *Brassica rapa, B. juncea* (e.g., (field) mustard) and *Brassica carinata, Arecaceae* sp. (e.g., oilpalm, coconut), rice, wheat, sugar beet, sugar cane, oats, rye, barley, millet and sorghum, triticale, flax, nuts, grapes and vine and various fruit and vegetables from various botanic taxa, e.g., *Rosaceae* sp. (e.g., pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g., olive tree), Actinidaceae sp., Lauraceae sp. (e.g., avocado, cinnamon, camphor), Musaceae sp. (e.g., banana trees and plantations), Rubiaceae sp. (e.g., coffee), Theaceae sp. (e.g., tea), Sterculiceae sp., Rutaceae sp. (e.g., lemons, oranges, mandarins and grapefruit); Solanaceae sp. (e.g., tomatoes, potatoes, peppers, capsicum, aubergines, tobacco), Liliaceae sp., Compositae sp. (e.g., lettuce, artichokes and chicory—including root chicory, endive or common chicory), Umbelliferae sp. (e.g., carrots, parsley, celery and celeriac), Cucurbitaceae sp. (e.g., cucumbers—including gherkins, pumpkins, watermelons, calabashes and melons), Alliaceae sp. (e.g., leeks and onions), Cruciferae sp. (e.g., white cabbage, red cabbage, broccoli, cauliflower, Brussels sprouts, pak choi, kohlrabi, radishes, horseradish, cress and chinese cabbage), Leguminosae sp. (e.g., peanuts, peas, lentils and beans—e.g., common beans and broad beans), Chenopodiaceae sp. (e.g., Swiss chard, fodder beet, spinach, beetroot), Linaceae sp. (e.g., hemp), Cannabeacea sp. (e.g., cannabis), Malvaceae sp. (e.g., okra, cocoa), Papaveraceae (e.g., poppy), Asparagaceae (e.g., asparagus); useful plants and ornamental plants in the garden and woods including turf, lawn, grass and *Stevia rebaudiana*; and in each case genetically modified types of these plants.

Depending on the plant species or plant cultivars, their location and growth conditions (soils, climate, vegetation period, diet), using or employing the composition according to the present invention the treatment according to the invention may also result in super-additive ("synergistic") effects. Thus, for example, by using or employing inventive composition in the treatment according to the invention, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the inventive composition in the treatment according to the invention may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses. Thus, by using or employing composition according to the present invention in the treatment according to the invention, plants can be protected against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are also preferably to be treated according to the invention are resistant against one or more biotic stresses, i.e., said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses, i.e., that already exhibit an increased plant health with respect to stress tolerance. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance. Preferably, the treatment of these plants and cultivars with the composition of the present invention additionally increases the overall plant health (cf. above).

Plants and plant cultivars which may also be treated according to the invention, are those plants characterized by enhanced yield characteristics, i.e., that already exhibit an increased plant health with respect to this feature. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation.

Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability. Preferably, the treatment of these plants and cultivars with the composition of the present invention additionally increases the overall plant health (cf. above).

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g., in corn) be produced by detasseling, i.e., the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e., plants made tolerant to one or more given herbicides. Such plants can be obtained either by genetic transformation, or by selection of plants containing a mutation imparting such herbicide tolerance.

The following non-limiting examples are provided to further illustrate the present invention.

EXAMPLES

Example 1

Formula for the Efficacy of the Combination of Multiple Active Ingredients

A synergistic effect of active ingredients is present when the activity of the active ingredient combinations exceeds the total of the activities of the active ingredients when applied individually. The expected activity for a given combination of two active ingredients can be calculated as follows (cf. Colby, S. R., "Calculating Synergistic and Antagonistic Responses of Herbicide Combinations," *Weeds* 1967, 15, 20-22):

If

X is the efficacy when active ingredient A is applied at an application rate of m ppm (or g/ha), Y is the efficacy when active ingredient B is applied at an application rate of n ppm (or g/ha), E is the efficacy when the active ingredients A and B are applied at application rates of m and n ppm (or g/ha), respectively, and then $$E = X + Y - \frac{X \cdot Y}{100}$$

If the actual activity exceeds the calculated value, then the activity of the combination is superadditive, i.e., a synergistic effect exists. In this case, the efficacy which was actually observed must be greater than the value for the expected efficacy (E) calculated from the above-mentioned formula.

For instance, the formula and analysis can be applied to an evaluation of plant growth promotion. Such an assay is evaluated several days after the applications to plants. 100% means plant weight which corresponds to that of the untreated control plant. Efficacy means in this case the additional % of plant weight in comparison to that of the untreated control. For example, a treatment that resulted in plant weights that were 120% compared to the untreated control plant would have an efficacy of 20%. If the plant growth promotion effect for the combination (i.e., the observed efficacy for % shoot weights of plants treated with the combination) exceeds the calculated value, then the activity of the combination is superadditive, i.e., a synergistic effect exists.

The formula and analysis can also be used to evaluate synergy in disease control assays. The degree of efficacy expressed in % is denoted. 0% means an efficacy which corresponds to that of the control while an efficacy of 100% means that no disease is observed.

If the actual insecticidal or fungicidal activity exceeds the calculated value, then the activity of the combination is superadditive, i.e., a synergistic effect exists. In this case, the efficacy which is actually observed must be greater than the value for the expected efficacy (E) calculated from the above-mentioned formula.

A further way of demonstrating a synergistic effect is the method of Tammes (cf. "Isoboles, A Graphic Representation of Synergism in Pesticides," in *Neth. J. Plant Path.,* 1964, 70, 73-80).

Example 2

Plant Growth Promotion with *Bacillus subtilis* QST713 and Recombinant *Bacillus thuringiensis* Cells Expressing Phospholipase C Experiments were conducted to analyze efficacy of a combination of *Bacillus subtilis* QST713-based product and a fermentation product of recombinant *Bacillus thuringiensis* cells expressing phospholipase C ("BEPC"). Maize seeds were grown in sterile mixture of synthetic media and sand in small three-inch square pots on light racks in a plant growth room at 25-28° C. and 50% humidity for about 14 days. Two seeds were planted in each pot. At planting, the growing media in each pot was drenched with the treatments described below. After 14 days, plants were measured for whole plant biomass. In some experiments, roots were analyzed using the WinRhizo Root scanner. In all tables throughout these Examples, UTC refers to untreated control. "Calculated" refers to the expected effect calculated using the above-described Colby equation and "Efficacy" refers to the actual effect observed.

The SERENADE® ASO product was diluted in water (1% and 5% volume to volume) and the diluted solution was used to drench the growing media. The application rate of SERENADE® ASO refers to the amount of *Bacillus subtilis* QST713 (i.e., spore preparation) contained in the product SERENADE® ASO, which is 1.34%. The formulated product has a minimum spore concentration of $1 \times 10^9$ cfu/g.

A recombinant *Bacillus cereus* family member (*Bacillus thuringiensis* BT013A) expressing phospholipase C on its exosporium (BEPC) was generated as follows. To generate plasmids for expression of fusion proteins in *Bacillus cereus* family members, PCR fragments were generated that encoded the Bc1A promoter (SEQ ID NO: 85), a methionine start codon, and amino acids 20-35 of Bc1A (SEQ ID NO: 1) followed by a six alanine linker sequence fused in frame to *Bacillus thuringiensis* BT013A phospholipase C (SEQ ID NO: 108). These PCR fragments were digested with Xho1 and ligated into the Sall site of the pSUPER plasmid to generate the plasmids pSUPER-Bc1A 20-35-Phospholipase. The pSUPER plasmid was generated through fusion of the pUC57 plasmid (containing an ampicillin resistance cassette) with the pBC16-1 plasmid from *Bacillus* (containing a tetracycline resistance). This 5.5 kbp plasmid can replicate in both *E. coli* and *Bacillus* spp. The pSUPER-Bc1A 20-35-Phospholipase plasmids were transformed into and propagated in dam methylase negative *E. coli* strains and finally were transformed into *Bacillus thuringiensis* BT013A.

To obtain whole broth cultures of BEPC, 15 mL conicals containing brain heart infusion media (BHI) were inoculated with BEPC and grown for 7-8 hours at around 30° C. at a shaker setting of 300 rpm. The next day, 250 μl aliquots from each flask were inoculated into 250 mL flasks containing 50 mL of a yeast extract-based media and grown at about 30° C. After approximately 2 days of incubation, when sporulation was at least 95% completed, the culture broth was harvested and colony forming units calculated. The fermentation broth was diluted to 5% in 50 mL water and the following colony forming units applied to each pot.

TABLE 3

| Treatment | Application Rate PPM and/or CFU/pot | Whole Plant Biomass (g) | Found % | Efficacy % | Calculated % |
|---|---|---|---|---|---|
| UTC | | 3.23 | 100 | | |
| SERENADE ® ASO 5% | 703<br>$2.62 \times 10^9$ | 4.71 | 146 | 46 | |
| *Bacillus* expressing phospholipase C (BEPC) 5% | $7 \times 10^8$ CFU/pot | 3.83 | 118 | 18 | |
| SERENADE ® ASO 5% + BEPC | $2.62 \times 10^9$ + $7 \times 10^8$ | 5.33 | 165 | 65 | 55.72 |

The experiment was repeated as above but with a 1% dilution of the SERENADE® ASO product. Results are shown in Table 4, below.

TABLE 4

| Treatment | Application Rate | Whole Plant Biomass (g) | Found % | Efficacy % | Calculated % |
|---|---|---|---|---|---|
| UTC | | 3.22 | 100 | | |
| SERENADE ® ASO 1% | 140.7 PPM $5.24 \times 10^8$ CFU/pot | 3.62 | 112 | 12 | |
| BEPC | $7 \times 10^8$ CFU/pot | 3.76 | 117 | 17 | |
| SERENADE ® ASO 1% + BEPC | $5.24 \times 10^8$ CFU/pot + $7 \times 10^8$ CFU/pot | 4.26 | 132 | 32 | 26.96 |

Results of root volume measurements using the WinRhizo root scanner are shown in Table 5.

TABLE 5

| | Root Volume Average | % Found | % Efficacy | % Calculated |
|---|---|---|---|---|
| UTC | 5.259 | 100.0 | 0.0 | |
| SERENADE ® ASO 1% | 6.282 | 119.5 | 19.5 | |
| BEPC 5% | 6.249 | 118.8 | 18.8 | |
| Ser 1% and BEPC 5% | 9.318 | 177.2 | 77.2 | 34.6 |

Results indicate a superadditive plant yield effect when combining SERENADE® ASO and BEPC.

Example 3

Plant Growth Promotion with *Bacillus subtilis* QST713 and Recombinant *Bacillus thuringiensis* Cells Expressing Endoglucanase Experiments similar to those in Example 2 were conducted using a recombinant *Bacillus thuringiensis* cells expressing endoglucanase (SEQ ID NO: 107), referred to in these examples as BEE. Whole broth cultures of BEE were created as described above, except that endoglucanase (SEQ ID NO: 107), rather than phosphpolipase, was used. Effects on plant yield of combinations of BEE with SERENADE® ASO are shown in the tables below.

TABLE 6

| Treatment | Application Rate | Whole Plant Biomass (g) | Found % | Efficacy % | Calculated % |
|---|---|---|---|---|---|
| UTC | | 3.23 | 100 | | |
| SERENADE ® ASO 5% | 703 PPM $2.62 \times 10^9$ CFU/pot | 4.71 | 146 | 46 | |
| BEE 5% | $7.85 \times 10^8$ CFU/pot | 3.7 | 114 | 14 | |

TABLE 6-continued

| Treatment | Application Rate | Whole Plant Biomass (g) | Found % | Efficacy % | Calculated % |
|---|---|---|---|---|---|
| SERENADE ® ASO 5% + BEE 5% | $2.62 \times 10^9$ CFU/pot + $7.85 \times 10^8$ CFU/pot | 5.89 | 182 | 82 | 53.56 |

TABLE 7

| Treatment | Application Rate | Whole Plant Biomass (g) | Found % | Efficacy % | Calculated % |
|---|---|---|---|---|---|
| UTC | | 3.22 | 100 | | |
| SERENADE ® ASO 1% | 140.7 PPM $5.24 \times 10^8$ CFU/pot | 3.62 | 112 | 12 | |
| BEE 5% | $7.85 \times 10^8$ CFU/pot | 3.92 | 121 | 21 | |
| SERENADE ® ASO 1% + BEE 5% | $5.24 \times 10^8$ CFU/pot + $7.85 \times 10^8$ CFU/pot | 4.40 | 136 | 36 | 30.48 |

TABLE 8

| | Root Volume Average | % Found | % Efficacy | % Calculated |
|---|---|---|---|---|
| UTC | 5.259 | 100.0 | 0.0 | |
| SERENADE ® ASO 1% | 6.282 | 119.5 | 19.5 | |
| BEE 5% | 6.704 | 127.5 | 27.5 | |
| Ser 1% and BEE 5% | 8.209 | 156.1 | 56.1 | 41.6 |

The above results show a superadditive effect on plant yield when *Bacillus subtilis* QST713 and BEE are applied in combination.

Example 4

Plant Growth Promotion with *Bacillus firmus* strain I-1582 and Recombinant *Bacillus thuringiensis* Cells Maize seeds will be grown in loamy sand in the greenhouse at 20° C. and 70% humidity for about 11 days. After about 11 days from the time of treatment the seedlings will be cut off above the soil and the fresh weight will be determined.

Recombinant *Bacillus thuringiensis* cells expressing an endoglucanase encoded by SEQ ID NO: 107 or a phospholipase C encoded by SEQ ID NO: 108 and prepared as described above will be applied at about 50 μg/kernel. *Bacillus firmus* strain I-1582 will also be applied at about 50 μg/kernel.

It is expected that the maize plants treated with the recombinant *Bacillus thuringiensis* in combination with the *Bacillus firmus* strain I-1582 will have % shoot weights that exceed the calculated value based on the % shoot weights from the maize plants treated with the two active ingredients alone, i.e., a synergistic effect will be observed.

What is claimed is:

1. A composition comprising:

a) recombinant cells of a *Bacillus cereus* family member, wherein the cells express a fusion protein comprising:

(i) at least one plant growth stimulating protein or peptide selected from the group consisting of a polypeptide having endoglucanase activity and at least 85% sequence identity to SEQ ID NO: 107 and a polypeptide having phospholipase activity and at least 85% sequence identity to SEQ ID NO: 108; and (ii) a targeting sequence, exosporium protein, or exosporium protein fragment that is capable of targeting the fusion protein to the exosporium of the recombinant *Bacillus cereus* family member, comprising:

an amino acid sequence having at least 43% identity with amino acids 20-35 of SEQ ID NO: 1, wherein the identity with amino acids 25-35 is at least 54%;

amino acids 1-35 of SEQ ID NO: 1;

amino acids 20-35 of SEQ ID NO: 1;

amino acids 22-31 of SEQ ID NO: 1;

amino acids 22-33 of SEQ ID NO: 1;

amino acids 20-31 of SEQ ID NO: 1;

the amino acid sequence of SEQ ID NO: 1; or an amino acid sequence having at least 85% sequence identity to SEQ ID NO: 2; and b) a *Bacillus firmus* strain in a synergistic weight ratio in the range of 1:1000 to 1000:1, wherein the synergism refers to the effect of enhancing plant growth and/or promoting plant health.

2. The composition according of claim 1, wherein the *Bacillus cereus* family member is selected from the group consisting of *Bacillus anthracis; Bacillus cereus, Bacillus thuringiensis, Bacillus mycoides, Bacillus pseudomycoides, Bacillus samanil, Bacillus gaemokensis, Bacillus weihenstephensis, Bacillus toyoiensis* and combinations thereof.

3. The composition of claim 1, wherein the fusion protein comprises SEQ ID NO: 107.

4. The composition of claim 1, wherein the recombinant *Bacillus* cells are from *Bacillus thuringiensis* BT013A.

5. The composition of claim 1, wherein the fusion protein comprises SEQ ID NO: 108.

6. The composition according to claim 1, wherein the fusion protein is expressed under the control of a sporulation promoter native to the targeting sequence, exosporium protein or exosporium protein fragment of the fusion protein.

7. The composition according to claim 1, wherein the *Bacillus firmus* strain is *Bacillus firmus* strain 1-1582.

8. A method of treating a plant, a plant part, or the locus surrounding the plant to enhance plant growth and/or promote plant health comprising applying the composition according to claim 1.

9. The composition of claim 1 wherein the at least one plant growth stimulating protein or peptide is endoglucanase with at least 90% sequence identity to SEQ ID NO: 107.

10. The composition of claim 1 wherein the at least one plant growth stimulating protein or peptide is endoglucanase with at least 95% sequence identity to SEQ ID NO: 107.

11. The composition of claim 1 wherein the at least one plant growth stimulating protein or peptide is endoglucanase with at least 98% sequence identity to SEQ ID NO: 107.

12. The composition of claim 1 wherein the at least one plant growth stimulating protein or peptide is phospholipase with at least 90% sequence identity to SEQ ID NO: 108.

13. The composition of claim 1 wherein the at least one plant growth stimulating protein or peptide is phospholipase with at least 95% sequence identity to SEQ ID NO: 108.

14. The composition of claim 1 wherein the at least one plant growth stimulating protein or peptide is phospholipase with at least 98% sequence identity to SEQ ID NO: 108.

15. The composition of claim 11 wherein the targeting sequence comprises amino acids 20-35 of SEQ ID NO:1.

16. The composition of claim 14 wherein the targeting sequence comprises amino acids 20-35 of SEQ ID NO:1.

17. The composition of claim 15 wherein the *Bacillus firmus* strain is *Bacillus firmus* strain 1-1582.

18. The composition of claim 16 wherein the *Bacillus firmus* strain is *Bacillus firmus* strain 1-1582.

* * * * *

SEQUENCE LISTING

<160> NUMBER OF SEQ ID NOS: 109

<210> SEQ ID NO 1
<211> LENGTH: 41
<212> TYPE: PRT
<213> ORGANISM: Bacillus anthracis

<400> SEQUENCE: 1

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40
```

<210> SEQ ID NO 2
<211> LENGTH: 332
<212> TYPE: PRT
<213> ORGANISM: Bacillus anthracis

<400> SEQUENCE: 2

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
        195                 200                 205

Ile Ser Leu Asp Leu Gly Ile Asn Asp Pro Val Pro Phe Asn Thr Val
    210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
```

```
        275                 280                 285

Pro Phe Thr Ile Val Ile Gln Ala Ile Thr Gln Ile Thr Thr Thr Pro
    290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
                325                 330


<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly


<210> SEQ ID NO 4
<211> LENGTH: 209
<212> TYPE: PRT
<213> ORGANISM: Bacillus anthracis

<400> SEQUENCE: 4

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
                85                  90                  95

Thr Asn Ile Asn Phe Thr Leu Pro Gly Pro Val Ser Gly Thr Thr Leu
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp


<210> SEQ ID NO 5
<211> LENGTH: 44
```

<212> TYPE: PRT
<213> ORGANISM: Bacillus anthracis

<400> SEQUENCE: 5

```
Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40
```

<210> SEQ ID NO 6
<211> LENGTH: 647
<212> TYPE: PRT
<213> ORGANISM: Bacillus anthracis

<400> SEQUENCE: 6

```
Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
        115                 120                 125

Gly Ser Thr Gly Val Thr Gly Ser Thr Gly Ala Thr Gly Ser Thr Gly
    130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
        275                 280                 285

Glu Thr Gly Glu Thr Gly Gly Thr Gly Ser Thr Gly Pro Thr Gly Asn
    290                 295                 300
```

Thr Gly Ala Thr Gly Ser Thr Gly Val Thr Gly Ser Thr Gly Val Thr
305 310 315 320

Gly Ser Thr Gly Val Thr Gly Glu Thr Gly Pro Thr Gly Ser Thr Gly
325 330 335

Ala Thr Gly Asn Thr Gly Pro Thr Gly Glu Thr Gly Gly Thr Gly Ser
340 345 350

Thr Gly Ala Thr Gly Ser Thr Gly Val Thr Gly Asn Thr Gly Pro Thr
355 360 365

Gly Ser Thr Gly Val Thr Gly Asn Thr Gly Ala Thr Gly Glu Thr Gly
370 375 380

Pro Thr Gly Asn Thr Gly Ala Thr Gly Asn Thr Gly Pro Thr Gly Glu
385 390 395 400

Thr Gly Val Thr Gly Ser Thr Gly Pro Thr Gly Glu Thr Gly Val Thr
405 410 415

Gly Ser Thr Gly Pro Thr Gly Asn Thr Gly Ala Thr Gly Glu Thr Gly
420 425 430

Ala Thr Gly Ser Thr Gly Val Thr Gly Asn Thr Gly Ser Thr Gly Glu
435 440 445

Thr Gly Pro Thr Gly Ser Thr Gly Pro Thr Gly Ser Thr Gly Ala Thr
450 455 460

Gly Val Thr Gly Asn Thr Gly Pro Thr Gly Ser Thr Gly Ala Thr Gly
465 470 475 480

Ala Thr Gly Ser Thr Gly Pro Thr Gly Ser Thr Gly Thr Thr Gly Asn
485 490 495

Thr Gly Val Thr Gly Asp Thr Gly Pro Thr Gly Ala Thr Gly Val Ser
500 505 510

Thr Thr Ala Thr Tyr Ala Phe Ala Asn Asn Thr Ser Gly Ser Val Ile
515 520 525

Ser Val Leu Leu Gly Gly Thr Asn Ile Pro Leu Pro Asn Asn Gln Asn
530 535 540

Ile Gly Pro Gly Ile Thr Val Ser Gly Gly Asn Thr Val Phe Thr Val
545 550 555 560

Ala Asn Ala Gly Asn Tyr Tyr Ile Ala Tyr Thr Ile Asn Leu Thr Ala
565 570 575

Gly Leu Leu Val Ser Ser Arg Ile Thr Val Asn Gly Ser Pro Leu Ala
580 585 590

Gly Thr Ile Asn Ser Pro Thr Val Ala Thr Gly Ser Phe Ser Ala Thr
595 600 605

Ile Ile Ala Ser Leu Pro Ala Gly Ala Ala Val Ser Leu Gln Leu Phe
610 615 620

Gly Val Val Ala Leu Ala Thr Leu Ser Thr Ala Thr Pro Gly Ala Thr
625 630 635 640

Leu Thr Ile Ile Arg Leu Ser
645

<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1 5 10 15

Glu Asn Ile Gly Pro Thr Phe Pro Val Leu Pro Pro Ile His Ile Pro
20 25 30

Thr Gly

<210> SEQ ID NO 8
<211> LENGTH: 366
<212> TYPE: PRT
<213> ORGANISM: Bacillus anthracis

<400> SEQUENCE: 8

```
Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110

Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365
```

<210> SEQ ID NO 9
<211> LENGTH: 30
<212> TYPE: PRT
<213> ORGANISM: Bacillus anthracis

<400> SEQUENCE: 9

```
Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly
            20                  25                  30
```

<210> SEQ ID NO 10
<211> LENGTH: 77
<212> TYPE: PRT
<213> ORGANISM: Bacillus anthracis

<400> SEQUENCE: 10

```
Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly Pro Thr
            20                  25                  30

Gly Ser Thr Gly Ala Lys Gly Ala Ile Gly Asn Thr Glu Pro Tyr Trp
        35                  40                  45

His Thr Gly Pro Pro Gly Ile Val Leu Leu Thr Tyr Asp Phe Lys Ser
    50                  55                  60

Leu Ile Ile Ser Phe Ala Phe Arg Ile Leu Pro Ile Ser
65                  70                  75
```

<210> SEQ ID NO 11
<211> LENGTH: 39
<212> TYPE: PRT
<213> ORGANISM: Bacillus weihenstephensis

<400> SEQUENCE: 11

```
Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35
```

<210> SEQ ID NO 12
<211> LENGTH: 299
<212> TYPE: PRT
<213> ORGANISM: Bacillus weihenstephensis

<400> SEQUENCE: 12

```
Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Val Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
```

```
                85                  90                  95

Val Thr Gly Pro Thr Gly Val Thr Gly Pro Thr Gly Val Thr Gly Pro
            100                 105                 110

Thr Gly Val Thr Gly Pro Thr Gly Val Thr Gly Pro Thr Gly Glu Thr
        115                 120                 125

Gly Pro Thr Gly Gly Thr Glu Gly Cys Leu Cys Asp Cys Cys Val Leu
    130                 135                 140

Pro Met Gln Ser Val Leu Gln Gln Leu Ile Gly Glu Thr Val Ile Leu
145                 150                 155                 160

Gly Thr Ile Ala Asp Thr Pro Asn Thr Pro Pro Leu Phe Phe Leu Phe
                165                 170                 175

Thr Ile Thr Ser Val Asn Asp Phe Leu Val Thr Val Thr Asp Gly Thr
            180                 185                 190

Thr Thr Phe Val Val Asn Ile Ser Asp Val Thr Gly Val Gly Phe Leu
        195                 200                 205

Pro Pro Gly Pro Pro Ile Thr Leu Leu Pro Pro Thr Asp Val Gly Cys
    210                 215                 220

Glu Cys Glu Cys Arg Glu Arg Pro Ile Arg Gln Leu Leu Asp Ala Phe
225                 230                 235                 240

Ile Gly Ser Thr Val Ser Leu Leu Ala Ser Asn Gly Ser Ile Ala Ala
                245                 250                 255

Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285

Ile Thr Ala Val Asn Ile Thr Pro Ile Thr Met
    290                 295


<210> SEQ ID NO 13
<211> LENGTH: 39
<212> TYPE: PRT
<213> ORGANISM: Bacillus weihenstephensis

<400> SEQUENCE: 13

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly
        35


<210> SEQ ID NO 14
<211> LENGTH: 289
<212> TYPE: PRT
<213> ORGANISM: Bacillus weihenstephensis

<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
```

65 70 75 80

Gly Pro Thr Gly Pro Thr Gly Leu Thr Gly Pro Thr Gly Leu Thr Gly
85 90 95

Pro Thr Gly Pro Thr Gly Leu Thr Gly Gln Thr Gly Ser Thr Gly Pro
100 105 110

Thr Gly Ala Thr Glu Gly Cys Leu Cys Asp Cys Cys Val Phe Pro Met
115 120 125

Gln Glu Val Leu Arg Gln Leu Val Gly Gln Thr Val Ile Leu Ala Thr
130 135 140

Ile Ala Asp Ala Pro Asn Val Ala Pro Arg Phe Phe Leu Phe Asn Ile
145 150 155 160

Thr Ser Val Asn Asp Phe Leu Val Thr Val Thr Asp Pro Val Ser Asn
165 170 175

Thr Thr Phe Val Val Asn Ile Ser Asp Val Ile Gly Val Gly Phe Ser
180 185 190

Leu Thr Val Pro Pro Leu Thr Leu Leu Pro Pro Ala Asp Leu Gly Cys
195 200 205

Glu Cys Asp Cys Arg Glu Arg Pro Ile Arg Glu Leu Leu Asp Thr Leu
210 215 220

Ile Gly Ser Thr Val Asn Leu Leu Val Ser Asn Gly Ser Ile Ala Thr
225 230 235 240

Gly Phe Asn Val Glu Gln Thr Ala Leu Gly Ile Val Ile Gly Thr Leu
245 250 255

Pro Ile Pro Ile Asn Pro Pro Pro Pro Thr Leu Phe Arg Phe Ala Ile
260 265 270

Ser Thr Cys Lys Ile Thr Ala Val Asp Ile Thr Pro Thr Pro Thr Ala
275 280 285

Thr

<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1 5 10 15

Arg Phe Asn Ser Pro Lys Ile Lys Ser Glu Ile Ser Ile Ser Pro Asp
20 25 30

Leu Val Gly Pro Thr Phe Pro Pro Ile Pro Ser Phe Thr Leu Pro Thr
35 40 45

Gly

<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1 5 10 15

Arg Phe Asn Ser Pro Lys Ile Lys Ser Glu Ile Ser Ile Ser Pro Asp
20 25 30

Leu Val Gly Pro Thr Phe Pro Pro Ile Pro Ser Phe Thr Leu Pro Thr
35 40 45

```
Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140

Gly Thr Pro Gln Leu Glu Ile Thr Thr Ile Ile Asp Leu Leu Ala Ser
145                 150                 155                 160

Gln Thr Ile Asp Ile Gln Phe Ser Ala Ala Glu Ser Gly Thr Leu Thr
                165                 170                 175

Val Gly Ser Ser Asn Phe Phe Ser Gly Ala Leu Leu Pro
            180                 185


<210> SEQ ID NO 17
<211> LENGTH: 33
<212> TYPE: PRT
<213> ORGANISM: Bacillus cereus

<400> SEQUENCE: 17

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly


<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Pro Thr Gly Ile Gly Ile Thr
65                  70                  75                  80

Gly Pro Thr Gly


<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1               5                   10                  15
```

-continued

```
Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350
```

```
Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Leu Thr Gly Ser Gln Gly Pro Thr Gly
    690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765
```

```
Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Glu Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Ala Thr Gly Val Thr
    930                 935                 940

Gly Leu Gln Gly Pro Gln Gly Ile Gln Gly Val Gln Gly Glu Ile Gly
945                 950                 955                 960

Pro Thr Gly Pro Gln Gly Ile Gln Gly Pro Gln Gly Ile Gln Gly Val
                965                 970                 975

Thr Gly Ala Thr Gly Ala Gln Gly Pro Gln Gly Ile Gln Gly Pro Gln
            980                 985                 990

Gly Asp Ile Gly Pro Thr Gly Ser  Gln Gly Ile Gln Gly  Pro Gln Gly
        995                 1000                 1005

Pro Gln  Gly Ile Gln Gly Ala  Thr Gly Ala Thr Gly  Ala Gln Gly
    1010                 1015                 1020

Pro Gln  Gly Ile Gln Gly Pro  Gln Gly Glu Ile Gly  Pro Thr Gly
    1025                 1030                 1035

Pro Gln  Gly Pro Gln Gly Ile  Gln Gly Pro Gln Gly  Ile Gln Gly
    1040                 1045                 1050

Pro Thr  Gly
    1055
```

<210> SEQ ID NO 21
<211> LENGTH: 39
<212> TYPE: PRT
<213> ORGANISM: Bacillus weihenstephensis

<400> SEQUENCE: 21

```
Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly
        35
```

<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly Ser Thr Gly Pro Thr Gly Ser Thr Gly
        35                  40                  45

Ser Thr Gly Pro Thr Gly Ser Thr Gly Asn Thr Gly Pro Thr Gly Pro
    50                  55                  60

Thr Gly Pro Pro Val Gly Thr Asn Leu Asp Thr Ile Tyr Val Thr Asn
65                  70                  75                  80

Asp Ile Ser Asn Asn Val Ser Ala Ile Asp Gly Asn Thr Asn Thr Val
                85                  90                  95

Leu Thr Thr Ile Pro Val Gly Thr Asn Pro Val Gly Val Gly Val Asn
            100                 105                 110

Ser Ser Thr Asn Leu Ile Tyr Val Val Asn Asn Gly Ser Asp Asn Ile
        115                 120                 125

Ser Val Ile Asn Gly Ser Thr Asn Thr Val Val Ala Thr Ile Pro Val
    130                 135                 140

Gly Thr Gln Pro Phe Gly Val Gly Val Asn Pro Ser Thr Asn Leu Ile
145                 150                 155                 160

Tyr Val Ala Asn Arg Thr Ser Asn Asn Val Ser Val Ile Lys Gly Gly
                165                 170                 175

Thr Asn Thr Val Leu Thr Thr Ile Pro Val Gly Thr Asn Pro Val Gly
            180                 185                 190

Val Gly Val Asn Ser Ser Thr Asn Leu Ile Tyr Val Thr Asn Glu Ile
        195                 200                 205

Pro Asn Ser Val Ser Val Ile Lys Gly Gly Thr Asn Thr Val Val Ala
    210                 215                 220

Thr Ile Pro Val Gly Leu Phe Pro Phe Gly Val Gly Val Asn Ser Leu
225                 230                 235                 240

Thr Asn Leu Ile Tyr Val Val Asn Asn Ser Pro His Asn Val Ser Val
                245                 250                 255

Ile Asp Gly Asn Thr Asn Thr Val Leu Thr Thr Ile Ser Val Gly Thr
            260                 265                 270

Ser Pro Val Gly Val Gly Val Asn Leu Ser Thr Asn Leu Ile Tyr Val
        275                 280                 285

Ala Asn Glu Val Pro Asn Asn Ile Ser Val Ile Asn Gly Asn Thr Asn
    290                 295                 300

Thr Val Leu Thr Thr Ile Pro Val Gly Thr Thr Pro Phe Glu Val Gly
305                 310                 315                 320

Val Asn Ser Ser Thr Asn Leu Ile Tyr Val Ser Asn Leu Asn Ser Asn
                325                 330                 335

Asn Val Ser Val Ile Asn Gly Ser Ala Asn Thr Val Ile Ala Thr Val
            340                 345                 350

Pro Val Gly Ser Val Pro Arg Gly Ile Gly Val Lys Pro
        355                 360                 365

<210> SEQ ID NO 23
<211> LENGTH: 30
<212> TYPE: PRT
<213> ORGANISM: Bacillus weihenstephensis

<400> SEQUENCE: 23

```
Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly
            20                  25                  30


<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1               5                   10                  15

Pro Thr Leu Pro Pro Val Pro Pro Phe Gln Phe Pro Thr Gly Pro Thr
            20                  25                  30

Gly Ser Thr Gly Ser Thr Gly Pro Thr Gly Ser Thr Gly Ser Thr Gly
        35                  40                  45

Pro Thr Gly Phe Asn Leu Pro Ala Gly Pro Ala Ser Ile Thr Leu Thr
    50                  55                  60

Ser Asn Glu Thr Thr Ala Cys Val Ser Thr Gln Gly Asn Asn Thr Leu
65                  70                  75                  80

Phe Phe Ser Gly Gln Val Leu Val Asn Gly Ser Pro Thr Pro Gly Val
                85                  90                  95

Val Val Ser Phe Ser Phe Ser Asn Pro Ser Leu Ala Phe Met Val Pro
            100                 105                 110

Leu Ala Val Ile Thr Asn Ala Ser Gly Asn Phe Thr Ala Val Phe Leu
        115                 120                 125

Ala Ala Asn Gly Pro Gly Thr Val Thr Val Thr Ala Ser Leu Leu Asp
    130                 135                 140

Ser Pro Gly Thr Met Ala Ser Val Thr Ile Thr Ile Val Asn Cys Pro
145                 150                 155                 160


<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly
            20                  25                  30


<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35                  40                  45

Asn Thr Gly Leu Thr Gly Asn Thr Gly Pro Thr Gly Ile Thr Gly Pro
    50                  55                  60
```

```
Thr Gly Asp Thr Gly
65


<210> SEQ ID NO 27
<211> LENGTH: 36
<212> TYPE: PRT
<213> ORGANISM: Bacillus weihenstephensis

<400> SEQUENCE: 27

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35


<210> SEQ ID NO 28
<211> LENGTH: 934
<212> TYPE: PRT
<213> ORGANISM: Bacillus weihenstephensis

<400> SEQUENCE: 28

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Ala Gly Gln Met
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Val Pro Gly Ala Thr Gly Ser
145                 150                 155                 160

Gln Gly Ile Gln Gly Ala Gln Gly Ile Gln Gly Pro Gln Gly Pro Ser
                165                 170                 175

Gly Asn Thr Gly Ala Thr Gly Val Thr Gly Gln Gly Ile Ser Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Ala Thr Gly Ala Thr Gly Pro Gly Gly Gly Pro
    210                 215                 220

Ser Gly Ser Thr Gly Ala Thr Gly Ala Thr Gly Asn Thr Gly Val Thr
225                 230                 235                 240

Gly Ser Ala Gly Val Thr Gly Asn Thr Gly Ser Thr Gly Ser Thr Gly
                245                 250                 255

Glu Thr Gly Ala Gln Gly Leu Gln Gly Ile Gln Gly Val Gln Gly Pro
            260                 265                 270
```

-continued

```
Ile Gly Pro Thr Gly Pro Glu Gly Pro Gln Gly Ile Gln Gly Ile Pro
        275                 280                 285

Gly Pro Thr Gly Val Thr Gly Glu Gln Gly Ile Gln Gly Val Gln Gly
    290                 295                 300

Ile Gln Gly Ile Thr Gly Ala Thr Gly Asp Gln Gly Pro Gln Gly Ile
305                 310                 315                 320

Gln Gly Ala Ile Gly Pro Gln Gly Ile Thr Gly Ala Thr Gly Asp Gln
                325                 330                 335

Gly Pro Gln Gly Ile Gln Gly Val Pro Gly Pro Thr Gly Asp Thr Gly
            340                 345                 350

Ser Gln Gly Val Gln Gly Ile Gln Gly Pro Met Gly Asp Ile Gly Pro
        355                 360                 365

Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly
        435                 440                 445

Ala Thr Gly Pro Glu Gly Pro Gln Gly Val Gln Gly Thr Gln Gly Asp
    450                 455                 460

Ile Gly Pro Thr Gly Pro Met Gly Pro Gln Gly Val Gln Gly Ile Gln
465                 470                 475                 480

Gly Ile Gln Gly Pro Thr Gly Ala Gln Gly Val Gln Gly Pro Gln Gly
                485                 490                 495

Ile Gln Gly Ile Gln Gly Pro Thr Gly Val Thr Gly Asp Thr Gly Thr
            500                 505                 510

Thr Gly Ala Thr Gly Glu Gly Thr Thr Gly Ala Thr Gly Val Thr Gly
        515                 520                 525

Pro Ser Gly Val Thr Gly Pro Ser Gly Gly Pro Ala Gly Pro Thr Gly
    530                 535                 540

Pro Thr Gly Pro Ser Gly Pro Thr Gly Leu Thr Gly Pro Ser Gly Gly
545                 550                 555                 560

Pro Pro Gly Pro Thr Gly Ala Thr Gly Val Thr Gly Gly Val Gly Asp
                565                 570                 575

Thr Gly Ala Thr Gly Ser Thr Gly Val Thr Gly Ala Thr Gly Val Thr
            580                 585                 590

Gly Ala Thr Gly Ala Thr Gly Leu Gln Gly Pro Gln Gly Ile Gln Gly
        595                 600                 605

Val Gln Gly Asp Ile Gly Pro Thr Gly Pro Gln Gly Val Gln Gly Pro
    610                 615                 620

Gln Gly Ile Gln Gly Ile Thr Gly Ala Thr Gly Asp Gln Gly Pro Gln
625                 630                 635                 640

Gly Ile Gln Gly Pro Gln Gly Ile Gln Gly Pro Thr Gly Pro Gln Gly
                645                 650                 655

Ile Gln Gly Gly Gln Gly Pro Gln Gly Ile Gln Gly Ala Thr Gly Ala
            660                 665                 670

Thr Gly Ala Gln Gly Pro Gln Gly Ile Gln Gly Ile Gln Gly Val Gln
        675                 680                 685

Gly Pro Thr Gly Pro Gln Gly Pro Thr Gly Ile Gln Gly Val Gln Gly
```

```
    690                 695                 700

Glu Ile Gly Pro Thr Gly Pro Gln Gly Val Gln Gly Leu Gln Gly Pro
705                 710                 715                 720

Gln Gly Pro Thr Gly Asp Thr Gly Pro Thr Gly Pro Gln Gly Pro Gln
                725                 730                 735

Gly Ile Gln Gly Pro Thr Gly Ala Thr Gly Ala Thr Gly Ser Gln Gly
            740                 745                 750

Ile Gln Gly Pro Thr Gly Ala Thr Gly Ala Thr Gly Ser Gln Gly Ile
        755                 760                 765

Gln Gly Pro Thr Gly Ala Thr Gly Ala Thr Gly Ala Thr Gly Ala Thr
    770                 775                 780

Gly Ala Thr Gly Ala Thr Gly Ala Thr Gly Val Thr Gly Val Ser Thr
785                 790                 795                 800

Thr Ala Thr Tyr Ser Phe Ala Asn Asn Thr Ser Gly Ser Ala Ile Ser
                805                 810                 815

Val Leu Leu Gly Gly Thr Asn Ile Pro Leu Pro Asn Asn Gln Asn Ile
            820                 825                 830

Gly Pro Gly Ile Thr Val Ser Gly Gly Asn Thr Val Phe Thr Val Thr
        835                 840                 845

Asn Ala Gly Asn Tyr Tyr Ile Ala Tyr Thr Ile Asn Ile Thr Ala Ala
    850                 855                 860

Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
                885                 890                 895

Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
    930
```

<210> SEQ ID NO 29
<211> LENGTH: 39
<212> TYPE: PRT
<213> ORGANISM: Bacillus mycoides

<400> SEQUENCE: 29

```
Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35
```

<210> SEQ ID NO 30
<211> LENGTH: 287
<212> TYPE: PRT
<213> ORGANISM: Bacillus mycoides

<400> SEQUENCE: 30

```
Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Gly Thr Gly Pro Thr Gly
```

```
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Gly Thr Glu Gly Cys Leu Cys Asp
        115                 120                 125

Cys Cys Val Leu Pro Met Gln Ser Val Leu Gln Gln Leu Ile Gly Glu
    130                 135                 140

Thr Val Ile Leu Gly Thr Ile Ala Asp Thr Pro Asn Thr Pro Pro Leu
145                 150                 155                 160

Phe Phe Leu Phe Thr Ile Thr Ser Val Asn Asp Phe Leu Val Thr Val
                165                 170                 175

Thr Asp Gly Thr Thr Thr Phe Val Val Asn Ile Ser Asp Val Thr Gly
            180                 185                 190

Val Gly Phe Leu Pro Pro Gly Pro Pro Ile Thr Leu Leu Pro Pro Thr
        195                 200                 205

Asp Val Gly Cys Glu Cys Glu Cys Arg Glu Arg Pro Ile Arg Gln Leu
    210                 215                 220

Leu Asp Ala Phe Ile Gly Ser Thr Val Ser Leu Leu Ala Ser Asn Gly
225                 230                 235                 240

Ser Ile Ala Ala Asp Phe Ser Val Glu Gln Thr Gly Leu Gly Ile Val
                245                 250                 255

Leu Gly Thr Leu Pro Ile Asn Pro Thr Thr Thr Val Arg Phe Ala Ile
            260                 265                 270

Ser Thr Cys Lys Ile Thr Ala Val Asn Ile Thr Pro Ile Thr Met
        275                 280                 285


<210> SEQ ID NO 31
<211> LENGTH: 30
<212> TYPE: PRT
<213> ORGANISM: Bacillus mycoides

<400> SEQUENCE: 31

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly
            20                  25                  30


<210> SEQ ID NO 32
<211> LENGTH: 190
<212> TYPE: PRT
<213> ORGANISM: Bacillus mycoides

<400> SEQUENCE: 32

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly Pro Thr
            20                  25                  30

Gly Ser Thr Gly Ala Thr Gly Ser Thr Gly Ser Thr Gly Ser Thr Gly
        35                  40                  45

Pro Thr Gly Ser Thr Gly Ser Thr Gly Ser Thr Gly Ser Thr Gly Pro
```

```
    50                  55                  60

Thr Gly Pro Thr Gly Pro Thr Gly Ser Thr Gly Pro Thr Gly Pro Thr
65                  70                  75                  80

Gly Phe Asn Leu Pro Ala Gly Pro Ala Ser Ile Thr Leu Thr Ser Asn
                85                  90                  95

Glu Thr Thr Ala Cys Val Ser Thr Gln Gly Asn Asn Thr Leu Phe Phe
            100                 105                 110

Ser Gly Gln Val Leu Val Asn Gly Ser Pro Thr Pro Gly Val Val Val
        115                 120                 125

Ser Phe Ser Phe Ser Asn Pro Ser Leu Ala Phe Met Val Pro Leu Ala
    130                 135                 140

Val Ile Thr Asn Ala Ser Gly Asn Phe Thr Ala Val Phe Leu Ala Ala
145                 150                 155                 160

Asn Gly Pro Gly Thr Val Thr Val Thr Ala Ser Leu Leu Asp Ser Pro
                165                 170                 175

Gly Thr Met Ala Ser Val Thr Ile Thr Ile Val Asn Cys Pro
            180                 185                 190


<210> SEQ ID NO 33
<211> LENGTH: 21
<212> TYPE: PRT
<213> ORGANISM: Bacillus mycoides

<400> SEQUENCE: 33

Met Asp Ser Lys Asn Ile Gly Pro Thr Phe Pro Pro Leu Pro Ser Ile
1               5                   10                  15

Asn Phe Pro Thr Gly
            20


<210> SEQ ID NO 34
<211> LENGTH: 335
<212> TYPE: PRT
<213> ORGANISM: Bacillus mycoides

<400> SEQUENCE: 34

Met Asp Ser Lys Asn Ile Gly Pro Thr Phe Pro Pro Leu Pro Ser Ile
1               5                   10                  15

Asn Phe Pro Thr Gly Val Thr Gly Glu Thr Gly Ala Thr Gly Glu Thr
            20                  25                  30

Gly Ala Thr Gly Ala Thr Gly Glu Thr Gly Ala Thr Gly Glu Thr Gly
        35                  40                  45

Glu Thr Gly Ala Thr Gly Ala Thr Gly Ala Thr Gly Ala Thr Gly Glu
    50                  55                  60

Thr Gly Ala Thr Gly Ala Thr Gly Ala Thr Gly Ala Ala Gly Ala Thr
65                  70                  75                  80

Gly Glu Thr Gly Ala Thr Gly Glu Thr Gly Ala Thr Gly Glu Thr Gly
                85                  90                  95

Ala Thr Gly Glu Thr Gly Ala Thr Gly Val Thr Gly Glu Thr Gly Ala
            100                 105                 110

Thr Gly Glu Thr Gly Ala Ala Gly Glu Thr Gly Ile Thr Gly Val Thr
        115                 120                 125

Gly Pro Thr Gly Glu Thr Gly Ala Thr Gly Glu Thr Gly Ala Thr Gly
    130                 135                 140

Ala Thr Gly Ile Thr Gly Ala Thr Gly Ile Thr Gly Val Ala Gly Ala
145                 150                 155                 160

Thr Gly Glu Thr Gly Ala Ala Gly Glu Thr Gly Pro Thr Gly Ala Thr
```

```
                165                 170                 175

Gly Ala Ile Gly Ala Ile Gly Ala Thr Gly Ala Thr Gly Ile Thr Gly
            180                 185                 190

Val Thr Gly Ala Thr Gly Glu Thr Gly Ala Ala Gly Ala Thr Gly Ile
        195                 200                 205

Thr Gly Val Thr Gly Ala Thr Gly Glu Thr Gly Ala Ala Gly Ala Thr
    210                 215                 220

Gly Ile Thr Gly Ala Thr Gly Ile Thr Gly Val Ala Gly Ala Thr Gly
225                 230                 235                 240

Ile Thr Gly Pro Thr Gly Ile Pro Gly Thr Ile Pro Thr Thr Asn Leu
                245                 250                 255

Leu Tyr Phe Thr Phe Ser Asp Gly Glu Lys Leu Ile Tyr Thr Asn Ala
            260                 265                 270

Asp Gly Ile Ala Gln Tyr Gly Thr Thr Gln Ile Leu Ser Pro Ser Glu
        275                 280                 285

Val Ser Tyr Ile Asn Leu Phe Ile Asn Gly Ile Leu Gln Pro Gln Pro
    290                 295                 300

Phe Tyr Glu Val Thr Ala Gly Gln Leu Thr Leu Leu Asp Asp Glu Pro
305                 310                 315                 320

Pro Ser Gln Gly Ser Ser Ile Ile Leu Gln Phe Ile Ile Ile Asn
                325                 330                 335


<210> SEQ ID NO 35
<211> LENGTH: 22
<212> TYPE: PRT
<213> ORGANISM: Bacillus thuringiensis

<400> SEQUENCE: 35

Met Ile Gly Pro Glu Asn Ile Gly Pro Thr Phe Pro Ile Leu Pro Pro
1               5                   10                  15

Ile Tyr Ile Pro Thr Gly
            20


<210> SEQ ID NO 36
<211> LENGTH: 234
<212> TYPE: PRT
<213> ORGANISM: Bacillus thuringiensis

<400> SEQUENCE: 36

Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
```

-continued

```
    130                 135                 140

Gly Gly Ile Gly Pro Ile Thr Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
225                 230


<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37

ggatccatgg ctgaacacaa tcc                                              23


<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38

ggatccttaa ttcgtattct ggcc                                             24


<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39

ggatccatga aacggtcaat c                                                21


<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40

ggatccttac taatttggtt ctgt                                             24


<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41

ggatccatgc taccaaaagc c                                                21
```

<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42
ggatccttag tccgcaggcg tagc 24

<210> SEQ ID NO 43
<211> LENGTH: 35
<212> TYPE: PRT
<213> ORGANISM: Bacillus cereus

<400> SEQUENCE: 43

```
Met Ser Asn Asn Asn Ile Pro Ser Pro Phe Phe Phe Asn Asn Phe Asn
1               5                   10                  15

Pro Glu Leu Ile Gly Pro Thr Phe Pro Pro Ile Pro Pro Leu Thr Leu
            20                  25                  30

Pro Thr Gly
        35
```

<210> SEQ ID NO 44
<211> LENGTH: 222
<212> TYPE: PRT
<213> ORGANISM: Bacillus cereus

<400> SEQUENCE: 44

```
Met Ser Asn Asn Asn Ile Pro Ser Pro Phe Phe Phe Asn Asn Phe Asn
1               5                   10                  15

Pro Glu Leu Ile Gly Pro Thr Phe Pro Pro Ile Pro Pro Leu Thr Leu
            20                  25                  30

Pro Thr Gly Pro Thr Gly Ser Thr Gly Ala Thr Gly Ala Thr Gly Pro
        35                  40                  45

Thr Gly Ala Thr Gly Pro Thr Gly Ala Thr Gly Pro Thr Gly Ala Thr
    50                  55                  60

Gly Ala Thr Gly Ser Thr Gly Ala Thr Gly Pro Thr Gly Ala Thr Gly
65                  70                  75                  80

Thr Phe Ser Ser Ala Asn Ala Ser Ile Val Thr Pro Ala Pro Gln Thr
                85                  90                  95

Val Asn Asn Leu Ala Pro Ile Gln Phe Thr Ala Pro Val Leu Ile Ser
            100                 105                 110

Lys Asn Val Thr Phe Asn Gly Ile Asp Thr Phe Thr Ile Gln Ile Pro
        115                 120                 125

Gly Asn Tyr Phe Phe Ile Gly Ala Val Met Thr Ser Asn Asn Gln Ala
    130                 135                 140

Gly Pro Val Ala Val Gly Val Gly Phe Asn Gly Ile Pro Val Pro Ser
145                 150                 155                 160

Leu Asp Gly Ala Asn Tyr Gly Thr Pro Thr Gly Gln Glu Val Val Cys
                165                 170                 175

Phe Gly Phe Ser Gly Gln Ile Pro Ala Gly Thr Thr Ile Asn Leu Tyr
            180                 185                 190

Asn Ile Ser Asp Lys Thr Ile Ser Ile Gly Gly Ala Thr Ala Ala Gly
        195                 200                 205

Ser Ser Ile Val Ala Ala Arg Leu Ser Phe Phe Arg Ile Ser
    210                 215                 220
```

<210> SEQ ID NO 45
<211> LENGTH: 41
<212> TYPE: PRT
<213> ORGANISM: Bacillus cereus

<400> SEQUENCE: 45

```
Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
            20                  25                  30

Ile Pro Ser Phe Thr Leu Pro Thr Gly
        35                  40
```

<210> SEQ ID NO 46
<211> LENGTH: 293
<212> TYPE: PRT
<213> ORGANISM: Bacillus cereus

<400> SEQUENCE: 46

```
Met Phe Ser Glu Lys Lys Arg Lys Asp Leu Ile Pro Asp Asn Phe Leu
1               5                   10                  15

Ser Ala Pro Ala Leu Asp Pro Asn Leu Ile Gly Pro Thr Phe Pro Pro
            20                  25                  30

Ile Pro Ser Phe Thr Leu Pro Thr Gly Ser Thr Gly Pro Thr Gly Pro
        35                  40                  45

Thr Gly Asp Thr Gly Pro Thr Gly Pro Thr Ala Thr Ile Cys Ile Arg
    50                  55                  60

Thr Asp Pro Asp Asn Gly Cys Ser Val Ala Glu Gly Ser Gly Thr Val
65                  70                  75                  80

Ala Ser Gly Phe Ala Ser His Ala Glu Ala Cys Asn Thr Gln Ala Ile
                85                  90                  95

Gly Asp Cys Ser His Ala Glu Gly Gln Phe Ala Thr Ala Ser Gly Thr
            100                 105                 110

Ala Ser His Ala Glu Gly Phe Gln Thr Thr Ala Ser Gly Phe Ala Ser
        115                 120                 125

His Thr Glu Gly Ser Gly Thr Thr Ala Asp Ala Asn Phe Ser His Thr
    130                 135                 140

Glu Gly Ile Asn Thr Ile Val Asp Val Leu His Pro Gly Ser His Ile
145                 150                 155                 160

Met Gly Lys Asn Gly Thr Thr Arg Ser Ser Phe Ser Trp His Leu Ala
                165                 170                 175

Asn Gly Leu Ala Val Gly Pro Ser Leu Asn Ser Ala Val Ile Glu Gly
            180                 185                 190

Val Thr Gly Asn Leu Tyr Leu Asp Gly Val Val Ile Ser Pro Asn Ala
        195                 200                 205

Ala Asp Tyr Ala Glu Met Phe Glu Thr Ile Asp Gly Asn Leu Ile Asp
    210                 215                 220

Val Gly Tyr Phe Val Thr Leu Tyr Gly Glu Lys Ile Arg Lys Ala Asn
225                 230                 235                 240

Ala Asn Asp Asp Tyr Ile Leu Gly Val Val Ser Ala Thr Pro Ala Met
                245                 250                 255

Ile Ala Asp Ala Ser Asp Leu Arg Trp His Asn Leu Phe Val Arg Asp
            260                 265                 270

Glu Trp Gly Arg Thr Gln Tyr His Glu Val Val Val Pro Glu Lys Lys
        275                 280                 285
```

Met Ala Met Glu Glu
290

<210> SEQ ID NO 47
<211> LENGTH: 49
<212> TYPE: PRT
<213> ORGANISM: Bacillus cereus

<400> SEQUENCE: 47

Met Thr Arg Lys Asp Lys Phe Asn Arg Ser Arg Ile Ser Arg Arg Asp
1 5 10 15

Arg Phe Asn Ser Pro Lys Ile Lys Ser Glu Ile Leu Ile Ser Pro Asp
20 25 30

Leu Val Gly Pro Thr Phe Pro Pro Ile Pro Ser Phe Thr Leu Pro Thr
35 40 45

Gly

<210> SEQ ID NO 48
<211> LENGTH: 83
<212> TYPE: PRT
<213> ORGANISM: Bacillus cereus

<400> SEQUENCE: 48

Met Thr Arg Lys Asp Lys Phe Asn Arg Ser Arg Ile Ser Arg Arg Asp
1 5 10 15

Arg Phe Asn Ser Pro Lys Ile Lys Ser Glu Ile Leu Ile Ser Pro Asp
20 25 30

Leu Val Gly Pro Thr Phe Pro Pro Ile Pro Ser Phe Thr Leu Pro Thr
35 40 45

Gly Val Thr Gly Pro Thr Gly Asn Thr Gly Pro Thr Gly Ile Thr Gly
50 55 60

Pro Thr Gly Asp Thr Gly Pro Thr Gly Asp Thr Gly Pro Thr Gly Ile
65 70 75 80

Thr Gly Pro

<210> SEQ ID NO 49
<211> LENGTH: 38
<212> TYPE: PRT
<213> ORGANISM: Bacillus cereus

<400> SEQUENCE: 49

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly
35

<210> SEQ ID NO 50
<211> LENGTH: 163
<212> TYPE: PRT
<213> ORGANISM: Bacillus cereus

<400> SEQUENCE: 50

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly Ile Thr Gly Pro Thr Gly Asn Thr Gly Pro
35 40 45

Thr Gly Asp Thr Gly Pro Thr Gly Pro Thr Phe Asn Ile Asn Phe Arg
50 55 60

Ala Glu Lys Asn Gly Ala Gln Ser Phe Thr Pro Pro Ala Asp Ile Gln
65 70 75 80

Val Ser Tyr Gly Asn Ile Ile Phe Asn Asn Gly Gly Gly Tyr Ser Ser
85 90 95

Val Thr Asn Thr Phe Thr Ala Pro Ile Asn Gly Ile Tyr Leu Phe Ser
100 105 110

Ala Asn Ile Gly Phe Asn Pro Thr Leu Gly Thr Thr Ser Thr Leu Arg
115 120 125

Ile Thr Ile Arg Lys Asn Leu Val Ser Val Ala Ser Gln Thr Ile Asp
130 135 140

Ile Gln Phe Ser Ala Ala Glu Ser Gly Thr Leu Thr Val Gly Ser Ser
145 150 155 160

Asn Phe Phe

<210> SEQ ID NO 51
<211> LENGTH: 39
<212> TYPE: PRT
<213> ORGANISM: Bacillus cereus

<400> SEQUENCE: 51

Met Lys Glu Arg Asp Asn Lys Gly Lys Gln His Ser Leu Asn Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly
35

<210> SEQ ID NO 52
<211> LENGTH: 323
<212> TYPE: PRT
<213> ORGANISM: Bacillus cereus

<400> SEQUENCE: 52

Met Lys Glu Arg Asp Asn Lys Gly Lys Gln His Ser Leu Asn Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly Ile Thr Gly Pro Thr Gly Pro Gln Gly
35 40 45

Pro Thr Gly Pro Gln Gly Pro Arg Gly Phe Gln Gly Pro Met Gly Glu
50 55 60

Met Gly Pro Thr Gly Pro Gln Gly Val Gln Gly Ile Gln Gly Pro Ala
65 70 75 80

Gly Gln Met Gly Ala Thr Gly Pro Glu Gly Gln Gln Gly Pro Glu Gly
85 90 95

Leu Arg Gly Pro Val Gly Ala Thr Gly Ala Thr Gly Leu Gln Gly Val
100 105 110

Gln Gly Ile Gln Gly Pro Ile Gly Ser Thr Gly Ala Thr Gly Ala Gln
115 120 125

Gly Ile Gln Gly Ile Gln Gly Leu Gln Gly Pro Ile Gly Ala Thr Gly
130 135 140

Pro Glu Gly Pro Gln Gly Ile Gln Gly Val Gln Gly Leu Pro Gly Ala 145 150 155 160

Thr Gly Pro Gln Gly Val Gln Gly Val Gln Gly Val Ile Gly Pro Gln
165 170 175

Gly Pro Ser Gly Ser Thr Gly Gly Thr Gly Ala Thr Gly Gln Gly Val
180 185 190

Thr Gly Pro Thr Gly Ile Thr Gly Ser Thr Gly Val Thr Gly Pro Ser
195 200 205

Gly Gly Pro Pro Gly Pro Thr Gly Pro Thr Gly Ala Thr Gly Pro Gly
210 215 220

Gly Gly Pro Ser Gly Ser Thr Gly Val Thr Gly Ser Thr Gly Asn Thr
225 230 235 240

Gly Ala Thr Gly Ser Pro Gly Val Thr Gly Ala Thr Gly Pro Thr Gly
245 250 255

Ser Thr Gly Ala Thr Gly Ile Gln Gly Ser Gln Gly Ile Gln Gly Ile
260 265 270

Gln Gly Ile Gln Gly Pro Leu Gly Pro Thr Gly Pro Glu Gly Pro Gln
275 280 285

Gly Ile Gln Gly Ile Pro Gly Pro Thr Gly Ile Thr Gly Glu Gln Gly
290 295 300

Ile Gln Gly Val Gln Gly Ile Gln Gly Ile Thr Gly Ala Thr Gly Asp
305 310 315 320

Gln Gly Thr

<210> SEQ ID NO 53
<211> LENGTH: 39
<212> TYPE: PRT
<213> ORGANISM: Bacillus cereus

<400> SEQUENCE: 53

Met Arg Glu Arg Asp Asn Lys Arg Gln Gln His Ser Leu Asn Pro Asn
1 5 10 15

Phe Arg Ile Ser Pro Glu Leu Ile Gly Pro Thr Phe Pro Pro Val Pro
20 25 30

Thr Gly Phe Thr Gly Ile Gly
35

<210> SEQ ID NO 54
<211> LENGTH: 436
<212> TYPE: PRT
<213> ORGANISM: Bacillus cereus

<400> SEQUENCE: 54

Met Arg Glu Arg Asp Asn Lys Arg Gln Gln His Ser Leu Asn Pro Asn
1 5 10 15

Phe Arg Ile Ser Pro Glu Leu Ile Gly Pro Thr Phe Pro Pro Val Pro
20 25 30

Thr Gly Phe Thr Gly Ile Gly Ile Thr Gly Pro Thr Gly Pro Gln Gly
35 40 45

Pro Thr Gly Pro Gln Gly Pro Arg Gly Phe Gln Gly Pro Met Gly Glu
50 55 60

Met Gly Pro Thr Gly Pro Gln Gly Val Gln Gly Ile Gln Gly Pro Val
65 70 75 80

Gly Pro Ile Gly Ala Thr Gly Pro Glu Gly Gln Gln Gly Pro Gln Gly
85 90 95

Leu Arg Gly Pro Gln Gly Glu Thr Gly Ala Thr Gly Pro Gly Gly Val
100 105 110

Gln Gly Leu Gln Gly Pro Ile Gly Pro Thr Gly Ala Thr Gly Ala Gln
115 120 125

Gly Val Gln Gly Ile Gln Gly Leu Gln Gly Pro Ile Gly Ala Thr Gly
130 135 140

Pro Glu Gly Pro Gln Gly Ile Gln Gly Val Gln Gly Leu Pro Gly Ala
145 150 155 160

Thr Gly Ser Gln Gly Ile Gln Gly Val Gln Gly Ile Gln Gly Pro Gln
165 170 175

Gly Pro Ser Gly Asn Thr Gly Ala Thr Gly Ala Thr Gly Gln Gly Ile
180 185 190

Thr Gly Pro Thr Gly Ile Thr Gly Pro Thr Gly Ile Thr Gly Pro Ser
195 200 205

Gly Gly Pro Pro Gly Pro Thr Gly Pro Thr Gly Ala Thr Gly Pro Gly
210 215 220

Gly Gly Pro Ser Gly Ser Thr Gly Ala Thr Gly Ala Thr Gly Asn Thr
225 230 235 240

Gly Ala Thr Gly Asn Thr Gly Ile Thr Gly Ala Thr Gly Ser Thr Gly
245 250 255

Pro Thr Gly Ser Thr Gly Ala Gln Gly Leu Gln Gly Ile Gln Gly Ile
260 265 270

Gln Gly Pro Ile Gly Pro Thr Gly Pro Glu Gly Pro Gln Gly Ile Gln
275 280 285

Gly Ile Pro Gly Pro Thr Gly Val Thr Gly Glu Gln Gly Ile Gln Gly
290 295 300

Val Gln Gly Ile Gln Gly Ile Thr Gly Ala Thr Gly Asp Gln Gly Pro
305 310 315 320

Gln Gly Ile Gln Gly Val Ile Gly Ala Gln Gly Val Thr Gly Ala Thr
325 330 335

Gly Asp Gln Gly Pro Gln Gly Ile Gln Gly Val Pro Gly Pro Ser Gly
340 345 350

Ala Thr Gly Pro Gln Gly Val Gln Gly Ile Gln Gly Pro Met Gly Asp
355 360 365

Ile Gly Pro Thr Gly Pro Glu Gly Pro Glu Gly Leu Gln Gly Pro Gln
370 375 380

Gly Ile Gln Gly Val Pro Gly Pro Val Gly Ala Thr Gly Pro Glu Gly
385 390 395 400

Pro Gln Gly Ile Gln Gly Ile Gln Gly Val Gln Gly Ala Thr Gly Pro
405 410 415

Gln Gly Pro Gln Gly Ile Gln Gly Ile Gln Gly Val Gln Gly Ile Thr
420 425 430

Gly Ala Thr Gly
435

<210> SEQ ID NO 55
<211> LENGTH: 36
<212> TYPE: PRT
<213> ORGANISM: Bacillus thuringiensis

<400> SEQUENCE: 55

Met Lys Asn Arg Asp Asn Lys Gly Lys Gln Gln Ser Asn Phe Arg Ile
1 5 10 15

Pro Pro Glu Leu Ile Gly Pro Thr Phe Pro Pro Val Pro Thr Gly Phe
20 25 30

Thr Gly Ile Gly

35

<210> SEQ ID NO 56
<211> LENGTH: 470
<212> TYPE: PRT
<213> ORGANISM: Bacillus thuringiensis

<400> SEQUENCE: 56

Met Lys Asn Arg Asp Asn Lys Gly Lys Gln Gln Ser Asn Phe Arg Ile
1 5 10 15

Pro Pro Glu Leu Ile Gly Pro Thr Phe Pro Pro Val Pro Thr Gly Phe
20 25 30

Thr Gly Ile Gly Ile Thr Gly Pro Thr Gly Pro Gln Gly Pro Thr Gly
35 40 45

Pro Gln Gly Pro Arg Gly Phe Gln Gly Pro Met Gly Glu Met Gly Pro
50 55 60

Thr Gly Pro Gln Gly Val Gln Gly Ile Gln Gly Pro Val Gly Pro Ile
65 70 75 80

Gly Ala Thr Gly Pro Glu Gly Gln Gln Gly Ala Gln Gly Leu Arg Gly
85 90 95

Pro Gln Gly Glu Thr Gly Ala Thr Gly Pro Gln Gly Val Gln Gly Leu
100 105 110

Gln Gly Pro Ile Gly Pro Thr Gly Ala Thr Gly Ala Gln Gly Ile Gln
115 120 125

Gly Ile Gln Gly Leu Gln Gly Pro Ile Gly Ala Thr Gly Pro Glu Gly
130 135 140

Pro Gln Gly Ile Gln Gly Val Gln Gly Leu Pro Gly Ala Thr Gly Pro
145 150 155 160

Gln Gly Ile Gln Gly Ala Gln Gly Ile Gln Gly Thr Gln Gly Pro Ser
165 170 175

Gly Asn Thr Gly Ala Thr Gly Ala Thr Gly Gln Gly Leu Thr Gly Pro
180 185 190

Thr Gly Ile Thr Gly Pro Thr Gly Ile Thr Gly Pro Ser Gly Gly Pro
195 200 205

Pro Gly Pro Thr Gly Pro Thr Gly Ala Thr Gly Pro Gly Gly Gly Pro
210 215 220

Ser Gly Ser Thr Gly Ala Thr Gly Ala Thr Gly Asp Thr Gly Ala Thr
225 230 235 240

Gly Ser Thr Gly Val Thr Gly Ala Thr Gly Ala Gln Gly Pro Gln Gly
245 250 255

Val Gln Gly Ile Gln Gly Pro Thr Gly Ala Thr Gly Ala Thr Gly Ala
260 265 270

Thr Gly Pro Gln Gly Ile Gln Gly Pro Gln Gly Ile Gln Gly Pro Thr
275 280 285

Gly Ala Thr Gly Ala Thr Gly Ser Gln Gly Pro Thr Gly Asn Thr Gly
290 295 300

Pro Thr Gly Ser Gln Gly Ile Gln Gly Pro Thr Gly Pro Thr Gly Ala
305 310 315 320

Gly Ala Thr Gly Ala Thr Gly Ala Thr Gly Ala Thr Gly Val Ser Thr
325 330 335

Thr Ala Thr Tyr Ala Phe Ala Asn Asn Thr Ser Gly Ser Ile Ile Ser
340 345 350

Val Leu Leu Gly Gly Thr Asn Ile Pro Leu Pro Asn Asn Gln Asn Ile
355 360 365

```
Gly Pro Gly Ile Thr Val Ser Gly Gly Asn Thr Val Phe Thr Val Ala
    370                 375                 380

Asn Ala Gly Asn Tyr Tyr Ile Ala Tyr Thr Ile Asn Leu Thr Ala Gly
385                 390                 395                 400

Leu Leu Val Ser Ser Arg Ile Thr Val Asn Gly Ser Pro Leu Ala Gly
                405                 410                 415

Thr Ile Asn Ser Pro Ala Val Ala Ala Gly Ser Phe Ser Ala Thr Ile
            420                 425                 430

Ile Ala Asn Leu Pro Ala Gly Ala Ala Val Ser Leu Gln Leu Phe Gly
        435                 440                 445

Val Ile Ala Leu Ala Thr Leu Ser Thr Ala Thr Pro Gly Ala Thr Leu
    450                 455                 460

Thr Ile Ile Arg Leu Ser
465                 470


<210> SEQ ID NO 57
<211> LENGTH: 136
<212> TYPE: PRT
<213> ORGANISM: Bacillus mycoides

<400> SEQUENCE: 57

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly
    130                 135


<210> SEQ ID NO 58
<211> LENGTH: 384
<212> TYPE: PRT
<213> ORGANISM: Bacillus mycoides

<400> SEQUENCE: 58

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Cys Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80
```

-continued

```
Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly Pro Thr
    130                 135                 140

Gly Val Thr Gly Pro Thr Gly Val Thr Gly Pro Thr Gly Val Thr Gly
145                 150                 155                 160

Pro Thr Gly Val Thr Gly Pro Thr Gly Val Thr Gly Pro Thr Gly Val
                165                 170                 175

Thr Gly Pro Thr Gly Val Thr Gly Pro Thr Gly Val Thr Gly Pro Thr
            180                 185                 190

Gly Val Thr Gly Pro Thr Gly Val Thr Gly Pro Thr Gly Val Thr Gly
        195                 200                 205

Pro Thr Gly Val Thr Gly Pro Thr Gly Gly Thr Glu Gly Cys Leu Cys
    210                 215                 220

Asp Cys Cys Val Leu Pro Met Gln Ser Val Leu Gln Gln Leu Ile Gly
225                 230                 235                 240

Glu Thr Val Ile Leu Gly Thr Ile Ala Asp Thr Pro Asn Thr Pro Pro
                245                 250                 255

Leu Phe Phe Leu Phe Thr Ile Thr Ser Val Asn Asp Phe Leu Val Thr
            260                 265                 270

Val Thr Asp Gly Thr Thr Thr Phe Val Val Asn Ile Ser Asp Val Thr
        275                 280                 285

Gly Val Gly Phe Leu Pro Pro Gly Pro Pro Ile Thr Leu Leu Pro Pro
    290                 295                 300

Thr Asp Val Gly Cys Glu Cys Glu Cys Arg Glu Arg Pro Ile Arg Gln
305                 310                 315                 320

Leu Leu Asp Ala Phe Ile Gly Ser Thr Val Ser Leu Leu Ala Ser Asn
                325                 330                 335

Gly Ser Ile Ala Ala Asp Phe Ser Val Glu Gln Thr Gly Leu Gly Ile
            340                 345                 350

Val Leu Gly Thr Leu Pro Ile Asn Pro Thr Thr Thr Val Arg Phe Ala
        355                 360                 365

Ile Ser Thr Cys Lys Ile Thr Ala Val Asn Ile Thr Pro Ile Thr Met
    370                 375                 380


<210> SEQ ID NO 59
<211> LENGTH: 196
<212> TYPE: PRT
<213> ORGANISM: Bacillus anthracis

<400> SEQUENCE: 59

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80
```

```
Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly
        195


<210> SEQ ID NO 60
<211> LENGTH: 17
<212> TYPE: PRT
<213> ORGANISM: Bacillus anthracis

<400> SEQUENCE: 60

Met Ala Phe Asp Pro Asn Leu Val Gly Pro Thr Leu Pro Pro Ile Pro
1               5                   10                  15

Pro


<210> SEQ ID NO 61
<211> LENGTH: 17
<212> TYPE: PRT
<213> ORGANISM: Bacillus anthracis

<400> SEQUENCE: 61

Met Ala Leu Glu Pro Asn Leu Ile Gly Pro Thr Leu Pro Pro Ile Pro
1               5                   10                  15

Pro


<210> SEQ ID NO 62
<211> LENGTH: 17
<212> TYPE: PRT
<213> ORGANISM: Bacillus weihenstephensis

<400> SEQUENCE: 62

Met Ala Leu Asn Pro Asn Leu Ile Gly Pro Thr Leu Pro Pro Ile Pro
1               5                   10                  15

Pro


<210> SEQ ID NO 63
<211> LENGTH: 17
<212> TYPE: PRT
<213> ORGANISM: Bacillus weihenstephensis

<400> SEQUENCE: 63

Met Ala Leu Asp Pro Asn Ile Ile Gly Pro Thr Leu Pro Pro Ile Pro
1               5                   10                  15

Pro


<210> SEQ ID NO 64
```

<211> LENGTH: 17
<212> TYPE: PRT
<213> ORGANISM: Bacillus cereus

<400> SEQUENCE: 64

Met Ala Leu Glu Pro Asn Leu Ile Gly Pro Thr Leu Pro Ser Ile Pro
1 5 10 15

Pro

<210> SEQ ID NO 65
<211> LENGTH: 17
<212> TYPE: PRT
<213> ORGANISM: Bacillus weihenstephensis

<400> SEQUENCE: 65

Met Ala Leu Asp Pro Asn Leu Ile Gly Pro Pro Leu Pro Pro Ile Thr
1 5 10 15

Pro

<210> SEQ ID NO 66
<211> LENGTH: 17
<212> TYPE: PRT
<213> ORGANISM: Bacillus weihenstephensis

<400> SEQUENCE: 66

Met Ala Leu Asn Pro Gly Ser Ile Gly Pro Thr Leu Pro Pro Val Pro
1 5 10 15

Pro

<210> SEQ ID NO 67
<211> LENGTH: 17
<212> TYPE: PRT
<213> ORGANISM: Bacillus weihenstephensis

<400> SEQUENCE: 67

Met Ala Leu Asn Pro Cys Ser Ile Gly Pro Thr Leu Pro Pro Met Gln
1 5 10 15

Pro

<210> SEQ ID NO 68
<211> LENGTH: 17
<212> TYPE: PRT
<213> ORGANISM: Bacillus mycoides

<400> SEQUENCE: 68

Met Ala Leu Asn Pro Gly Ser Ile Gly Pro Thr Leu Pro Pro Val Gln
1 5 10 15

Pro

<210> SEQ ID NO 69
<211> LENGTH: 17
<212> TYPE: PRT
<213> ORGANISM: Bacillus anthracis

<400> SEQUENCE: 69

Met Ala Leu Asn Pro Gly Ser Val Gly Pro Thr Leu Pro Pro Met Gln
1 5 10 15

Pro

<210> SEQ ID NO 70
<211> LENGTH: 17

<212> TYPE: PRT
<213> ORGANISM: Bacillus cereus

<400> SEQUENCE: 70

Met Ala Leu Asp Pro Asn Leu Ile Gly Pro Thr Phe Pro Pro Ile Pro
1               5                   10                  15

Ser

<210> SEQ ID NO 71
<211> LENGTH: 799
<212> TYPE: PRT
<213> ORGANISM: Bacillus mycoides

<400> SEQUENCE: 71

Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

Gly Thr Ile Asp Gln Ser Ala Ser Lys Glu Glu Thr Gln Lys Ala Val
65                  70                  75                  80

Glu Gln Tyr Ile Glu Lys Lys Lys Gly Asp Gln Pro Asn Lys Glu Ile
                85                  90                  95

Leu Pro Asp Asp Pro Ala Lys Glu Ala Ser Asp Phe Val Lys Lys Val
            100                 105                 110

Lys Glu Lys Lys Met Glu Glu Lys Glu Lys Val Lys Lys Ser Val Glu
        115                 120                 125

Asn Ala Ser Ser Glu Gln Thr Pro Ser Gln Asn Lys Lys Gln Leu Asn
    130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
            180                 185                 190

Phe Ser Arg Glu His Tyr Gln Lys Met Leu Phe Gly Asn Glu Pro Phe
        195                 200                 205

Thr Leu Phe Asp Gly Ser Lys Val Lys Thr Phe Lys Gln Tyr Tyr Glu
    210                 215                 220

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
                245                 250                 255

Gly His Asp Asn Lys Gly Pro Lys Gly Ala Arg Asp Leu Val Lys Glu
            260                 265                 270

Ala Leu Lys Ala Ala Ala Glu Lys Gly Leu Asp Leu Ser Gln Phe Asp
        275                 280                 285

Gln Phe Asp Arg Tyr Asp Thr Asn Gly Asp Gly Asn Gln Asn Glu Pro
    290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg

```
                325                 330                 335

Ser Lys Leu Ala Gln Asp Pro Val Ala Ile Glu Gly Thr Lys Ser Lys
            340                 345                 350

Val Ser Tyr Trp Asp Gly Lys Val Ala Ala His Asp Tyr Thr Ile Glu
        355                 360                 365

Pro Glu Asp Gly Ala Val Gly Val Phe Ala His Glu Phe Gly His Asp
    370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Gly Ser Trp Thr Gly Arg
                405                 410                 415

Ile Ala Gly Thr Glu Pro Thr Ser Phe Ser Pro Gln Asn Lys Asp Phe
            420                 425                 430

Leu Gln Lys Asn Met Asp Gly Asn Trp Ala Lys Ile Val Glu Val Asp
        435                 440                 445

Tyr Asp Lys Ile Lys Arg Gly Val Gly Phe Pro Thr Tyr Ile Asp Gln
    450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
                485                 490                 495

Tyr Ser Thr Arg Gly Asp Asp Met His Thr Thr Leu Glu Thr Pro Leu
            500                 505                 510

Phe Asp Leu Thr Lys Ala Ala Asn Ala Lys Phe Asp Tyr Lys Ala Asn
        515                 520                 525

Tyr Glu Leu Glu Ala Glu Cys Asp Phe Ile Glu Val His Ala Val Thr
    530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
                565                 570                 575

Asp Leu Ser Gln Phe Lys Gly Lys Lys Val Lys Leu Gln Phe Asp Tyr
            580                 585                 590

Ile Thr Asp Pro Ala Leu Thr Tyr Lys Gly Phe Ala Met Asp Asn Val
        595                 600                 605

Asn Val Thr Val Asp Gly Lys Val Val Phe Ser Asp Asp Ala Glu Gly
    610                 615                 620

Gln Ala Lys Met Lys Leu Asn Gly Phe Val Val Ser Asp Gly Thr Glu
625                 630                 635                 640

Lys Lys Pro His Tyr Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
        675                 680                 685

His Pro Gly Glu Gly Phe Leu Gly Val Val Asp Ser His Pro Glu Ala
    690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
                725                 730                 735

Val Asn Ser Phe Thr Arg Gly Gln Phe Asn Tyr Pro Gly Leu Pro Gly
            740                 745                 750
```

Val Ala Thr Phe Asp Asp Ser Lys Val Tyr Ser Asn Thr Gln Ile Pro
        755                 760                 765

Asp Ala Gly Arg Lys Val Pro Gln Leu Gly Leu Lys Phe Gln Val Val
    770                 775                 780

Gly Gln Ala Asp Asp Lys Ser Ala Gly Ala Ile Trp Ile Arg Arg
785                 790                 795

<210> SEQ ID NO 72
<211> LENGTH: 152
<212> TYPE: PRT
<213> ORGANISM: Bacillus anthracis

<400> SEQUENCE: 72

Met Ser Cys Asn Glu Asn Lys His His Gly Ser Ser His Cys Val Val
1               5                   10                  15

Asp Val Val Lys Phe Ile Asn Glu Leu Gln Asp Cys Ser Thr Thr Thr
            20                  25                  30

Cys Gly Ser Gly Cys Glu Ile Pro Phe Leu Gly Ala His Asn Thr Ala
        35                  40                  45

Ser Val Ala Asn Thr Arg Pro Phe Ile Leu Tyr Thr Lys Ala Gly Ala
    50                  55                  60

Pro Phe Glu Ala Phe Ala Pro Ser Ala Asn Leu Thr Ser Cys Arg Ser
65                  70                  75                  80

Pro Ile Phe Arg Val Glu Ser Val Asp Asp Asp Ser Cys Ala Val Leu
                85                  90                  95

Arg Val Leu Ser Val Val Leu Gly Asp Ser Ser Pro Val Pro Pro Thr
            100                 105                 110

Asp Asp Pro Ile Cys Thr Phe Leu Ala Val Pro Asn Ala Arg Leu Val
        115                 120                 125

Ser Thr Ser Thr Cys Ile Thr Val Asp Leu Ser Cys Phe Cys Ala Ile
    130                 135                 140

Gln Cys Leu Arg Asp Val Thr Ile
145                 150

<210> SEQ ID NO 73
<211> LENGTH: 167
<212> TYPE: PRT
<213> ORGANISM: Bacillus anthracis

<400> SEQUENCE: 73

Met Phe Ser Ser Asp Cys Glu Phe Thr Lys Ile Asp Cys Glu Ala Lys
1               5                   10                  15

Pro Ala Ser Thr Leu Pro Ala Phe Gly Phe Ala Phe Asn Ala Ser Ala
            20                  25                  30

Pro Gln Phe Ala Ser Leu Phe Thr Pro Leu Leu Leu Pro Ser Val Ser
        35                  40                  45

Pro Asn Pro Asn Ile Thr Val Pro Val Ile Asn Asp Thr Val Ser Val
    50                  55                  60

Gly Asp Gly Ile Arg Ile Leu Arg Ala Gly Ile Tyr Gln Ile Ser Tyr
65                  70                  75                  80

Thr Leu Thr Ile Ser Leu Asp Asn Ser Pro Val Ala Pro Glu Ala Gly
                85                  90                  95

Arg Phe Phe Leu Ser Leu Gly Thr Pro Ala Asn Ile Ile Pro Gly Ser
            100                 105                 110

Gly Thr Ala Val Arg Ser Asn Val Ile Gly Thr Gly Glu Val Asp Val
        115                 120                 125

```
Ser Ser Gly Val Ile Leu Ile Asn Leu Asn Pro Gly Asp Leu Ile Arg
    130                 135                 140

Ile Val Pro Val Glu Leu Ile Gly Thr Val Asp Ile Arg Ala Ala Ala
145                 150                 155                 160

Leu Thr Val Ala Gln Ile Ser
                165
```

<210> SEQ ID NO 74
<211> LENGTH: 156
<212> TYPE: PRT
<213> ORGANISM: Bacillus anthracis

<400> SEQUENCE: 74

```
Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155
```

<210> SEQ ID NO 75
<211> LENGTH: 182
<212> TYPE: PRT
<213> ORGANISM: Bacillus anthracis

<400> SEQUENCE: 75

```
Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125
```

```
Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
            180


<210> SEQ ID NO 76
<211> LENGTH: 174
<212> TYPE: PRT
<213> ORGANISM: Bacillus anthracis

<400> SEQUENCE: 76

Met Lys Glu Arg Ser Glu Asn Met Arg Ser Ser Ser Arg Lys Leu Thr
1               5                   10                  15

Asn Phe Asn Cys Arg Ala Gln Ala Pro Ser Thr Leu Pro Ala Leu Gly
            20                  25                  30

Phe Ala Phe Asn Ala Thr Ser Pro Gln Phe Ala Thr Leu Phe Thr Pro
        35                  40                  45

Leu Leu Leu Pro Ser Thr Gly Pro Asn Pro Asn Ile Thr Val Pro Val
    50                  55                  60

Ile Asn Asp Thr Ile Ser Thr Gly Thr Gly Ile Arg Ile Gln Val Ala
65                  70                  75                  80

Gly Ile Tyr Gln Ile Ser Tyr Thr Leu Thr Ile Ser Leu Asp Asn Val
                85                  90                  95

Pro Val Thr Pro Glu Ala Ala Arg Phe Phe Leu Thr Leu Asn Ser Ser
            100                 105                 110

Thr Asn Ile Ile Ala Gly Ser Gly Thr Ala Val Arg Ser Asn Ile Ile
        115                 120                 125

Gly Thr Gly Glu Val Asp Val Ser Ser Gly Val Ile Leu Ile Asn Leu
    130                 135                 140

Asn Pro Gly Asp Leu Ile Gln Ile Val Pro Val Glu Val Ile Gly Thr
145                 150                 155                 160

Val Asp Ile Arg Ser Ala Ala Leu Thr Val Ala Gln Ile Arg
                165                 170


<210> SEQ ID NO 77
<211> LENGTH: 796
<212> TYPE: PRT
<213> ORGANISM: Bacillus thuringiensis

<400> SEQUENCE: 77

Met Ser Lys Lys Pro Phe Lys Val Leu Ser Ser Ile Ala Leu Thr Ala
1               5                   10                  15

Val Leu Gly Leu Ser Phe Gly Ala Gly Thr Gln Ser Ala Tyr Ala Glu
            20                  25                  30

Thr Pro Val Asn Lys Thr Ala Thr Ser Pro Val Asp Asp His Leu Ile
        35                  40                  45

Pro Glu Glu Arg Leu Ala Asp Ala Leu Lys Lys Arg Gly Val Ile Asp
    50                  55                  60

Ser Lys Ala Ser Glu Thr Glu Thr Lys Lys Ala Val Glu Lys Tyr Val
65                  70                  75                  80

Glu Asn Lys Lys Gly Glu Asn Pro Gly Lys Glu Ala Ala Asn Gly Asp
                85                  90                  95
```

```
Gln Leu Thr Lys Asp Ala Ser Asp Phe Leu Lys Lys Val Lys Asp Ala
            100                 105                 110

Lys Ala Asp Thr Lys Glu Lys Leu Asn Gln Pro Ala Thr Gly Thr Pro
        115                 120                 125

Ala Ala Thr Gly Pro Val Lys Gly Gly Leu Asn Gly Lys Val Pro Thr
    130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly Gly His Asp Asn
                245                 250                 255

Lys Gly Pro Lys Gly Pro Arg Asp Leu Val Lys Asp Ala Leu Lys Ala
            260                 265                 270

Ala Val Asp Ser Gly Ile Asp Leu Ser Glu Phe Asp Gln Phe Asp Gln
        275                 280                 285

Tyr Asp Val Asn Gly Asp Gly Asn Lys Asn Gln Pro Asp Gly Leu Ile
    290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
                325                 330                 335

Pro Lys Pro Phe Pro Ile Glu Gly Thr Gln Ala Lys Val Pro Tyr Trp
            340                 345                 350

Gly Gly Lys Met Ala Ala Phe Asp Tyr Thr Ile Glu Pro Glu Asp Gly
        355                 360                 365

Ala Val Gly Val Phe Ala His Glu Tyr Gly His Asp Leu Gly Leu Pro
    370                 375                 380

Asp Glu Tyr Asp Thr Gln Tyr Ser Gly Gln Gly Glu Pro Ile Glu Ala
385                 390                 395                 400

Trp Ser Ile Met Ser Gly Gly Ser Trp Ala Gly Lys Ile Ala Gly Thr
                405                 410                 415

Thr Pro Thr Ser Phe Ser Pro Gln Asn Lys Glu Phe Phe Gln Lys Thr
            420                 425                 430

Ile Gly Gly Asn Trp Ala Asn Ile Val Glu Val Asp Tyr Glu Lys Leu
        435                 440                 445

Asn Lys Gly Ile Gly Leu Ala Thr Tyr Leu Asp Gln Ser Val Thr Lys
    450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Tyr Ser Thr Lys
                485                 490                 495

Gly Asp Asp Leu His Thr Lys Met Glu Thr Pro Leu Phe Asp Leu Thr
            500                 505                 510
```

```
Asn Ala Thr Ser Ala Lys Phe Asp Phe Lys Ser Leu Tyr Glu Ile Glu
        515                 520                 525

Ala Gly Tyr Asp Phe Leu Glu Val His Ala Val Thr Glu Asp Gly Lys
    530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
                565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
        595                 600                 605

Asp Gly Lys Val Val Phe Ser Asp Asp Ala Glu Gly Thr Pro Gln Leu
    610                 615                 620

Lys Leu Asp Gly Phe Val Val Ser Asn Gly Thr Glu Lys Lys Lys His
625                 630                 635                 640

Asn Tyr Tyr Val Glu Trp Arg Asn Tyr Ala Gly Ala Asp Asn Ala Leu
                645                 650                 655

Lys Phe Ala Arg Gly Pro Val Phe Asn Thr Gly Met Val Val Trp Tyr
            660                 665                 670

Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795
```

<210> SEQ ID NO 78
<211> LENGTH: 430
<212> TYPE: PRT
<213> ORGANISM: Bacillus cereus

<400> SEQUENCE: 78

```
Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95
```

```
Leu Leu Gln Ser Pro Ala Pro Asn Leu Gly Gln Leu Ser Thr Leu Leu
            100                 105                 110

Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175

Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220

Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255

Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430


<210> SEQ ID NO 79
<211> LENGTH: 437
<212> TYPE: PRT
<213> ORGANISM: Bacillus cereus

<400> SEQUENCE: 79

Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
```

```
        35                  40                  45

Ala Ile Ala Ala Phe Phe Ala Asn Pro Ser Asp Ala Asn Arg Leu Ala
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125

Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
        195                 200                 205

Val Ala Gly Pro Ala Gly Pro Thr Gly Pro Thr Gly Asp Thr Gly Leu
    210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
            260                 265                 270

Ala Gly Gly Gly Ala Ile Ile Pro Phe Ala Ser Gly Thr Thr Pro Ala
        275                 280                 285

Ala Leu Val Asn Ala Leu Ile Ala Asn Thr Gly Thr Leu Leu Gly Phe
    290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
                325                 330                 335

Val Ile Thr Ser Leu Ala Gly Phe Phe Ser Ala Thr Ala Ala Leu Ser
            340                 345                 350

Pro Leu Ser Pro Val Gln Val Gln Ile Gln Ile Leu Thr Ala Pro Ala
        355                 360                 365

Ala Ser Asn Thr Phe Thr Val Gln Gly Ala Pro Leu Leu Leu Thr Pro
    370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
            420                 425                 430

Gly Ile Asn Ile Val
        435
```

<210> SEQ ID NO 80

<211> LENGTH: 119
<212> TYPE: PRT
<213> ORGANISM: Bacillus anthracis

<400> SEQUENCE: 80

Met Leu Phe Thr Ser Trp Leu Leu Phe Phe Ile Phe Ala Leu Ala Ala
1 5 10 15

Phe Arg Leu Thr Arg Leu Ile Val Tyr Asp Lys Ile Thr Gly Phe Leu
20 25 30

Arg Arg Pro Phe Ile Asp Glu Leu Glu Ile Thr Glu Pro Asp Gly Ser
35 40 45

Val Ser Thr Phe Thr Lys Val Lys Gly Lys Gly Leu Arg Lys Trp Ile
50 55 60

Gly Glu Leu Leu Ser Cys Tyr Trp Cys Thr Gly Val Trp Val Ser Ala
65 70 75 80

Phe Leu Leu Val Leu Tyr Asn Trp Ile Pro Ile Val Ala Glu Pro Leu
85 90 95

Leu Ala Leu Leu Ala Ile Ala Gly Ala Ala Ala Ile Ile Glu Thr Ile
100 105 110

Thr Gly Tyr Phe Met Gly Glu
115

<210> SEQ ID NO 81
<211> LENGTH: 61
<212> TYPE: PRT
<213> ORGANISM: Bacillus anthracis

<400> SEQUENCE: 81

Met Phe Ala Val Ser Asn Asn Pro Arg Gln Asn Ser Tyr Asp Leu Gln
1 5 10 15

Gln Trp Tyr His Met Gln Gln Gln His Gln Ala Gln Gln Gln Ala Tyr
20 25 30

Gln Glu Gln Leu Gln Gln Gln Gly Phe Val Lys Lys Lys Gly Cys Asn
35 40 45

Cys Gly Lys Lys Lys Ser Thr Ile Lys His Tyr Glu Glu
50 55 60

<210> SEQ ID NO 82
<211> LENGTH: 481
<212> TYPE: PRT
<213> ORGANISM: Bacillus anthracis

<400> SEQUENCE: 82

Met Ser Arg Tyr Asp Asp Ser Gln Asn Lys Phe Ser Lys Pro Cys Phe
1 5 10 15

Pro Ser Ser Ala Gly Arg Ile Pro Asn Thr Pro Ser Ile Pro Val Thr
20 25 30

Lys Ala Gln Leu Arg Thr Phe Arg Ala Ile Ile Ile Asp Leu Thr Lys
35 40 45

Ile Ile Pro Lys Leu Phe Ala Asn Pro Ser Pro Gln Asn Ile Glu Asp
50 55 60

Leu Ile Asp Thr Leu Asn Leu Leu Ser Lys Phe Ile Cys Ser Leu Asp
65 70 75 80

Ala Ala Ser Ser Leu Lys Ala Gln Gly Leu Ala Ile Ile Lys Asn Leu
85 90 95

Ile Thr Ile Leu Lys Asn Pro Thr Phe Val Ala Ser Ala Val Phe Ile
100 105 110

```
Glu Leu Gln Asn Leu Ile Asn Tyr Leu Leu Ser Ile Thr Lys Leu Phe
        115                 120                 125

Arg Ile Asp Pro Cys Thr Leu Gln Glu Leu Leu Lys Leu Ile Ala Ala
    130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Gly Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
        195                 200                 205

Gly Pro Gln Gly Ala Gln Gly Pro Ala Gly Ala Thr Gly Ala Thr Gly
    210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
                245                 250                 255

Gly Val Gln Gly Pro Thr Gly Ala Thr Gly Ile Gly Val Thr Gly Pro
            260                 265                 270

Thr Gly Pro Ser Gly Gly Pro Ala Gly Ala Thr Gly Pro Gln Gly Pro
        275                 280                 285

Gln Gly Asn Thr Gly Ala Thr Gly Pro Gln Gly Ile Gln Gly Pro Ala
    290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
        355                 360                 365

Gln Phe Asn Asn Phe Ile Phe Asn Thr Ala Ile Asn Val Asn Asn Ile
    370                 375                 380

Ile Phe Asn Gly Thr Asp Thr Val Thr Val Ile Asn Ala Gly Ile Tyr
385                 390                 395                 400

Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
        435                 440                 445

Thr Ala Gly Ala Asn Ile Ser Val Gln Ser Thr Leu Asn Glu Ile Thr
    450                 455                 460

Ile Pro Ala Thr Gly Asn Thr Asn Ile Arg Leu Thr Val Phe Arg Ile
465                 470                 475                 480

Ala
```

<210> SEQ ID NO 83
<211> LENGTH: 275
<212> TYPE: PRT
<213> ORGANISM: Bacillus thuringiensis

<400> SEQUENCE: 83

```
Met Lys Met Lys Arg Gly Ile Thr Thr Leu Leu Ser Val Ala Val Leu
1               5                   10                  15

Ser Thr Ser Leu Val Ala Cys Ser Gly Ile Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160

Leu Glu Arg Val Gly Ala Pro Gln Ala Thr Lys Glu His Ile Leu Leu
                165                 170                 175

Gln Asp Pro Lys Glu Lys Gly Lys Glu Lys Arg Arg Glu Leu Val Ser
            180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
    210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg Arg Asp Asn Leu Lys Ser Phe
            260                 265                 270

Asp Thr Lys
        275


<210> SEQ ID NO 84
<211> LENGTH: 795
<212> TYPE: PRT
<213> ORGANISM: Bacillus thuringiensis

<400> SEQUENCE: 84

Met Lys Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95
```

-continued

```
Thr Gln Glu Ala Ser Asp Phe Met Lys Lys Val Lys Asp Ala Lys Met
            100                 105                 110

Arg Glu Asn Glu Gln Ala Gln Gln Pro Glu Val Gly Pro Val Ala Gly
        115                 120                 125

Gln Gly Ala Ala Leu Asn Pro Gly Lys Leu Asn Gly Lys Val Pro Thr
    130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                165                 170                 175

Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
        195                 200                 205

Ser Lys Ile Asn Thr Phe Lys Gln Tyr Tyr Glu Glu Gln Ser Gly Gly
    210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                245                 250                 255

Gly Pro Leu Gly Pro Lys Asp Leu Val Lys Glu Ala Leu Lys Ala Ala
            260                 265                 270

Val Ala Lys Gly Ile Asn Leu Ala Asp Phe Asp Gln Tyr Asp Gln Tyr
        275                 280                 285

Asp Gln Asn Gly Asn Gly Asn Lys Asn Glu Pro Asp Gly Ile Ile Asp
    290                 295                 300

His Leu Met Val Val His Ala Gly Val Gly Gln Glu Ala Gly Gly Gly
305                 310                 315                 320

Lys Leu Lys Asp Asp Ala Ile Trp Ser His Arg Ser Lys Leu Gly Ser
                325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
        355                 360                 365

Val Gly Val Phe Ala His Glu Tyr Gly His Asp Leu Gly Leu Pro Asp
    370                 375                 380

Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
        435                 440                 445

Lys Gly Ile Gly Val Ala Thr Tyr Val Asp Gln Ser Thr Thr Lys Ser
    450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                485                 490                 495

Asn Asp Ile His Thr Thr Leu Glu Thr Pro Val Phe Asp Leu Thr Asn
            500                 505                 510
```

```
Ala Lys Asp Ala Lys Phe Asp Tyr Lys Ala Phe Tyr Glu Leu Glu Ala
        515                 520                 525

Lys Tyr Asp Phe Leu Asp Val Tyr Ala Ile Ala Glu Asp Gly Thr Lys
    530                 535                 540

Thr Arg Ile Asp Arg Met Gly Glu Lys Asp Ile Lys Gly Gly Ala Asp
545                 550                 555                 560

Thr Thr Asp Gly Lys Trp Val Asp Lys Ser Tyr Asp Leu Ser Gln Phe
                565                 570                 575

Lys Gly Lys Lys Val Lys Leu Gln Phe Glu Tyr Leu Thr Asp Ile Ala
            580                 585                 590

Val Ala Tyr Lys Gly Phe Ala Leu Asp Asn Ala Ala Leu Thr Val Asp
        595                 600                 605

Gly Lys Val Val Phe Ser Asp Asp Ala Glu Gly Gln Pro Ala Met Thr
    610                 615                 620

Leu Lys Gly Phe Thr Val Ser Asn Gly Phe Glu Gln Lys Lys His Asn
625                 630                 635                 640

Tyr Tyr Val Glu Trp Arg Asn Tyr Ala Gly Ser Asp Thr Ala Leu Gln
                645                 650                 655

Tyr Ala Arg Gly Pro Val Phe Asn Thr Gly Met Val Val Trp Tyr Ala
            660                 665                 670

Asp Gln Ser Phe Thr Asp Asn Trp Val Gly Val His Pro Gly Glu Gly
        675                 680                 685

Phe Leu Gly Val Val Asp Ser His Pro Glu Ala Ile Val Gly Thr Leu
    690                 695                 700

Asn Gly Gln Pro Thr Val Lys Ser Ser Thr Arg Tyr Gln Ile Ala Asp
705                 710                 715                 720

Ala Ala Phe Ser Phe Asp Gln Thr Pro Ala Trp Lys Val Asn Ser Pro
                725                 730                 735

Thr Arg Gly Ile Phe Asp Tyr Lys Gly Leu Pro Gly Val Ala Lys Phe
            740                 745                 750

Asp Asp Ser Lys Gln Tyr Ile Asn Ser Val Ile Pro Asp Ala Gly Arg
        755                 760                 765

Lys Leu Pro Lys Leu Gly Leu Lys Phe Glu Val Val Gly Gln Ala Glu
    770                 775                 780

Asp Lys Ser Ala Gly Ala Val Trp Leu His Arg
785                 790                 795


<210> SEQ ID NO 85
<211> LENGTH: 169
<212> TYPE: DNA
<213> ORGANISM: Bacillus anthracis

<400> SEQUENCE: 85

taatcaccct cttccaaatc aatcatatgt tatacatata ctaaactttc catttttta      60

aattgttcaa gtagtttaag atttcttttc aataattcaa atgtccgtgt cattttcttt    120

cggttttgca tctactatat aatgaacgct ttatggaggt gaatttatg                169


<210> SEQ ID NO 86
<211> LENGTH: 303
<212> TYPE: DNA
<213> ORGANISM: Bacillus anthracis

<400> SEQUENCE: 86

atttatttca ttcaattttt cctatttagt acctaccgca ctcacaaaaa gcacctctca      60

ttaatttata ttatagtcat tgaaatctaa tttaatgaaa tcatcatact atatgtttta    120
```

-continued

```
taagaagtaa aggtaccata cttaattaat acatatctat acacttcaat atcacagcat    180

gcagttgaat tatatccaac tttcatttca aattaaataa gtgcctccgc tattgtgaat    240

gtcatttact ctccctacta catttaataa ttatgacaag caatcatagg aggttactac    300

atg                                                                  303
```

<210> SEQ ID NO 87
<211> LENGTH: 173
<212> TYPE: DNA
<213> ORGANISM: Bacillus anthracis

<400> SEQUENCE: 87

```
aattacataa caagaactac attagggagc aagcagtcta gcgaaagcta actgcttttt     60

tattaaataa ctattttatt aaatttcata tatacaatcg cttgtccatt tcatttggct    120

ctacccacgc atttactatt agtaatatga atttttcaga ggtggatttt att           173
```

<210> SEQ ID NO 88
<211> LENGTH: 124
<212> TYPE: DNA
<213> ORGANISM: Bacillus weihenstephensis

<400> SEQUENCE: 88

```
ctatgattta agatacacaa tagcaaaaga gaaacatatt atataacgat aaatgaaact     60

tatgtatatg tatggtaact gtatatatta ctacaataca gtatactcat aggaggtagg    120

tatg                                                                 124
```

<210> SEQ ID NO 89
<211> LENGTH: 376
<212> TYPE: DNA
<213> ORGANISM: Bacillus weihenstephensis

<400> SEQUENCE: 89

```
ggtaggtaga tttgaaatat gatgaagaaa aggaataact aaaaggagtc gatatccgac     60

tccttttagt tataaataat gtggaattag agtataattt tatataggta tattgtatta    120

gatgaacgct ttatccttta attgtgatta atgatggatt gtaagagaag ggcttacag     180

tccttttttt atggtgttct ataagccttt ttaaaagggg taccacccca cacccaaaaa    240

caggggggt tataactaca tattggatgt tttgtaacgt acaagaatcg gtattaatta     300

ccctgtaaat aagttatgtg tatataaggt aactttatat attctcctac aataaaataa    360

aggaggtaat aaagtg                                                    376
```

<210> SEQ ID NO 90
<211> LENGTH: 225
<212> TYPE: DNA
<213> ORGANISM: Bacillus thuringiensis

<400> SEQUENCE: 90

```
aacccttaat gcattggtta aacattgtaa agtctaaagc atggataatg ggcgagaagt     60

aagtagattg ttaacaccct gggtcaaaaa ttgatattta gtaaaattag ttgcactttg    120

tgcatttttt cataagatga gtcatatgtt ttaaattgta gtaatgaaaa acagtattat    180

atcataatga attggtatct taataaaaga gatggaggta actta                    225
```

<210> SEQ ID NO 91
<211> LENGTH: 125
<212> TYPE: DNA

<213> ORGANISM: Bacillus thuringiensis

<400> SEQUENCE: 91
taattccacc ttcccttatc ctctttcgcc tatttaaaaa aaggtcttga gattgtgacc 60
aaatctcctc aactccaata tcttattaat gtaaatacaa acaagaagat aaggagtgac 120
attaa 125

<210> SEQ ID NO 92
<211> LENGTH: 144
<212> TYPE: DNA
<213> ORGANISM: Bacillus thuringiensis

<400> SEQUENCE: 92
aggatgtctt tttttatatt gtattatgta catccctact atataaattc cctgctttta 60
tcgtaagaat taacgtaata tcaaccatat cccgttcata ttgtagtagt gtatgtcaga 120
actcacgaga aggagtgaac ataa 144

<210> SEQ ID NO 93
<211> LENGTH: 126
<212> TYPE: DNA
<213> ORGANISM: Bacillus thuringiensis

<400> SEQUENCE: 93
ttaatgtcac tccttatctt cttgtttgta tttacattaa taagatattg gagttgagga 60
gatttggtca caatctcaag accttttttt taaataggcg aaagaggata agggaaggtg 120
gaatta 126

<210> SEQ ID NO 94
<211> LENGTH: 103
<212> TYPE: DNA
<213> ORGANISM: Bacillus thuringiensis

<400> SEQUENCE: 94
atatattttc ataatacgag aaaaagcgga gtttaaaaga atgagggaac ggaaataaag 60
agttgttcat atagtaaata gacagaattg acagtagagg aga 103

<210> SEQ ID NO 95
<211> LENGTH: 169
<212> TYPE: DNA
<213> ORGANISM: Bacillus thuringiensis

<400> SEQUENCE: 95
aaactaaata atgagctaag catggattgg gtggcagaat tatctgccac ccaatccatg 60
cttaacgagt attattatgt aaatttctta aaattgggaa cttgtctaga acatagaacc 120
tgtccttttc attaactgaa agtagaaaca gataaaggag tgaaaaaaca 169

<210> SEQ ID NO 96
<211> LENGTH: 111
<212> TYPE: DNA
<213> ORGANISM: Bacillus thuringiensis

<400> SEQUENCE: 96
attcactaca acggggatga gtttgatgcg gatacatatg agaagtaccg gaaagtgttt 60
gtagaacatt acaaagatat attatctcca tcataaagga gagatgcaaa g 111

<210> SEQ ID NO 97
<211> LENGTH: 273

<212> TYPE: DNA
<213> ORGANISM: Bacillus anthracis

<400> SEQUENCE: 97
cgcgcaccac ttcgtcgtac aacaacgcaa gaagaagttg gggatacagc agtattctta 60
ttcagtgatt tagcacgcgg cgtaacagga gaaaacattc acgttgattc agggtatcat 120
atcttaggat aaatataata ttaattttaa aggacaatct ctacatgttg agattgtcct 180
ttttatttgt tcttagaaag aacgattttt aacgaaagtt cttaccacgt tatgaatata 240
agtataatag tacacgattt attcagctac gta 273

<210> SEQ ID NO 98
<211> LENGTH: 303
<212> TYPE: DNA
<213> ORGANISM: Bacillus anthracis

<400> SEQUENCE: 98
tgaagtatct agagctaatt tacgcaaagg aatctcagga caacactttc gcaacaccta 60
tattttaaat ttaataaaaa aagagactcc ggagtcagaa attataaagc tagctgggtt 120
caaatcaaaa atttcactaa aacgatatta tcaatacgca gaaaatggaa aaaacgcctt 180
atcataaggc gtttttttcca tttttttcttc aaacaaacga ttttactatg accatttaac 240
taatttttgc atctactatg atgagtttca ttcacattct cattagaaag gagagattta 300
atg 303

<210> SEQ ID NO 99
<211> LENGTH: 240
<212> TYPE: DNA
<213> ORGANISM: Bacillus anthracis

<400> SEQUENCE: 99
tatatcatat gtaaaattag ttcttattcc cacatatcat atagaatcgc catattatac 60
atgcagaaaa ctaagtatgg tattattctt aaattgttta gcaccttcta atattacaga 120
tagaatccgt catttttcaac agtgaacatg gatttcttct gaacacaact ctttttcttt 180
ccttatttcc aaaaagaaaa gcagcccatt ttaaaatacg gctgcttgta atgtacatta 240

<210> SEQ ID NO 100
<211> LENGTH: 267
<212> TYPE: DNA
<213> ORGANISM: Bacillus thuringiensis

<400> SEQUENCE: 100
tatcacataa ctctttattt ttaatatttc gacataaagt gaaactttaa tcagtggggg 60
ctttgttcat ccccccactg attattaatt gaaccaaggg ataaaaagat agagggtctg 120
accagaaaac tggagggcat gattctataa caaaaagctt aatgtttata gaattatgtc 180
tttttatata gggagggtag taaacagaga tttggacaaa aatgcaccga tttatctgaa 240
ttttaagttt tataaagggg agaaatg 267

<210> SEQ ID NO 101
<211> LENGTH: 124
<212> TYPE: DNA
<213> ORGANISM: Bacillus thuringiensis

<400> SEQUENCE: 101
attttttact tagcagtaaa actgatatca gttttactgc tttttcattt ttaaattcaa 60

-continued tcattaaatc ttccttttct acatagtcat aatgttgtat gacattccgt aggaggcact 120
tata 124

<210> SEQ ID NO 102
<211> LENGTH: 170
<212> TYPE: DNA
<213> ORGANISM: Bacillus thuringiensis

<400> SEQUENCE: 102
acataaattc acctccataa agcgttcatt atatagtaga tgcaaaaccg aaagaaaatg 60
acacggacat ttgaattatt gaaaagaaat cttaaactac ttgaacaatt taaaaaaatg 120
gaaagtttag tatatgtata acatatgatt gatttggaag agggtgatta 170

<210> SEQ ID NO 103
<211> LENGTH: 212
<212> TYPE: DNA
<213> ORGANISM: Bacillus thuringiensis

<400> SEQUENCE: 103
ttctattttc caacataaca tgctacgatt aaatggtttt ttgcaaatgc cttcttggga 60
agaaggatta gagcgttttt ttatagaaac caaaagtcat taacaatttt aagttaatga 120 ctttttgtt tgcctttaag aggttttatg ttactataat tatagtatca ggtactaata 180
acaagtataa gtatttctgg gaggatatat ca 212

<210> SEQ ID NO 104
<211> LENGTH: 1500
<212> TYPE: DNA
<213> ORGANISM: Bacillus subtilis

<400> SEQUENCE: 104
atgaaacggt caatctcgat ttttattacg tgtttattga ttacgttatt gacaatgggc 60
ggcatgatag cttcgccggc atcagcagca gggacaaaaa cgccagtagc caagaatggc 120
cagcttagca taaaaggtac acagctcgtt aaccgagacg gtaaagcggt acagctgaag 180
gggatcagtt cacacggatt gcaatggtat ggagaatatg tcaataaaga cagcttaaaa 240
tggctgagag atgattgggg tatcaccgtt ttccgtgcag cgatgtatac ggcagatggc 300
ggttatattg acaacccgtc cgtgaaaaat aaagtaaaag aagcggttga agcggcaaaa 360
gagcttggga tatatgtcat cattgactgg catatcttaa atgacggtaa tccaaaccaa 420
aataaagaga aggcaaaaga attcttcaag gaaatgtcaa gcctttacgg aaacacgcca 480
aacgtcattt atgaaattgc aaacgaacca aacggtgatg tgaactggaa gcgtgatatt 540
aaaccatatg cggaagaagt gatttcagtt atccgcaaaa atgatccaga caacatcatc 600
attgtcggaa ccggtacatg gagccaggat gtgaatgatg ctgccgatga ccagctaaaa 660
gatgcaaacg ttatgtacgc acttcatttt tatgccggca cacacggcca atttttacgg 720
gataaagcaa actatgcact cagcaaagga gcacctattt ttgtgacaga gtggggaaca 780
agcgacgcgt ctggcaatgg cggtgtattc cttgatcaat cgagggaatg gctgaaatat 840
ctcgacagca agaccattag ctgggtgaac tggaatcttt ctgataagca ggaatcatcc 900
tcagctttaa agccgggggc atctaaaaca ggcggctggc ggttgtcaga tttatctgct 960
tcaggaacat tcgttagaga aaacattctc ggcaccaaag attcgacgaa ggacattcct 1020
gaaacgccat caaaagataa acccacacag gaaaatggta tttctgtaca gtacagagca 1080
ggggatggga gtatgaacag caaccaaatc cgtccgcagc ttcaaataaa aaataacggc 1140
aataccacgg ttgatttaaa agatgtcact gcccgttact ggtataaagc gaaaaacaaa 1200
ggccaaaact ttgactgtga ctacgcgcag attggatgcg gcaatgtgac acacaagttt 1260
gtgacgttgc ataaaccaaa gcaaggtgca gatacctatc tggaacttgg atttaaaaac 1320
ggaacgttgg caccgggagc aagcacaggg aatattcagc tccgtcttca caatgatgac 1380
tggagcaatt atgcacaaag cggcgattat tccttttca aatcaaatac gtttaaaaca 1440
acgaaaaaaa tcacattata tgatcaagga aaactgattt ggggaacaga accaaattag 1500

<210> SEQ ID NO 105
<211> LENGTH: 852
<212> TYPE: DNA
<213> ORGANISM: Bacillus thuringiensis

<400> SEQUENCE: 105
atgaaaaaga aagtacttgc tttagcggca gctattacat tggttgctcc attacaaagt 60
gttgcatttg ctcatgaaaa tgatgggga cagagatttg gagttattcc gcgctggtct 120
gctgaagata aacataaaga aggcgtgaat tctcatttat ggattgtaaa tcgtgcaatt 180
gatattatgt ctcgtaatac aacacttgta aaacaagatc gagttgcact attaaatgaa 240
tggcgtactg agttagagaa cggtatttat gctgctgact atgaaaatcc ttattatgat 300
aatagcacat ttgcttcaca tttctatgac cctgacaatg ggaaaactta tattccgtat 360
gcaaagcagg caaaggaaac tggagctaaa tattttaaat tagctggtga gtcttacaaa 420
aataaagata tgcaacaagc attcttctat ttaggattat ctcttcatta tctaggggat 480
gtaaaccaac cgatgcatgc agcaaacttt acaaaccttt cgtatccaca agggttccat 540
tctaaatatg aaaactttgt agatacgata aaagataact ataaagtaac ggatggaaat 600
ggatattgga actggaaagg tacgaatcca gaagattgga ttcatggagc ggcagtagtt 660
gcgaaacaag attacgctgg cattgtaaat gataatacga aagattggtt cgtgagagct 720
gctgtatcac aagaatatgc agataaatgg cgcgctgaag ttacaccaat gacaggtaag 780
cgtttaatgg atgcacaacg tgttactgct ggatatattc agctttggtt tgatacgtac 840
ggagatcgtt aa 852

<210> SEQ ID NO 106
<211> LENGTH: 729
<212> TYPE: DNA
<213> ORGANISM: Bacillus subtilis

<400> SEQUENCE: 106
gcgggactga ataaagatca aaagcgccgg gcggaacagc tgacaagtat ctttgaaaac 60
ggcacaacgg agatccaata tggatatgta gagcgattgg atgacgggcg aggctataca 120
tgcggacggg caggctttac aacggctacc ggggatgcat tggaagtagt ggaagtatac 180
acaaaggcag ttccgaataa caaactgaaa aagtatctgc ctgaattgcg ccgtctggcc 240
aaggaagaaa gcgatgatac aagcaatctc aagggattcg cttctgcctg gaagtcgctt 300
gcaaatgata aggaatttcg cgccgctcaa gacaaagtaa atgaccattt gtattatcag 360
cctgccatga aacgatcgga taatgccgga ctaaaaacag cattggcaag agctgtgatg 420
tacgatacgg ttattcagca tggcgatggt gatgaccctg actcttttta tgccttgatt 480
aaacgtacga acaaaaaagc gggcggatca cctaaagacg gaatagacga gaagaagtgg 540
ttgaataaat tcttggacgt acgctatgac gatctgatga atccggccaa tcatgacacc 600

```
cgtgacgaat ggagagaatc agttgcccgt gtggacgtgc ttcgctctat cgccaaggag    660

aacaactata atctaaacgg accgattcat gttcgttcaa acgagtacgg taattttgta    720

atcaaataa                                                            729


<210> SEQ ID NO 107
<211> LENGTH: 499
<212> TYPE: PRT
<213> ORGANISM: Bacillus subtilis

<400> SEQUENCE: 107

Met Lys Arg Ser Ile Ser Ile Phe Ile Thr Cys Leu Leu Ile Thr Leu
1               5                   10                  15

Leu Thr Met Gly Gly Met Ile Ala Ser Pro Ala Ser Ala Ala Gly Thr
            20                  25                  30

Lys Thr Pro Val Ala Lys Asn Gly Gln Leu Ser Ile Lys Gly Thr Gln
        35                  40                  45

Leu Val Asn Arg Asp Gly Lys Ala Val Gln Leu Lys Gly Ile Ser Ser
    50                  55                  60

His Gly Leu Gln Trp Tyr Gly Glu Tyr Val Asn Lys Asp Ser Leu Lys
65                  70                  75                  80

Trp Leu Arg Asp Asp Trp Gly Ile Thr Val Phe Arg Ala Ala Met Tyr
                85                  90                  95

Thr Ala Asp Gly Gly Tyr Ile Asp Asn Pro Ser Val Lys Asn Lys Val
            100                 105                 110

Lys Glu Ala Val Glu Ala Ala Lys Glu Leu Gly Ile Tyr Val Ile Ile
        115                 120                 125

Asp Trp His Ile Leu Asn Asp Gly Asn Pro Asn Gln Asn Lys Glu Lys
    130                 135                 140

Ala Lys Glu Phe Phe Lys Glu Met Ser Ser Leu Tyr Gly Asn Thr Pro
145                 150                 155                 160

Asn Val Ile Tyr Glu Ile Ala Asn Glu Pro Asn Gly Asp Val Asn Trp
                165                 170                 175

Lys Arg Asp Ile Lys Pro Tyr Ala Glu Glu Val Ile Ser Val Ile Arg
            180                 185                 190

Lys Asn Asp Pro Asp Asn Ile Ile Ile Val Gly Thr Gly Thr Trp Ser
        195                 200                 205

Gln Asp Val Asn Asp Ala Ala Asp Asp Gln Leu Lys Asp Ala Asn Val
    210                 215                 220

Met Tyr Ala Leu His Phe Tyr Ala Gly Thr His Gly Gln Phe Leu Arg
225                 230                 235                 240

Asp Lys Ala Asn Tyr Ala Leu Ser Lys Gly Ala Pro Ile Phe Val Thr
                245                 250                 255

Glu Trp Gly Thr Ser Asp Ala Ser Gly Asn Gly Gly Val Phe Leu Asp
            260                 265                 270

Gln Ser Arg Glu Trp Leu Lys Tyr Leu Asp Ser Lys Thr Ile Ser Trp
        275                 280                 285

Val Asn Trp Asn Leu Ser Asp Lys Gln Glu Ser Ser Ser Ala Leu Lys
    290                 295                 300

Pro Gly Ala Ser Lys Thr Gly Gly Trp Arg Leu Ser Asp Leu Ser Ala
305                 310                 315                 320

Ser Gly Thr Phe Val Arg Glu Asn Ile Leu Gly Thr Lys Asp Ser Thr
                325                 330                 335

Lys Asp Ile Pro Glu Thr Pro Ser Lys Asp Lys Pro Thr Gln Glu Asn
            340                 345                 350
```

```
Gly Ile Ser Val Gln Tyr Arg Ala Gly Asp Gly Ser Met Asn Ser Asn
        355                 360                 365

Gln Ile Arg Pro Gln Leu Gln Ile Lys Asn Asn Gly Asn Thr Thr Val
    370                 375                 380

Asp Leu Lys Asp Val Thr Ala Arg Tyr Trp Tyr Lys Ala Lys Asn Lys
385                 390                 395                 400

Gly Gln Asn Phe Asp Cys Asp Tyr Ala Gln Ile Gly Cys Gly Asn Val
                405                 410                 415

Thr His Lys Phe Val Thr Leu His Lys Pro Lys Gln Gly Ala Asp Thr
            420                 425                 430

Tyr Leu Glu Leu Gly Phe Lys Asn Gly Thr Leu Ala Pro Gly Ala Ser
        435                 440                 445

Thr Gly Asn Ile Gln Leu Arg Leu His Asn Asp Asp Trp Ser Asn Tyr
    450                 455                 460

Ala Gln Ser Gly Asp Tyr Ser Phe Phe Lys Ser Asn Thr Phe Lys Thr
465                 470                 475                 480

Thr Lys Lys Ile Thr Leu Tyr Asp Gln Gly Lys Leu Ile Trp Gly Thr
                485                 490                 495

Glu Pro Asn


<210> SEQ ID NO 108
<211> LENGTH: 283
<212> TYPE: PRT
<213> ORGANISM: Bacillus thuringiensis

<400> SEQUENCE: 108

Met Lys Lys Lys Val Leu Ala Leu Ala Ala Ala Ile Thr Leu Val Ala
1               5                   10                  15

Pro Leu Gln Ser Val Ala Phe Ala His Glu Asn Asp Gly Gly Gln Arg
            20                  25                  30

Phe Gly Val Ile Pro Arg Trp Ser Ala Glu Asp Lys His Lys Glu Gly
        35                  40                  45

Val Asn Ser His Leu Trp Ile Val Asn Arg Ala Ile Asp Ile Met Ser
    50                  55                  60

Arg Asn Thr Thr Leu Val Lys Gln Asp Arg Val Ala Leu Leu Asn Glu
65                  70                  75                  80

Trp Arg Thr Glu Leu Glu Asn Gly Ile Tyr Ala Ala Asp Tyr Glu Asn
                85                  90                  95

Pro Tyr Tyr Asp Asn Ser Thr Phe Ala Ser His Phe Tyr Asp Pro Asp
            100                 105                 110

Asn Gly Lys Thr Tyr Ile Pro Tyr Ala Lys Gln Ala Lys Glu Thr Gly
        115                 120                 125

Ala Lys Tyr Phe Lys Leu Ala Gly Glu Ser Tyr Lys Asn Lys Asp Met
    130                 135                 140

Gln Gln Ala Phe Phe Tyr Leu Gly Leu Ser Leu His Tyr Leu Gly Asp
145                 150                 155                 160

Val Asn Gln Pro Met His Ala Ala Asn Phe Thr Asn Leu Ser Tyr Pro
                165                 170                 175

Gln Gly Phe His Ser Lys Tyr Glu Asn Phe Val Asp Thr Ile Lys Asp
            180                 185                 190

Asn Tyr Lys Val Thr Asp Gly Asn Gly Tyr Trp Asn Trp Lys Gly Thr
        195                 200                 205

Asn Pro Glu Asp Trp Ile His Gly Ala Ala Val Val Ala Lys Gln Asp
    210                 215                 220
```

-continued

```
Tyr Ala Gly Ile Val Asn Asp Asn Thr Lys Asp Trp Phe Val Arg Ala
225                 230                 235                 240

Ala Val Ser Gln Glu Tyr Ala Asp Lys Trp Arg Ala Glu Val Thr Pro
                245                 250                 255

Met Thr Gly Lys Arg Leu Met Asp Ala Gln Arg Val Thr Ala Gly Tyr
            260                 265                 270

Ile Gln Leu Trp Phe Asp Thr Tyr Gly Asp Arg
        275                 280


<210> SEQ ID NO 109
<211> LENGTH: 244
<212> TYPE: PRT
<213> ORGANISM: Bacillus subtilis

<400> SEQUENCE: 109

Leu Glu Ala Gly Leu Asn Lys Asp Gln Lys Arg Arg Ala Glu Gln Leu
1               5                   10                  15

Thr Ser Ile Phe Glu Asn Gly Thr Thr Glu Ile Gln Tyr Gly Tyr Val
            20                  25                  30

Glu Arg Leu Asp Asp Gly Arg Gly Tyr Thr Cys Gly Arg Ala Gly Phe
        35                  40                  45

Thr Thr Ala Thr Gly Asp Ala Leu Glu Val Val Glu Val Tyr Thr Lys
    50                  55                  60

Ala Val Pro Asn Asn Lys Leu Lys Lys Tyr Leu Pro Glu Leu Arg Arg
65                  70                  75                  80

Leu Ala Lys Glu Glu Ser Asp Asp Thr Ser Asn Leu Lys Gly Phe Ala
                85                  90                  95

Ser Ala Trp Lys Ser Leu Ala Asn Asp Lys Glu Phe Arg Ala Ala Gln
            100                 105                 110

Asp Lys Val Asn Asp His Leu Tyr Tyr Gln Pro Ala Met Lys Arg Ser
        115                 120                 125

Asp Asn Ala Gly Leu Lys Thr Ala Leu Ala Arg Ala Val Met Tyr Asp
    130                 135                 140

Thr Val Ile Gln His Gly Asp Gly Asp Asp Pro Asp Ser Phe Tyr Ala
145                 150                 155                 160

Leu Ile Lys Arg Thr Asn Lys Lys Ala Gly Gly Ser Pro Lys Asp Gly
                165                 170                 175

Ile Asp Glu Lys Lys Trp Leu Asn Lys Phe Leu Asp Val Arg Tyr Asp
            180                 185                 190

Asp Leu Met Asn Pro Ala Asn His Asp Thr Arg Asp Glu Trp Arg Glu
        195                 200                 205

Ser Val Ala Arg Val Asp Val Leu Arg Ser Ile Ala Lys Glu Asn Asn
    210                 215                 220

Tyr Asn Leu Asn Gly Pro Ile His Val Arg Ser Asn Glu Tyr Gly Asn
225                 230                 235                 240

Phe Val Ile Lys
```